US012778752B2

(12) United States Patent
Stearns et al.

(10) Patent No.: US 12,778,752 B2
(45) Date of Patent: Nov. 3, 2026

(54) VALVE REPAIR IMPLANT WITH LEAFLET TENSION INDICATION

(71) Applicant: EDWARDS LIFESCIENCES CORPORATION, Irvine, CA (US)

(72) Inventors: Grant Matthew Stearns, Tustin, CA (US); Chris J. Okos, Huntington Beach, CA (US); Seung-Beom Yi, Mission Viejo, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 761 days.

(21) Appl. No.: 18/168,445

(22) Filed: Feb. 13, 2023

(65) Prior Publication Data

US 2023/0181314 A1 Jun. 15, 2023

Related U.S. Application Data

(63) Continuation of application No. PCT/US2021/045930, filed on Aug. 13, 2021.
(Continued)

(51) Int. Cl.
*A61F 2/24* (2006.01)

(52) U.S. Cl.
CPC ................ *A61F 2/246* (2013.01); *A61F 2/24* (2013.01); *A61F 2220/0016* (2013.01);
(Continued)

(58) Field of Classification Search
CPC .... A61F 2/2454–246; A61F 2220/0016; A61F 2250/0096–0098; A61F 2250/0073–0074
See application file for complete search history.

(56) References Cited

U.S. PATENT DOCUMENTS

| | | | |
|---|---|---|---|
| 809,139 | A | 1/1906 | Saxton |
| 3,874,388 | A | 4/1975 | King et al. |

(Continued)

FOREIGN PATENT DOCUMENTS

| | | | |
|---|---|---|---|
| CN | 1142351 | A | 2/1997 |
| CN | 106175845 | A | 12/2016 |

(Continued)

OTHER PUBLICATIONS

Al Zaibag et al., "Percutaneous Balloon Valvotomy in Tricuspid Stenosis", British Heart Journal, vol. 57, No. 1, Jan. 1987.

(Continued)

*Primary Examiner* — Rebecca S Preston
(74) *Attorney, Agent, or Firm* — Anya Adams

(57) ABSTRACT

An implantable device or implant includes an anchor portion comprising one or more anchors. The anchors are configured to attach to one or more leaflets of a native heart valve. The anchors are configured to move between an open position and a closed position. The device or implant includes an indication feature that is movable between an allowable tension position and an exceeded tension position. When the anchors are attached to the leaflets of the native heart valve, the indication feature indicates to a user when an amount of force applied to the anchor portion by the leaflets of the native heart valve exceeds a pre-set or predetermined amount of force.

14 Claims, 54 Drawing Sheets

Related U.S. Application Data

(60) Provisional application No. 63/066,097, filed on Aug. 14, 2020.

(52) U.S. Cl.
CPC ................ *A61F 2230/0054* (2013.01); *A61F 2250/0007* (2013.01); *A61F 2250/0069* (2013.01)

(56) References Cited

U.S. PATENT DOCUMENTS

| | | | |
|---|---|---|---|
| 4,340,091 | A | 7/1982 | Skelton et al. |
| 4,506,669 | A | 3/1985 | Blake |
| 4,590,937 | A | 5/1986 | Deniega |
| 4,693,248 | A | 9/1987 | Failla |
| 4,803,983 | A | 2/1989 | Siegel |
| 5,125,895 | A | 6/1992 | Buchbinder et al. |
| 5,171,252 | A | 12/1992 | Friedland |
| 5,195,962 | A | 3/1993 | Martin et al. |
| 5,292,326 | A | 3/1994 | Green et al. |
| 5,327,905 | A | 7/1994 | Avitall |
| 5,363,861 | A | 11/1994 | Edwards et al. |
| 5,370,685 | A | 12/1994 | Stevens |
| 5,389,077 | A | 2/1995 | Melinyshyn et al. |
| 5,411,552 | A | 5/1995 | Andersen et al. |
| 5,450,860 | A | 9/1995 | O'Connor |
| 5,456,674 | A | 10/1995 | Bos et al. |
| 5,474,057 | A | 12/1995 | Makower et al. |
| 5,478,353 | A | 12/1995 | Yoon |
| 5,487,746 | A | 1/1996 | Yu et al. |
| 5,565,004 | A | 10/1996 | Christoudias |
| 5,607,462 | A | 3/1997 | Imran |
| 5,609,598 | A | 3/1997 | Laufer et al. |
| 5,611,794 | A | 3/1997 | Sauer et al. |
| 5,626,607 | A | 5/1997 | Malecki et al. |
| 5,695,504 | A | 12/1997 | Gifford et al. |
| 5,716,417 | A | 2/1998 | Girard et al. |
| 5,727,569 | A | 3/1998 | Benetti et al. |
| 5,741,297 | A | 4/1998 | Simon |
| 5,782,746 | A | 7/1998 | Wright |
| 5,797,960 | A | 8/1998 | Stevens et al. |
| 5,836,311 | A | 11/1998 | Borst et al. |
| 5,843,076 | A | 12/1998 | Webster et al. |
| 5,855,590 | A | 1/1999 | Malecki et al. |
| 5,885,271 | A | 3/1999 | Hamilton et al. |
| 5,888,247 | A | 3/1999 | Benetti |
| 5,891,017 | A | 4/1999 | Swindle et al. |
| 5,891,112 | A | 4/1999 | Samson |
| 5,894,843 | A | 4/1999 | Benetti et al. |
| 5,921,979 | A | 7/1999 | Kovac et al. |
| 5,944,738 | A | 8/1999 | Amplatz et al. |
| 5,957,835 | A | 9/1999 | Anderson et al. |
| 5,972,020 | A | 10/1999 | Carpentier et al. |
| 5,980,534 | A | 11/1999 | Gimpelson |
| 6,004,329 | A | 12/1999 | Myers et al. |
| 6,010,531 | A | 1/2000 | Donlon et al. |
| 6,017,358 | A | 1/2000 | Yoon et al. |
| 6,086,600 | A | 7/2000 | Kortenbach |
| 6,120,496 | A | 9/2000 | Whayne et al. |
| 6,132,370 | A | 10/2000 | Furnish et al. |
| 6,162,239 | A | 12/2000 | Manhes |
| 6,165,183 | A | 12/2000 | Kuehn et al. |
| 6,182,664 | B1 | 2/2001 | Cosgrove |
| 6,193,732 | B1 | 2/2001 | Frantzen et al. |
| 6,193,734 | B1 | 2/2001 | Bolduc et al. |
| 6,200,315 | B1 | 3/2001 | Gaiser et al. |
| 6,228,032 | B1 | 5/2001 | Eaton et al. |
| 6,241,743 | B1 | 6/2001 | Levin et al. |
| 6,269,819 | B1 | 8/2001 | Oz et al. |
| 6,269,829 | B1 | 8/2001 | Chen et al. |
| 6,312,447 | B1 | 11/2001 | Grimes |
| 6,461,366 | B1 | 10/2002 | Seguin |
| 6,468,285 | B1 | 10/2002 | Hsu et al. |
| 6,508,806 | B1 | 1/2003 | Hoste |
| 6,508,825 | B1 | 1/2003 | Selmon et al. |
| 6,530,933 | B1 | 3/2003 | Yeung et al. |
| 6,537,290 | B2 | 3/2003 | Adams et al. |
| 6,544,215 | B1 | 4/2003 | Bencini et al. |
| 6,626,930 | B1 | 9/2003 | Allen et al. |
| 6,629,534 | B1 | 10/2003 | St. Goar et al. |
| 6,719,767 | B1 | 4/2004 | Kimblad |
| 6,764,510 | B2 | 7/2004 | Vidlund et al. |
| 6,770,083 | B2 | 8/2004 | Seguin |
| 6,837,867 | B2 | 1/2005 | Kortelling |
| 6,855,137 | B2 | 2/2005 | Bon |
| 6,913,614 | B2 | 7/2005 | Marino et al. |
| 6,939,337 | B2 | 9/2005 | Parker et al. |
| 6,945,956 | B2 | 9/2005 | Waldhauser et al. |
| 7,048,754 | B2 | 5/2006 | Martin et al. |
| 7,101,395 | B2 | 9/2006 | Tremulis et al. |
| 7,125,421 | B2 | 10/2006 | Tremulis et al. |
| 7,288,097 | B2 | 10/2007 | Séguin |
| 7,371,210 | B2 | 5/2008 | Brock et al. |
| 7,464,712 | B2 | 12/2008 | Oz et al. |
| 7,509,959 | B2 | 3/2009 | Oz et al. |
| 7,569,062 | B1 | 8/2009 | Kuehn et al. |
| 7,618,449 | B2 | 11/2009 | Tremulis et al. |
| 7,682,369 | B2 | 3/2010 | Séguin |
| 7,731,706 | B2 | 6/2010 | Potter |
| 7,744,609 | B2 | 6/2010 | Allen et al. |
| 7,748,389 | B2 | 7/2010 | Salahieh et al. |
| 7,753,932 | B2 | 7/2010 | Gingrich et al. |
| 7,758,596 | B2 | 7/2010 | Oz et al. |
| 7,780,723 | B2 | 8/2010 | Taylor |
| 7,803,185 | B2 | 9/2010 | Gabbay |
| 7,824,443 | B2 | 11/2010 | Salahieh et al. |
| 7,981,123 | B2 | 7/2011 | Séguin |
| 7,988,724 | B2 | 8/2011 | Salahieh et al. |
| 8,052,750 | B2 | 11/2011 | Tuval et al. |
| 8,070,805 | B2 | 12/2011 | Vidlund et al. |
| 8,096,985 | B2 | 1/2012 | Legaspi et al. |
| 8,104,149 | B1 | 1/2012 | McGarity |
| 8,133,239 | B2 | 3/2012 | Oz et al. |
| 8,147,542 | B2 | 4/2012 | Maisano et al. |
| 8,172,856 | B2 | 5/2012 | Eigler et al. |
| 8,206,437 | B2 | 6/2012 | Bonhoeffer et al. |
| 8,216,301 | B2 | 7/2012 | Bonhoeffer et al. |
| 8,303,653 | B2 | 11/2012 | Bonhoeffer et al. |
| 8,313,525 | B2 | 11/2012 | Tuval et al. |
| 8,348,995 | B2 | 1/2013 | Tuval et al. |
| 8,348,996 | B2 | 1/2013 | Tuval et al. |
| 8,414,643 | B2 | 4/2013 | Tuval et al. |
| 8,425,404 | B2 | 4/2013 | Wilson et al. |
| 8,449,599 | B2 | 5/2013 | Chau et al. |
| 8,449,606 | B2 | 5/2013 | Eliasen et al. |
| 8,460,368 | B2 | 6/2013 | Taylor et al. |
| 8,470,028 | B2 | 6/2013 | Thornton et al. |
| 8,480,730 | B2 | 7/2013 | Maurer et al. |
| 8,540,767 | B2 | 9/2013 | Zhang |
| 8,579,965 | B2 | 11/2013 | Bonhoeffer et al. |
| 8,585,756 | B2 | 11/2013 | Bonhoeffer et al. |
| 8,652,202 | B2 | 2/2014 | Alon et al. |
| 8,668,733 | B2 | 3/2014 | Haug et al. |
| 8,721,665 | B2 | 5/2014 | Oz et al. |
| 8,740,918 | B2 | 6/2014 | Seguin |
| 8,771,347 | B2 | 7/2014 | DeBoer et al. |
| 8,778,017 | B2 | 7/2014 | Eliasen et al. |
| 8,834,564 | B2 | 9/2014 | Tuval et al. |
| 8,840,663 | B2 | 9/2014 | Salahieh et al. |
| 8,876,894 | B2 | 11/2014 | Tuval et al. |
| 8,876,895 | B2 | 11/2014 | Tuval et al. |
| 8,945,177 | B2 | 2/2015 | Dell et al. |
| 9,034,032 | B2 | 5/2015 | McLean et al. |
| 9,198,757 | B2 | 12/2015 | Schroeder et al. |
| 9,220,507 | B1 | 12/2015 | Patel et al. |
| 9,259,317 | B2 | 2/2016 | Wilson et al. |
| 9,282,972 | B1 | 3/2016 | Patel et al. |
| 9,301,834 | B2 | 4/2016 | Tuval et al. |
| 9,308,360 | B2 | 4/2016 | Bishop et al. |
| 9,387,071 | B2 | 7/2016 | Tuval et al. |
| 9,427,327 | B2 | 8/2016 | Parrish |
| 9,439,763 | B2 | 9/2016 | Geist et al. |
| 9,510,837 | B2 | 12/2016 | Seguin |

(56) References Cited

U.S. PATENT DOCUMENTS 9,510,946 B2 12/2016 Chau et al.
9,572,660 B2 2/2017 Braido et al.
9,642,704 B2 5/2017 Tuval et al.
9,700,445 B2 7/2017 Martin et al.
9,775,963 B2 10/2017 Miller
9,889,002 B2 2/2018 Bonhoeffer et al.
9,949,824 B2 4/2018 Bonhoeffer et al.
10,076,327 B2 9/2018 Ellis et al.
10,076,415 B1 9/2018 Metchik et al.
10,099,050 B2 10/2018 Chen et al.
10,105,221 B2 10/2018 Siegel
10,105,222 B1 10/2018 Metchik et al.
10,111,751 B1 10/2018 Metchik et al.
10,123,873 B1 11/2018 Metchik et al.
10,130,475 B1 11/2018 Metchik et al.
10,136,993 B1 11/2018 Metchik et al.
10,159,570 B1 12/2018 Metchik et al.
10,226,309 B2 3/2019 Ho et al.
10,231,837 B1 3/2019 Metchik et al.
10,238,493 B1 3/2019 Metchik et al.
10,238,494 B2 3/2019 McNiven et al.
10,238,495 B2 3/2019 Marsot et al.
10,299,924 B2 5/2019 Kizuka
10,376,673 B2 8/2019 Van Hoven et al.
10,575,841 B1 3/2020 Paulos
2001/0005787 A1 6/2001 Oz et al.
2002/0013571 A1 1/2002 Goldfarb et al.
2002/0107531 A1 8/2002 Schreck et al.
2002/0173811 A1 11/2002 Tu et al.
2002/0183787 A1 12/2002 Wahr et al.
2003/0144573 A1 7/2003 Heilman et al.
2003/0187467 A1 10/2003 Schreck
2003/0208231 A1 11/2003 Williamson et al.
2004/0003819 A1 1/2004 St. Goar et al.
2004/0030382 A1 2/2004 St. Goar et al.
2004/0034365 A1 2/2004 Lentz et al.
2004/0044350 A1 3/2004 Martin et al.
2004/0044365 A1 3/2004 Bachman
2004/0049207 A1 3/2004 Goldfarb et al.
2004/0122448 A1 6/2004 Levine
2004/0127981 A1 7/2004 Rahdert et al.
2004/0127982 A1 7/2004 Machold et al.
2004/0147943 A1 7/2004 Kobayashi
2004/0181135 A1 9/2004 Drysen
2004/0181206 A1 9/2004 Chiu et al.
2004/0181238 A1 9/2004 Zarbatany et al.
2004/0210307 A1 10/2004 Khairkhahan
2004/0220593 A1 11/2004 Greenhalgh
2005/0010287 A1 1/2005 Macoviak et al.
2005/0049618 A1 3/2005 Masuda et al.
2005/0070926 A1 3/2005 Ortiz
2005/0137690 A1 6/2005 Salahieh et al.
2005/0143767 A1 6/2005 Kimura et al.
2005/0165429 A1 7/2005 Douglas et al.
2005/0216039 A1 9/2005 Lederman
2005/0251177 A1 11/2005 Saadat et al.
2005/0251183 A1 11/2005 Buckman et al.
2005/0288786 A1 12/2005 Chanduszko
2006/0020275 A1 1/2006 Goldfarb et al.
2006/0089671 A1 4/2006 Goldfarb et al.
2006/0100649 A1 5/2006 Hart
2006/0122647 A1 6/2006 Callaghan et al.
2006/0142694 A1 6/2006 Bednarek et al.
2006/0173251 A1 8/2006 Govari et al.
2006/0178700 A1 8/2006 Quinn
2006/0224169 A1 10/2006 Weisenburgh et al.
2007/0010800 A1 1/2007 Weitzner et al.
2007/0010877 A1 1/2007 Salahieh et al.
2007/0016286 A1 1/2007 Herrmann et al.
2007/0021779 A1 1/2007 Garvin et al.
2007/0032807 A1 2/2007 Ortiz et al.
2007/0093857 A1 4/2007 Rogers et al.
2007/0093890 A1 4/2007 Eliasen et al.
2007/0156197 A1 7/2007 Root et al.
2007/0191154 A1 8/2007 Genereux et al.
2007/0197858 A1* 8/2007 Goldfarb ................ A61B 17/08
600/37
2007/0198038 A1 8/2007 Cohen et al.
2007/0265700 A1 11/2007 Eliasen et al.
2007/0282414 A1 12/2007 Soltis et al.
2007/0293943 A1 12/2007 Quinn
2007/0299387 A1 12/2007 Williams et al.
2007/0299424 A1 12/2007 Cumming et al.
2008/0039743 A1 2/2008 Fox et al.
2008/0039953 A1 2/2008 Davis et al.
2008/0065149 A1 3/2008 Thielen et al.
2008/0077144 A1 3/2008 Crofford
2008/0091169 A1 4/2008 Heideman et al.
2008/0140089 A1 6/2008 Kogiso et al.
2008/0147093 A1 6/2008 Roskopf et al.
2008/0147112 A1 6/2008 Sheets et al.
2008/0149685 A1 6/2008 Smith et al.
2008/0167713 A1 7/2008 Bolling
2008/0177300 A1 7/2008 Mas et al.
2008/0208332 A1 8/2008 Lamphere et al.
2008/0221672 A1 9/2008 Lamphere et al.
2008/0255427 A1 10/2008 Satake et al.
2008/0281411 A1 11/2008 Berreklouw
2008/0287862 A1 11/2008 Weitzner et al.
2008/0294247 A1 11/2008 Yang et al.
2008/0312506 A1 12/2008 Spivey et al.
2008/0319455 A1 12/2008 Harris et al.
2009/0005863 A1 1/2009 Goetz et al.
2009/0024110 A1 1/2009 Heideman et al.
2009/0131880 A1 5/2009 Speziali et al.
2009/0156995 A1 6/2009 Martin et al.
2009/0163934 A1 6/2009 Raschdorf et al.
2009/0166913 A1 7/2009 Guo et al.
2009/0177266 A1 7/2009 Powell et al.
2009/0234280 A1 9/2009 Tah et al.
2009/0275902 A1 11/2009 Heeps et al.
2009/0287304 A1 11/2009 Dahlgren et al.
2010/0022823 A1 1/2010 Goldfarb et al.
2010/0036379 A1 2/2010 Prakash et al.
2010/0057192 A1 3/2010 Celermajer
2010/0069834 A1 3/2010 Schultz
2010/0094317 A1 4/2010 Goldfarb et al.
2010/0106141 A1 4/2010 Osypka et al.
2010/0121434 A1 5/2010 Paul et al.
2010/0249497 A1 9/2010 Peine et al.
2010/0298929 A1 11/2010 Thornton et al.
2010/0324595 A1 12/2010 Linder et al.
2011/0082538 A1 4/2011 Dahlgren et al.
2011/0137410 A1 6/2011 Hacohen
2011/0245855 A1 10/2011 Matsuoka et al.
2011/0257723 A1 10/2011 McNamara
2011/0295281 A1 12/2011 Mizumoto et al.
2012/0022633 A1 1/2012 Olson et al.
2012/0089125 A1 4/2012 Scheibe et al.
2012/0109160 A1 5/2012 Martinez et al.
2012/0116419 A1 5/2012 Sigmon
2012/0209318 A1 8/2012 Qadeer
2012/0277853 A1 11/2012 Rothstein
2012/0330351 A1 12/2012 Friedman et al.
2013/0035759 A1 2/2013 Gross et al.
2013/0041314 A1 2/2013 Dillon
2013/0066341 A1 3/2013 Ketai et al.
2013/0066342 A1 3/2013 Dell et al.
2013/0072945 A1 3/2013 Terada
2013/0073034 A1 3/2013 Wilson et al.
2013/0110254 A1 5/2013 Osborne
2013/0190798 A1 7/2013 Kapadia
2013/0190861 A1 7/2013 Chau et al.
2013/0268069 A1 10/2013 Zakai et al.
2013/0282059 A1 10/2013 Ketai et al.
2013/0304197 A1 11/2013 Buchbinder et al.
2013/0325110 A1 12/2013 Khalil et al.
2014/0031928 A1 1/2014 Murphy et al.
2014/0046433 A1 2/2014 Kovalsky
2014/0046434 A1 2/2014 Rolando et al.
2014/0052237 A1 2/2014 Lane et al.
2014/0058411 A1 2/2014 Soutorine et al.
2014/0067048 A1 3/2014 Chau et al.
2014/0067052 A1 3/2014 Chau et al.

(56) References Cited

U.S. PATENT DOCUMENTS

| | | | |
|---|---|---|---|
| 2014/0094903 | A1 | 4/2014 | Miller et al. |
| 2014/0135685 | A1 | 5/2014 | Kabe et al. |
| 2014/0194975 | A1 | 7/2014 | Quill et al. |
| 2014/0200662 | A1 | 7/2014 | Eftel et al. |
| 2014/0207231 | A1 | 7/2014 | Hacohen et al. |
| 2014/0222136 | A1 | 8/2014 | Geist et al. |
| 2014/0236198 | A1 | 8/2014 | Goldfarb et al. |
| 2014/0243968 | A1 | 8/2014 | Padala |
| 2014/0251042 | A1 | 9/2014 | Asselin et al. |
| 2014/0277404 | A1 | 9/2014 | Wilson et al. |
| 2014/0277411 | A1 | 9/2014 | Börtlein et al. |
| 2014/0277427 | A1 | 9/2014 | Ratz et al. |
| 2014/0316428 | A1 | 10/2014 | Golan |
| 2014/0324164 | A1 | 10/2014 | Gross et al. |
| 2014/0330368 | A1 | 11/2014 | Gloss et al. |
| 2014/0336751 | A1 | 11/2014 | Kramer |
| 2014/0371843 | A1 | 12/2014 | Wilson et al. |
| 2015/0039084 | A1 | 2/2015 | Levi et al. |
| 2015/0057704 | A1 | 2/2015 | Takahashi |
| 2015/0094802 | A1 | 4/2015 | Buchbinder et al. |
| 2015/0100116 | A1 | 4/2015 | Mohl et al. |
| 2015/0105808 | A1 | 4/2015 | Gordon et al. |
| 2015/0148896 | A1 | 5/2015 | Karapetian et al. |
| 2015/0157268 | A1 | 6/2015 | Winshtein et al. |
| 2015/0196390 | A1 | 7/2015 | Ma et al. |
| 2015/0223793 | A1 | 8/2015 | Goldfarb et al. |
| 2015/0230919 | A1 | 8/2015 | Chau et al. |
| 2015/0238313 | A1 | 8/2015 | Spence et al. |
| 2015/0257757 | A1 | 9/2015 | Powers et al. |
| 2015/0257877 | A1 | 9/2015 | Hernandez |
| 2015/0257883 | A1 | 9/2015 | Basude et al. |
| 2015/0272734 | A1 | 10/2015 | Sheps et al. |
| 2015/0313592 | A1 | 11/2015 | Coillard-Lavirotte et al. |
| 2015/0351904 | A1 | 12/2015 | Cooper et al. |
| 2015/0366666 | A1 | 12/2015 | Khairkhahan et al. |
| 2016/0008129 | A1 | 1/2016 | Siegel |
| 2016/0008131 | A1 | 1/2016 | Christianson et al. |
| 2016/0022970 | A1 | 1/2016 | Forcucci et al. |
| 2016/0051796 | A1 | 2/2016 | Kanemasa et al. |
| 2016/0074164 | A1 | 3/2016 | Naor |
| 2016/0074165 | A1 | 3/2016 | Spence et al. |
| 2016/0106539 | A1 | 4/2016 | Buchbinder et al. |
| 2016/0113762 | A1 | 4/2016 | Clague et al. |
| 2016/0113764 | A1 | 4/2016 | Sheahan et al. |
| 2016/0113766 | A1 | 4/2016 | Ganesan et al. |
| 2016/0155987 | A1 | 6/2016 | Yoo et al. |
| 2016/0174979 | A1 | 6/2016 | Wei |
| 2016/0174981 | A1 | 6/2016 | Fago et al. |
| 2016/0242906 | A1 | 8/2016 | Morriss et al. |
| 2016/0287387 | A1 | 10/2016 | Wei |
| 2016/0302811 | A1 | 10/2016 | Rodriguez-Navarro et al. |
| 2016/0317290 | A1 | 11/2016 | Chau et al. |
| 2016/0331523 | A1 | 11/2016 | Chau et al. |
| 2016/0354082 | A1 | 12/2016 | Oz et al. |
| 2017/0020521 | A1 | 1/2017 | Krone et al. |
| 2017/0035561 | A1 | 2/2017 | Rowe et al. |
| 2017/0035566 | A1 | 2/2017 | Krone et al. |
| 2017/0042456 | A1 | 2/2017 | Budiman |
| 2017/0042678 | A1 | 2/2017 | Ganesan et al. |
| 2017/0049455 | A1 | 2/2017 | Seguin |
| 2017/0100119 | A1 | 4/2017 | Baird et al. |
| 2017/0100236 | A1 | 4/2017 | Robertson et al. |
| 2017/0224955 | A1 | 8/2017 | Douglas et al. |
| 2017/0239048 | A1 | 8/2017 | Goldfarb et al. |
| 2017/0252154 | A1 | 9/2017 | Tubishevitz et al. |
| 2017/0266413 | A1 | 9/2017 | Khuu et al. |
| 2017/0281330 | A1 | 10/2017 | Liljegren et al. |
| 2017/0348102 | A1 | 12/2017 | Cousins et al. |
| 2018/0008311 | A1 | 1/2018 | Shiroff et al. |
| 2018/0008403 | A1 | 1/2018 | Freschauf et al. |
| 2018/0021044 | A1 | 1/2018 | Miller et al. |
| 2018/0021129 | A1 | 1/2018 | Peterson et al. |
| 2018/0021134 | A1 | 1/2018 | McNiven et al. |
| 2018/0071487 | A1 | 3/2018 | Khuu et al. |
| 2018/0078271 | A1 | 3/2018 | Thrasher |
| 2018/0078361 | A1 | 3/2018 | Naor et al. |
| 2018/0092661 | A1 | 4/2018 | Prabhu |
| 2018/0126124 | A1 | 5/2018 | Winston et al. |
| 2018/0133008 | A1 | 5/2018 | Kizuka et al. |
| 2018/0146964 | A1 | 5/2018 | Garcia et al. |
| 2018/0146966 | A1 | 5/2018 | Hernández et al. |
| 2018/0153552 | A1 | 6/2018 | King et al. |
| 2018/0161159 | A1 | 6/2018 | Lee et al. |
| 2018/0168803 | A1 | 6/2018 | Pesce et al. |
| 2018/0185154 | A1 | 7/2018 | Cao |
| 2018/0221147 | A1 | 8/2018 | Ganesan et al. |
| 2018/0235657 | A1 | 8/2018 | Abunassar |
| 2018/0243086 | A1 | 8/2018 | Barbarino et al. |
| 2018/0258665 | A1 | 9/2018 | Reddy et al. |
| 2018/0263767 | A1 | 9/2018 | Chau et al. |
| 2018/0296326 | A1 | 10/2018 | Dixon et al. |
| 2018/0296327 | A1 | 10/2018 | Dixon et al. |
| 2018/0296328 | A1 | 10/2018 | Dixon et al. |
| 2018/0296329 | A1 | 10/2018 | Dixon et al. |
| 2018/0296330 | A1 | 10/2018 | Dixon et al. |
| 2018/0296331 | A1 | 10/2018 | Dixon et al. |
| 2018/0296332 | A1 | 10/2018 | Dixon et al. |
| 2018/0296333 | A1 | 10/2018 | Dixon et al. |
| 2018/0296334 | A1 | 10/2018 | Dixon et al. |
| 2018/0325661 | A1 | 11/2018 | Delgado et al. |
| 2018/0325671 | A1 | 11/2018 | Abunassar et al. |
| 2018/0333259 | A1 | 11/2018 | Dibie |
| 2018/0344457 | A1 | 12/2018 | Gross et al. |
| 2018/0353181 | A1 | 12/2018 | Wei |
| 2018/0353182 | A1 | 12/2018 | Wei |
| 2019/0000613 | A1 | 1/2019 | Delgado et al. |
| 2019/0000623 | A1 | 1/2019 | Pan et al. |
| 2019/0008642 | A1 | 1/2019 | Delgado et al. |
| 2019/0008643 | A1 | 1/2019 | Delgado et al. |
| 2019/0015199 | A1 | 1/2019 | Delgado et al. |
| 2019/0015200 | A1 | 1/2019 | Delgado et al. |
| 2019/0015207 | A1 | 1/2019 | Delgado et al. |
| 2019/0015208 | A1 | 1/2019 | Delgado et al. |
| 2019/0021851 | A1 | 1/2019 | Delgado et al. |
| 2019/0021852 | A1 | 1/2019 | Delgado et al. |
| 2019/0029498 | A1 | 1/2019 | Mankowski et al. |
| 2019/0029810 | A1 | 1/2019 | Delgado et al. |
| 2019/0029813 | A1 | 1/2019 | Delgado et al. |
| 2019/0030285 | A1 | 1/2019 | Prabhu et al. |
| 2019/0053810 | A1 | 2/2019 | Griffin |
| 2019/0060058 | A1 | 2/2019 | Delgado et al. |
| 2019/0060059 | A1 | 2/2019 | Delgado et al. |
| 2019/0060072 | A1 | 2/2019 | Zeng |
| 2019/0060073 | A1 | 2/2019 | Delgado et al. |
| 2019/0060074 | A1 | 2/2019 | Delgado et al. |
| 2019/0060075 | A1 | 2/2019 | Delgado et al. |
| 2019/0069991 | A1 | 3/2019 | Metchik et al. |
| 2019/0069992 | A1 | 3/2019 | Delgado et al. |
| 2019/0069993 | A1 | 3/2019 | Delgado et al. |
| 2019/0105156 | A1 | 4/2019 | He et al. |
| 2019/0111239 | A1 | 4/2019 | Bolduc et al. |
| 2019/0117113 | A1 | 4/2019 | Curran |
| 2019/0142589 | A1 | 5/2019 | Basude |
| 2019/0159782 | A1 | 5/2019 | Kamaraj et al. |
| 2019/0167197 | A1 | 6/2019 | Abunassar et al. |
| 2019/0183644 | A1 | 6/2019 | Hacohen |
| 2019/0192296 | A1 | 6/2019 | Schwartz et al. |
| 2019/0209323 | A1 | 7/2019 | Metchik et al. |
| 2019/0261995 | A1 | 8/2019 | Goldfarb et al. |
| 2019/0261996 | A1 | 8/2019 | Goldfarb et al. |
| 2019/0261997 | A1 | 8/2019 | Goldfarb et al. |
| 2019/0314155 | A1 | 10/2019 | Franklin et al. |
| 2019/0321166 | A1 | 10/2019 | Freschauf et al. |
| 2020/0113683 | A1 | 4/2020 | Dale et al. |
| 2020/0138569 | A1 | 5/2020 | Basude et al. |
| 2020/0205979 | A1 | 7/2020 | O'Carroll et al. |
| 2020/0222185 | A1 | 7/2020 | Kappetein et al. |
| 2020/0237512 | A1 | 7/2020 | McCann et al. |
| 2020/0337842 | A1 | 10/2020 | Metchik et al. |
| 2020/0352717 | A1 | 11/2020 | Kheradvar et al. |
| 2020/0360054 | A1 | 11/2020 | Walsh et al. |
| 2020/0360132 | A1 | 11/2020 | Spence |
| 2020/0368016 | A1 | 11/2020 | Pesce et al. |
| 2021/0022850 | A1 | 1/2021 | Basude et al. |

(56) References Cited

U.S. PATENT DOCUMENTS

| | | | |
|---|---|---|---|
| 2021/0059680 | A1 | 3/2021 | Lin et al. |
| 2021/0169650 | A1 | 6/2021 | Dai et al. |
| 2021/0186698 | A1 | 6/2021 | Abunassar et al. |
| 2021/0251757 | A1 | 8/2021 | Siegel et al. |
| 2021/0259835 | A1 | 8/2021 | Tyler et al. |
| 2021/0267664 | A1 | 9/2021 | Lennartz et al. |
| 2021/0267781 | A1 | 9/2021 | Metchik et al. |
| 2021/0307900 | A1 | 10/2021 | Hacohen |
| 2021/0330456 | A1 | 10/2021 | Hacohen et al. |
| 2021/0338418 | A1 | 11/2021 | Feld |
| 2021/0361238 | A1 | 11/2021 | Bak-Boychuk et al. |
| 2021/0361416 | A1 | 11/2021 | Stearns |
| 2021/0361422 | A1 | 11/2021 | Gross et al. |
| 2021/0361428 | A1 | 11/2021 | Dixon |
| 2021/0378818 | A1 | 12/2021 | Manash et al. |
| 2021/0401434 | A1 | 12/2021 | Tien et al. |
| 2022/0039943 | A1 | 2/2022 | Phan |
| 2022/0039954 | A1 | 2/2022 | Nia et al. |
| 2022/0071767 | A1 | 3/2022 | Dixon et al. |
| 2022/0133327 | A1 | 5/2022 | Zhang et al. |
| 2022/0142780 | A1 | 5/2022 | Zhang et al. |
| 2022/0142781 | A1 | 5/2022 | Zhang et al. |
| 2022/0226108 | A1 | 7/2022 | Freschauf et al. |
| 2022/0233312 | A1 | 7/2022 | Delgado et al. |
| 2022/0257196 | A1 | 8/2022 | Massmann |
| 2022/0287841 | A1 | 9/2022 | Freschauf et al. |
| 2022/0296248 | A1 | 9/2022 | Abunassar et al. |
| 2022/0313433 | A1 | 10/2022 | Ma et al. |
| 2023/0014540 | A1 | 1/2023 | Metchik et al. |
| 2023/0149170 | A1 | 5/2023 | Giese et al. |
| 2023/0218291 | A1 | 7/2023 | Zarbatany et al. |
| 2023/0270549 | A1 | 8/2023 | Guidotti et al. |
| 2024/0148505 | A1 | 5/2024 | Datta et al. |
| 2024/0358514 | A1 | 10/2024 | Harush et al. |
| 2025/0073034 | A1 | 3/2025 | Abunassar et al. |

FOREIGN PATENT DOCUMENTS

| | | | |
|---|---|---|---|
| CN | 106491245 | A | 3/2017 |
| CN | 107789017 | A | 3/2018 |
| CN | 109953779 | A | 7/2019 |
| CN | 110338857 | A | 10/2019 |
| CN | 110495972 | A | 11/2019 |
| CN | 110537946 | A | 12/2019 |
| CN | 110664515 | A | 1/2020 |
| CN | 209996540 | U | 1/2020 |
| CN | 211243911 | U | 8/2020 |
| CN | 211723546 | U | 10/2020 |
| CN | 111870398 | A | 11/2020 |
| CN | 111904660 | A | 11/2020 |
| CN | 112120831 | A | 12/2020 |
| CN | 112168427 | A | 1/2021 |
| CN | 112190367 | A | 1/2021 |
| CN | 212346813 | U | 1/2021 |
| CN | 212415988 | U | 1/2021 |
| CN | 212490263 | U | 2/2021 |
| CN | 112741711 | A | 5/2021 |
| CN | 113476182 | A | 10/2021 |
| CN | 113855328 | A | 12/2021 |
| CN | 215019733 | U | 12/2021 |
| CN | 121154326 | A | 12/2025 |
| EP | 0098100 | A2 | 1/1984 |
| FR | 2768324 | B1 | 3/1999 |
| WO | 2014064694 | A2 | 5/2014 |
| WO | 2017015632 | A1 | 1/2017 |
| WO | 2018013856 | A1 | 1/2018 |
| WO | 2018050200 | A1 | 3/2018 |
| WO | 2018050203 | A1 | 3/2018 |
| WO | 2018195015 | A1 | 10/2018 |
| WO | 2018195201 | A1 | 10/2018 |
| WO | 2018195215 | A2 | 10/2018 |
| WO | 2019139904 | A1 | 7/2019 |
| WO | 2020106705 | A1 | 5/2020 |
| WO | 2020106827 | A1 | 5/2020 |
| WO | 2020112622 | A1 | 6/2020 |
| WO | 2020167677 | A1 | 8/2020 |
| WO | 2020168081 | A1 | 8/2020 |
| WO | 2020172224 | A1 | 8/2020 |
| WO | 2020176410 | A1 | 9/2020 |
| WO | 2021196580 | A1 | 10/2021 |
| WO | 2021227412 | A1 | 11/2021 |
| WO | 2022006087 | A2 | 1/2022 |
| WO | 2022036209 | A1 | 2/2022 |
| WO | 2022051241 | A1 | 3/2022 |
| WO | 2022052506 | A1 | 3/2022 |
| WO | 2022068188 | A1 | 4/2022 |
| WO | 2022101817 | A2 | 5/2022 |
| WO | 2022140175 | A1 | 6/2022 |
| WO | 2022153131 | A1 | 7/2022 |
| WO | 2022155298 | A2 | 7/2022 |
| WO | 2022157592 | A1 | 7/2022 |
| WO | 2022212172 | A1 | 10/2022 |
| WO | 2023003755 | A1 | 1/2023 |
| WO | 2023004098 | A1 | 1/2023 |
| WO | 2023278663 | A2 | 1/2023 |
| WO | 2023288003 | A1 | 1/2023 |
| WO | WO-2023001661 | A1 | 1/2023 |

OTHER PUBLICATIONS

Al-Khaja et al., "Eleven years' experience with Carpentier-Edwards biological valves in relation to survival and complications", European Journal of Cardio-Thoracic Surgery, vol. 3, No. 4, pp. 305-311, Jul. 1, 1989, Springer-Verlag, Berlin, Germany.

Almagor et al., "Balloon Expandable Stent Implantation in Stenotic Right Heart Valved Conduits", Journal of the American College of Cardiology, vol. 16, No. 5, pp. 1310-1314, Nov. 15, 1990.

Andersen, et al., "Transluminal implantation of artificial heart valves. Description of a new expandable aortic valve and initial results with implantation by catheter technique in closed chest pigs", European Heart Journal, vol. 13, No. 5, pp. 704-708, May 1, 1992, The European Society of Cardiology, Oxford University Press, United Kingdom.

Andersen, H.R. "History of Percutaneous Aortic Valve Prosthesis," Herz, vol. 34., No. 5, pp. 343-346, Aug. 2009, Urban&Vogel, Germany.

Batista RJ et al., "Partial left ventriculectomy to treat end-stage heart disease", Ann Thorac Surg., vol. 64, Issue—3, pp. 634-638, Sep. 1997.

Beall AC Jr. et al., "Clinical experience with a dacron velour-covered teflon-disc mitral-valve prosthesis", Ann Thorac Surg., vol. 5, Issue 5, pp. 402-410, May 1968.

Benchimol et al., "Simultaneous left ventricular echocardiography and aortic blood velocity during rapid right ventricular pacing in man", The American Journal of the Medical Sciences, vol. 273, No. 1, pp. 55-62, Jan.-Feb. 1977, Elsevier, United States.

Dake et al., "Transluminal Placement of Endovascular Stent-Grafts for the Treatment of Descending Thoracic Aortic Aneurysms", The New England Journal of Medicine, vol. 331, No. 26, pp. 1729-1734, Dec. 29, 1994.

Dotter et al., "Transluminal Treatment of Arteriosclerotic Obstruction: Description of a New Technic and a Preliminary Report of Its Application", Circulation, vol. XXX, No. 30, pp. 654-670, Nov. 1, 1964, Lippincott Williams&Wilkins, Philadelphia, PA.

Fucci et al., "Improved results with mitral valve repair using new surgical techniques", Eur J Cardiothorac Surg. 1995;Issue 9, vol. 11, pp. 621-626.

Inoune et al., "Clinical application of transvenous mitral commissurotomy by a new balloon catheter," The Journal of Thoracic and Cardiovascular Surgery, vol. 87, No. 3, pp. 394-402, Mar. 1984, Elsevier, United States.

Kolata, Gina "Device That Opens Clogged Arteries Gets a Failing Grade in a New Study", The New York Times, Jan. 3, 1991, pp. 1-2 [online], [retrieved on Jul. 29, 2009]. Retrieved from the Internet <URL:http://www.nytimes.com/1991/01/03/health/device-that-opens-clogged-arteries-gets-a-faili . . . .

Lawrence, Jr., et al., "Percutaneous Endovascular Graft: Experimental Evaluation", Cardiovascular Radiology 163, pp. 357-360, May 1987.

(56) References Cited

OTHER PUBLICATIONS

Maisano F et al., 'The edge-to-edge technique: a simplified method to correct mitral insufficiency', Eur J Cardiothorac Surg., vol. 13, Issue—3, pp. 240-245, Mar. 1998.
Pavcnik et al., "Development and Initial Experimental Evaluation of a Prosthetic Aortic Valve for Transcatheter Placement," Radiology, vol. 183, No. 1, pp. 151-154, Apr. 1, 1992. Elsevier, United States.
Porstmann et al., "Der Verschluß des Ductus Arteriosus Persistens Ohne Thorakotomie", Thoraxchirurgie Vaskuläre Chirurgie, Band 15, Heft 2, Stuttgart, im Apr. 1967, pp. 199-203.
Reul RM et al., "Mitral valve reconstruction for mitral insufficiency", Prog Cardiovasc Dis., vol. 39, Issue—6, May-Jun. 1997.
Rösch et al., "The Birth, Early Years and Future of Interventional Radiology," Journal of Vascular and Interventional Radiology, vol. 14, No. 7, pp. 841-853, Jul. 1, 2003, Elsevier, United States.
Sabbah et al., "Mechanical Factors in the Degeneration of Porcine Bioprosthetic Valves: An Overview", Journal of Cardiac Surgery, vol. 4, No. 4, pp. 302-309, Dec. 1989.
Selby et al., "Experience with New Retrieval Forceps for Foreign Body Removal in the Vascular, Urinary, and Biliary Systems", Radiology, vol. 176, No. 2, pp. 535-538, Jul. 31, 1990, Radiological Society of North America, Oak Brook, IL.
Serruys et al., "Stenting of coronary arteries. Are we the sorcerer's apprentice?", European Heart Journal, vol. 10, No. 9 pp. 774-782, Sep. 1, 1989, The European Society of Cardiology, Oxford University Press, United Kingdom.
Sigwart, Ulrich, "An Overview of Intravascular Stents: Old and New," Textbook of Interventional Cardiology, Second Edition, chapter 48, pp. 803-815, © 1994, W.B. Saunders Company, Philadelphia, PA.
Uchida et al., "Modifications of Gianturco Expandable Wire Stents", Technical Note, American Roentgen Ray Society, pp. 1185-1187, May 1988.
Umaña JP et al., "'Bow-tie' mitral valve repair: an adjuvant technique for ischemic mitral regurgitation', Ann Thorac Surg., vol. 66, Issue—6, pp. 1640-1646, Nov. 1998.
Urban, Philip MD, "Coronary Artery Stenting", pp. 5-47, © 1991, ISBN: 2-88049-054-5, Editions Medecine et Hygiene, Geneva, Switzerland.
Watt et al., "Intravenous adenosine in the treatment of supraventricular rachycardia: a dose-ranging study and interaction with dipyridamole", British Journal of Clinical Pharmacology, vol. 21, No. 2, pp. 227-230, Feb. 1986, British Pharmacological Society, London, United Kingdom.
Wheatley, David J., "Valve Prosthesis", Rob&Smith's Operative Surgery—Cardiac Surgery, vol. 91, No. 2, pp. 415-424, Feb. 1, 1987, Butterworth Scientific, London, UK.
Praz et al., "Compassionate use of the PASCAL transcatheter mitral valve repair system for patients with severe mitral regurgitation: a multicentre, prospective, observational, first-in-man study," The Lancet, vol. 390, Issue 10096, pp. 773-780, Aug. 19, 2017, Lancet, United States.
Grasso et al., "The PASCAL transcatheter mitral valve repair system for the treatment of mitral regurgitation: another piece to the puzzle of edge-to-edge technique", Journal of Thoracic Disease, vol. 9, No. 12, pp. 4856-4859, Dec. 2017, doi:10.21037/jtd.2017.10.156, AME Publishing Company, Hong Kong, China.
Ross, D.N, "Aortic Valve Surgery", Surgery of the Aortic Valves, Guy's Hospital, London, pp. 192-197 [Removed Per Bim on Oct. 9, 2020].
Rashkind et al., "Historical Aspects of Interventional Cardiology: Past, Present, and Future", vol. 13, No. 4, pp. 363-367, Dec. 1986, Texas Heart Institute Journal, Interventional Cardiology, Houston, TX. [Dec. 22, 2020].
Rashkind et al., "Creation of an Atrial Septal Defect Without Thoracotomy: A Pallative Approach to Complete Transposition of the Great Arteries", The Journal of the American Medical Association, vol. 196, No. 11, pp. 173-174, Jun. 13, 1966 [Dec. 22, 2020].

* cited by examiner

VALVE REPAIR IMPLANT WITH LEAFLET TENSION INDICATION

RELATED APPLICATIONS

The present application is a continuation of Patent Cooperation Treaty Application PCT/US2021/045930, filed on Aug. 13, 2021, which claims the benefit of U.S. Provisional Application Ser. No. 63/066,097, filed on Aug. 14, 2020, which is incorporated herein by reference in its entirety for all purposes.

BACKGROUND

The native heart valves (i.e., the aortic, pulmonary, tricuspid, and mitral valves) serve critical functions in assuring the forward flow of an adequate supply of blood through the cardiovascular system. These heart valves can be damaged, and thus rendered less effective, for example, by congenital malformations, inflammatory processes, infectious conditions, disease, etc. Such damage to the valves can result in serious cardiovascular compromise or death. Damaged valves can be surgically repaired or replaced during open heart surgery. However, open heart surgeries are highly invasive, and complications may occur. Transvascular techniques can be used to introduce and implant prosthetic devices in a manner that is much less invasive than open heart surgery. As one example, a transvascular technique useable for accessing the native mitral and aortic valves is the trans-septal technique. The trans-septal technique comprises advancing a catheter into the right atrium (e.g., inserting a catheter into the right femoral vein, up the inferior vena cava and into the right atrium). The septum is then punctured, and the catheter passed into the left atrium. A similar transvascular technique can be used to implant a prosthetic device within the tricuspid valve that begins similarly to the trans-septal technique but stops short of puncturing the septum and instead turns the delivery catheter toward the tricuspid valve in the right atrium.

A healthy heart has a generally conical shape that tapers to a lower apex. The heart is four-chambered and comprises the left atrium, right atrium, left ventricle, and right ventricle. The left and right sides of the heart are separated by a wall generally referred to as the septum. The native mitral valve of the human heart connects the left atrium to the left ventricle. The mitral valve has a very different anatomy than other native heart valves. The mitral valve includes an annulus portion, which is an annular portion of the native valve tissue surrounding the mitral valve orifice, and a pair of cusps, or leaflets, extending downward from the annulus into the left ventricle. The mitral valve annulus can form a "D"-shaped, oval, or otherwise out-of-round cross-sectional shape having major and minor axes. The anterior leaflet can be larger than the posterior leaflet, forming a generally "C"-shaped boundary between the abutting sides of the leaflets when they are closed together.

When operating properly, the anterior leaflet and the posterior leaflet function together as a one-way valve to allow blood to flow only from the left atrium to the left ventricle. The left atrium receives oxygenated blood from the pulmonary veins. When the muscles of the left atrium contract and the left ventricle dilates (also referred to as "ventricular diastole" or "diastole"), the oxygenated blood that is collected in the left atrium flows into the left ventricle. When the muscles of the left atrium relax and the muscles of the left ventricle contract (also referred to as "ventricular systole" or "systole"), the increased blood pressure in the left ventricle urges the sides of the two leaflets together, thereby closing the one-way mitral valve so that blood cannot flow back to the left atrium and is instead expelled out of the left ventricle through the aortic valve. To prevent the two leaflets from prolapsing under pressure and folding back through the mitral annulus toward the left atrium, a plurality of fibrous cords called chordae tendineae tether the leaflets to papillary muscles in the left ventricle.

Valvular regurgitation involves the valve improperly allowing some blood to flow in the wrong direction through the valve. For example, mitral regurgitation occurs when the native mitral valve fails to close properly and blood flows into the left atrium from the left ventricle during the systolic phase of heart contraction. Mitral regurgitation is one of the most common forms of valvular heart disease. Mitral regurgitation can have many different causes, such as leaflet prolapse, dysfunctional papillary muscles, stretching of the mitral valve annulus resulting from dilation of the left ventricle, more than one of these, etc. Mitral regurgitation at a central portion of the leaflets can be referred to as central jet mitral regurgitation and mitral regurgitation nearer to one commissure (i.e., location where the leaflets meet) of the leaflets can be referred to as eccentric jet mitral regurgitation. Central jet regurgitation occurs when the edges of the leaflets do not meet in the middle and thus the valve does not close, and regurgitation is present. Tricuspid regurgitation can be similar, but on the right side of the heart.

SUMMARY

This summary is meant to provide some examples and is not intended to be limiting of the scope of the invention in any way. For example, any feature included in an example of this summary is not required by the claims, unless the claims explicitly recite the features. Also, the features, components, steps, concepts, etc. described in examples in this summary and elsewhere in this disclosure can be combined in a variety of ways. Various features and steps as described elsewhere in this disclosure may be included in the examples summarized here.

In some implementations, an implantable device or implant includes an anchor portion having one or more anchors configured to attach to one or more leaflets of the native heart valve. The anchors are moveable between an open and closed position. The implantable device or implant has an indication feature that is movable between an allowable tension position and an exceeded tension position. When the anchors are attached to the leaflets of the native heart valve the indication feature indicates to a user that an amount of force applied to the implantable device or implant by the leaflets (and vice versa) of the native heart valve exceeds a pre-set or predetermined amount of force by the indication feature being in the exceeded tension position. The indication feature can provide this tension indication when the device is in the open position, when the device is in a partially open position, and/or when the device is in a closed position.

In some implementations, an implantable device or implant includes an anchor portion comprising one or more anchors coupled to the actuation element. The anchors are configured to attach to one or more leaflets of a native heart valve. The anchors are configured to move between an open position and a closed position by movement of the actuation element. At least one of the actuation element and the anchor portion have an indication feature that is movable between an allowable tension position and an exceeded tension position. When the anchors are attached to the leaflets of the native heart valve, the indication feature indicates to a user when an amount of force applied to the anchor portion by the leaflets of the native heart valve exceeds a pre-set or predetermined amount of force.

In some implementations, an implantable device or implant includes a coaptation portion having a coaptation element, a distal portion having a cap that is movable relative to the coaptation element, and an anchor portion having one or more anchors coupled to the coaptation element and the cap. The anchors are configured to attach to one or more leaflets of the native heart valve and to move between an open and closed position by movement of the cap relative to the coaptation element. At least one of the coaptation portion, distal portion, and anchor portion have an indication feature that is movable between an allowable tension position and an exceeded tension position. When the anchors are attached to the leaflets of the native heart valve and in the closed position, the indication feature indicates to a user that an amount of force applied to the implantable device or implant by the leaflets of the native heart valve exceeds a pre-set or predetermined amount of force by the indication feature being in the exceeded tension position.

In some implementations, a valve repair device, comprises an anchor portion and an indication feature (e.g., tension indication feature). The anchor portion can comprise one or more anchors configured to attach to one or more leaflets of a native heart valve. The anchors can be configured to move between an open position and a closed position. The indication feature can be configured to, when the anchors are attached to the leaflets of the native heart valve, indicate when an amount of force applied to the device and/or anchor portion by the leaflets of the native heart valve exceeds a pre-set or predetermined amount of force and/or indicate when a predetermined tension on the device and/or anchor portion is exceeded.

The valve repair device can include any of the features or components of any of the devices or implants described anywhere herein.

The valve repair device can include a variety of different mechanisms or combinations of mechanisms for causing the anchors to transition between the open position and the closed position. For example, in some implementations, the device includes an actuation element that can be the same as or similar to any of the actuation elements described elsewhere herein. In some implementations, the device can include a gear mechanism, cam mechanism, worm screw, articulating joints, scissor-like mechanism, a combination of more than one of these, etc. that help to transition the anchors between the open and closed positions, In some implementations, the anchor portion and/or the anchors comprise one or more clasps. The clasps can also be configured to move or transition between an open configuration and a closed configuration, e.g., using an actuation line, etc. The clasps can be the same as or similar to other clasps described herein.

In some implementations, the one or more clasps comprise the indication feature.

In some implementations, at least a portion of the one or more clasps comprises a fixed arm that is attached to the anchor and a movable arm that is pivotally connected to the fixed arm, wherein the indication feature comprises a flexible material of the movable arm that allows the movable arm to be in a non-extended position when the indication feature is in a first tension position and an extended position when the indication feature is in a second tension position, the second tension position indicating to the user when the amount of force exceeds the predetermined amount of force and/or predetermined tension.

In some implementations, the one or more clasps comprise a first portion that includes a first visual marking of the indication feature and a second portion that includes a second visual marking of the indication feature, and wherein the second portion of the clasp is movable relative to the first portion such that movement of the second portion causes the second visual marking to move relative to the first visual marking to cause the indication feature to indicate to a user that the amount of force applied to the anchor portion by the leaflets of the native heart valve exceeds the predetermined amount of force and/or predetermined tension.

In some implementations, the indication feature comprises the components, configuration, and/or design of the device and/or of the anchors that allows the anchors to be in a non-extended position when the indication feature is in a first tension position (e.g., an allowable tension position or position where the predetermined amount of force and/or predetermined tension limit or optimal force/tension range has not been exceeded) and an extended position when the indication feature is in a second tension position (e.g., an exceeded tension position or position where the predetermined amount of force and/or predetermined tension limit or optimal force/tension range has been exceeded).

In some implementations, at least a portion of the one or more clasps comprises a fixed arm that is attached to the anchor at a connection point and a movable arm that is pivotally connected to the fixed arm at a pivotal connection point, wherein the connection point is a distance away from the pivotal connection point.

In some implementations, the indication feature comprises the attachment between the fixed arm at the connection point that allows at least a portion of the fixed arm to flex relative to the connection point when the indication feature is in the second tension position, and wherein the second tension position indicates the predetermined amount of force or predetermined tension has been exceeded.

In some implementations, the indication feature comprises a flexible material of the anchors, wherein the indication feature is in the second tension position when the flexible material of the anchors causes the anchors to flex away from a center of the device (e.g., a central axis, a coaptation element, and/or some other central component) when the anchors are connected to the leaflets of the native heart valve and in the closed position.

In some implementations, an actuation element for transitioning the anchors between the open position and the closed position extends through a catheter, and the indication feature comprises a visible portion of the actuation element that extends proximally of a proximal end of the catheter. In some implementations, the visible portion can be inside of a catheter handle at the proximal end of the catheter.

In some implementations, the indication feature comprises a flexible portion of the actuation element that allows the actuation element to bend.

In some implementations, the device further comprises a connection element that is movable from an unlocked stated to a locked state, and wherein the connection element attaches to the anchors to lock the anchors in the closed position when the connection element is in the locked state. The connection element can be the same as or similar to other connection elements described herein or otherwise known.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

To further clarify various aspects of implementations of the present disclosure, a more particular description of the certain examples and implementations will be made by reference to various aspects of the appended drawings. These drawings depict only example implementations of the present disclosure and are therefore not to be considered limiting of the scope of the disclosure. Moreover, while the FIGS. can be drawn to scale for some examples, the FIGS. are not necessarily drawn to scale for all examples. Examples and other features and advantages of the present disclosure will be described and explained with additional specificity and detail through the use of the accompanying drawings in which.

DETAILED DESCRIPTION

The following description refers to the accompanying drawings, which illustrate example implementations of the present disclosure. Some implementations having different structures and operation do not depart from the scope of the present disclosure.

Example implementations of the present disclosure are directed to systems, devices, methods, etc. for repairing a defective heart valve. For example, various implementations of implantable devices, valve repair devices, implants, and systems (including systems for delivery thereof) are disclosed herein, and any combination of these options can be made unless specifically excluded. In other words, individual components of the disclosed devices and systems can be combined unless mutually exclusive or otherwise physically impossible. Further, the techniques and methods herein can be performed on a living animal or on a simulation, such as on a cadaver, cadaver heart, simulator (e.g., with the body parts, heart, tissue, etc. being simulated), etc.

As described herein, when one or more components are described as being connected, joined, affixed, coupled, attached, or otherwise interconnected, such interconnection can be direct as between the components or can be indirect such as through the use of one or more intermediary components. Also as described herein, reference to a "member," "component," or "portion" shall not be limited to a single structural member, component, or element but can include an assembly of components, members, or elements. Also as described herein, the terms "substantially" and "about" are defined as at least close to (and includes) a given value or state (preferably within 10% of, more preferably within 1% of, and most preferably within 0.1% of).

Figure 1:
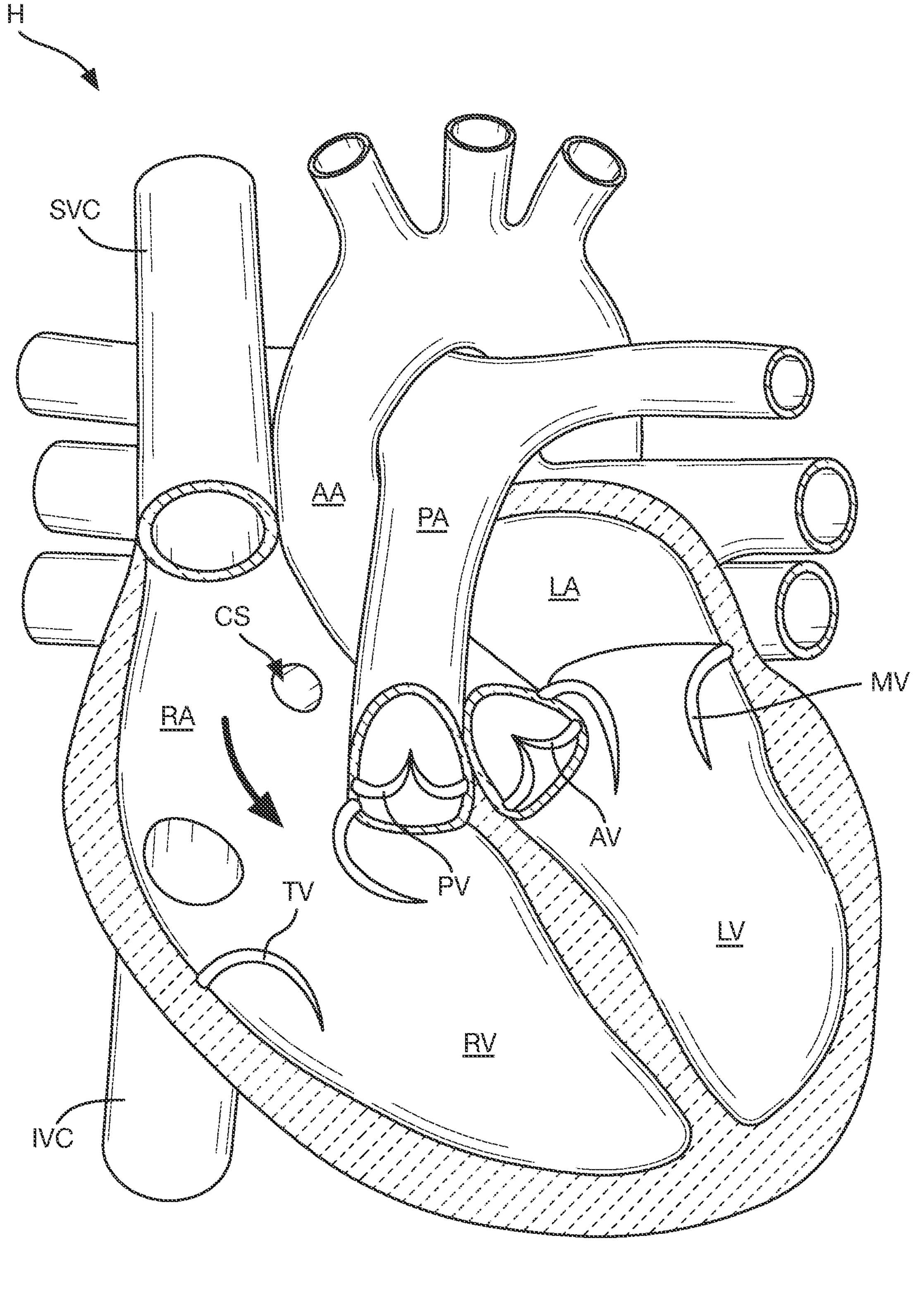
FIG. 1 illustrates a cutaway view of the human heart in a diastolic phase.
Figure 2:
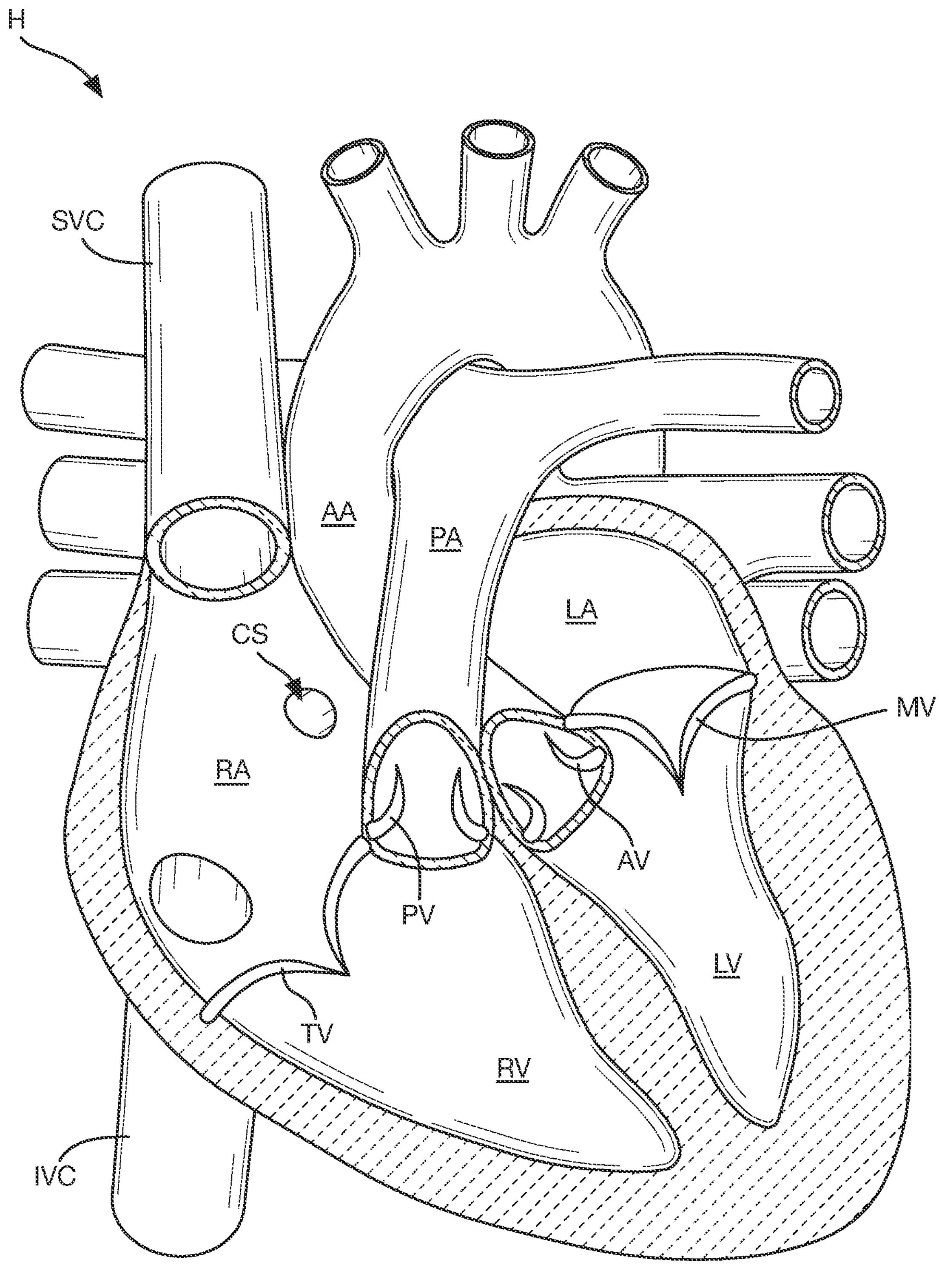
FIG. 2 illustrates a cutaway view of the human heart in a systolic phase.

FIGS. 1 and 2 are cutaway views of the human heart H in diastolic and systolic phases, respectively. The right ventricle RV and left ventricle LV are separated from the right atrium RA and left atrium LA, respectively, by the tricuspid valve TV and mitral valve MV; i.e., the atrioventricular valves. Additionally, the aortic valve AV separates the left ventricle LV from the ascending aorta AA, and the pulmonary valve PV separates the right ventricle from the pulmonary artery PA. Each of these valves has flexible leaflets (e.g., leaflets 20, 22 shown in FIGS. 3-6 and leaflets 30, 32, 34 shown in FIG. 7) extending inward across the respective orifices that come together or "coapt" in the flow stream to form the one-way, fluid-occluding surfaces. The native valve repair systems of the present application are frequently described and/or illustrated with respect to the mitral valve MV. Therefore, anatomical structures of the left atrium LA and left ventricle LV will be explained in greater detail. However, the devices described herein can also be used in repairing other native valves, e.g., the devices can be used in repairing the tricuspid valve TV, the aortic valve AV, and the pulmonary valve PV.

The left atrium LA receives oxygenated blood from the lungs. During the diastolic phase, or diastole, seen in FIG. 1, the blood that was previously collected in the left atrium LA (during the systolic phase) moves through the mitral valve MV and into the left ventricle LV by expansion of the left ventricle LV. In the systolic phase, or systole, seen in FIG. 2, the left ventricle LV contracts to force the blood through the aortic valve AV and ascending aorta AA into the body. During systole, the leaflets of the mitral valve MV close to prevent the blood from regurgitating from the left ventricle LV and back into the left atrium LA and blood is collected in the left atrium from the pulmonary vein. In some implementations, the devices described by the present application are used to repair the function of a defective mitral valve MV. That is, the devices are configured to help close the leaflets of the mitral valve to prevent blood from regurgitating from the left ventricle LV and back into the left atrium LA. Many of the devices described in the present application are designed to easily grasp and secure the native leaflets around a coaptation element or spacer that beneficially acts as a filler in the regurgitant orifice to prevent or inhibit back flow or regurgitation during systole, though this is not necessary.

Figure 3:
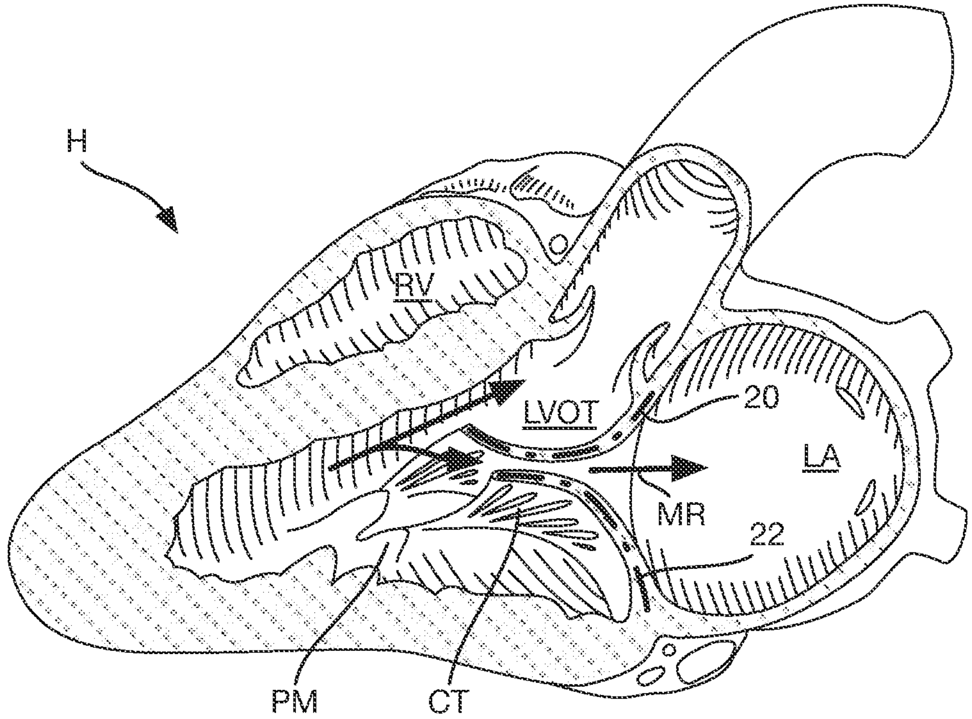
FIG. 3 illustrates a cutaway view of the human heart in a systolic phase showing mitral regurgitation.
Figure 4:
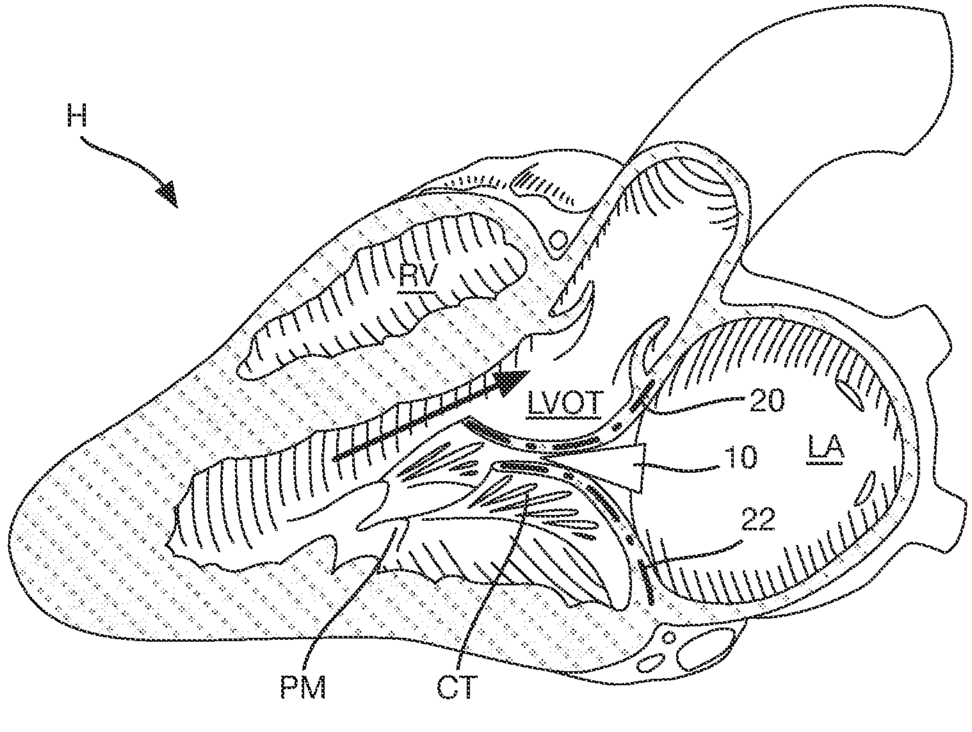
FIG. 4 is the cutaway view of FIG. 3 annotated to illustrate a natural shape of mitral valve leaflets in the systolic phase.

Referring now to FIGS. 1-7, the mitral valve MV includes two leaflets, the anterior leaflet 20 and the posterior leaflet 22. The mitral valve MV also includes an annulus 24, which is a variably dense fibrous ring of tissues that encircles the leaflets 20, 22. Referring to FIGS. 3 and 4, the mitral valve MV is anchored to the wall of the left ventricle LV by chordae tendineae CT. The chordae tendineae CT are cord-like tendons that connect the papillary muscles PM (i.e., the muscles located at the base of the chordae tendineae CT and within the walls of the left ventricle LV) to the leaflets 20, 22 of the mitral valve MV. The papillary muscles PM serve to limit the movements of leaflets 20, 22 of the mitral valve MV and prevent the mitral valve MV from being reverted. The mitral valve MV opens and closes in response to pressure changes in the left atrium LA and the left ventricle LV. The papillary muscles PM do not open or close the mitral valve MV. Rather, the papillary muscles PM support or brace the leaflets 20, 22 against the high pressure needed to circulate blood throughout the body. Together the papillary muscles PM and the chordae tendineae CT are known as the subvalvular apparatus, which functions to keep the mitral valve MV from prolapsing into the left atrium LA when the mitral valve closes. As seen from a Left Ventricular Outflow Tract (LVOT) view shown in FIG. 3, the anatomy of the leaflets 20, 22 is such that the inner sides of the leaflets coapt at the free end portions and the leaflets 20, 22 start receding or spreading apart from each other. The leaflets 20, 22 spread apart in the atrial direction, until each leaflet meets with the mitral annulus.

Various disease processes can impair proper function of one or more of the native valves of the heart H. These disease processes include degenerative processes (e.g., Barlow's Disease, fibroelastic deficiency, etc.), inflammatory processes (e.g., Rheumatic Heart Disease), and infectious processes (e.g., endocarditis, etc.). In addition, damage to the left ventricle LV or the right ventricle RV from prior heart attacks (i.e., myocardial infarction secondary to coronary artery disease) or other heart diseases (e.g., cardiomyopathy, etc.) can distort a native valve's geometry, which can cause the native valve to dysfunction. However, the majority of patients undergoing valve surgery, such as surgery to the mitral valve MV, suffer from a degenerative disease that causes a malfunction in a leaflet (e.g., leaflets 20, 22) of a native valve (e.g., the mitral valve MV), which results in prolapse and regurgitation.

Generally, a native valve may malfunction in different ways: including (1) valve stenosis; and (2) valve regurgitation. Valve stenosis occurs when a native valve does not open completely and thereby causes an obstruction of blood flow. Typically, valve stenosis results from buildup of calcified material on the leaflets of a valve, which causes the leaflets to thicken and impairs the ability of the valve to fully open to permit forward blood flow. Valve regurgitation occurs when the leaflets of the valve do not close completely thereby causing blood to leak back into the prior chamber (e.g., causing blood to leak from the left ventricle to the left atrium).

There are three main mechanisms by which a native valve becomes regurgitant—or incompetent—which include Carpentier's type I, type II, and type III malfunctions. A Carpentier type I malfunction involves the dilation of the annulus such that normally functioning leaflets are distracted from each other and fail to form a tight seal (i.e., the leaflets do not coapt properly). Included in a type I mechanism malfunction are perforations of the leaflets, as are present in endocarditis. A Carpentier's type II malfunction involves prolapse of one or more leaflets of a native valve above a plane of coaptation. A Carpentier's type III malfunction involves restriction of the motion of one or more leaflets of a native valve such that the leaflets are abnormally constrained below the plane of the annulus. Leaflet restriction can be caused by rheumatic disease (Ma) or dilation of a ventricle (IIIb).

Figure 5:
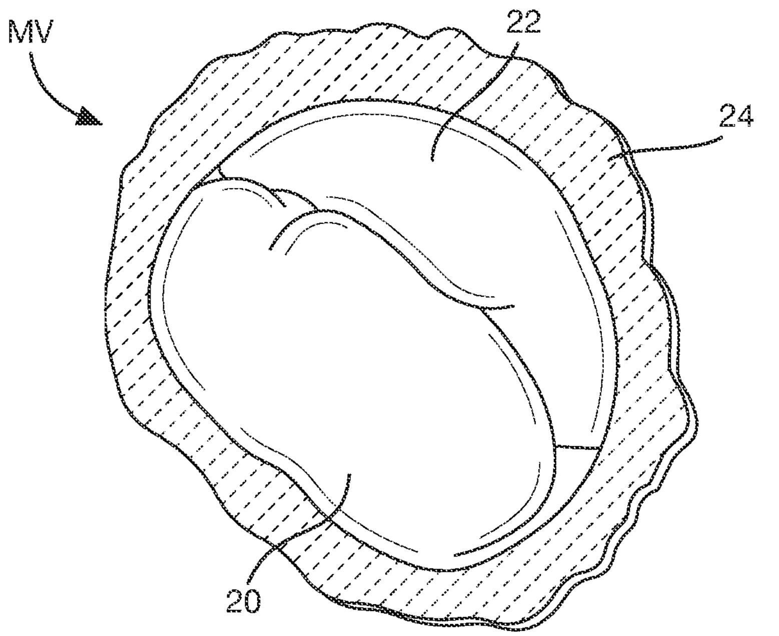
FIG. 5 illustrates a healthy mitral valve with the leaflets closed as viewed from an atrial side of the mitral valve.
Figure 6:
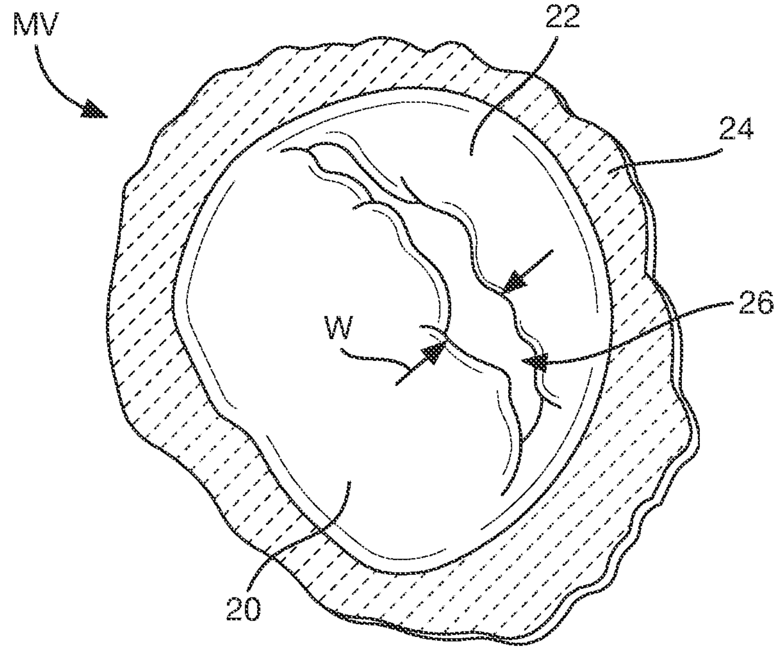
FIG. 6 illustrates a dysfunctional mitral valve with a visible gap between the leaflets as viewed from an atrial side of the mitral valve.
Figure 7:
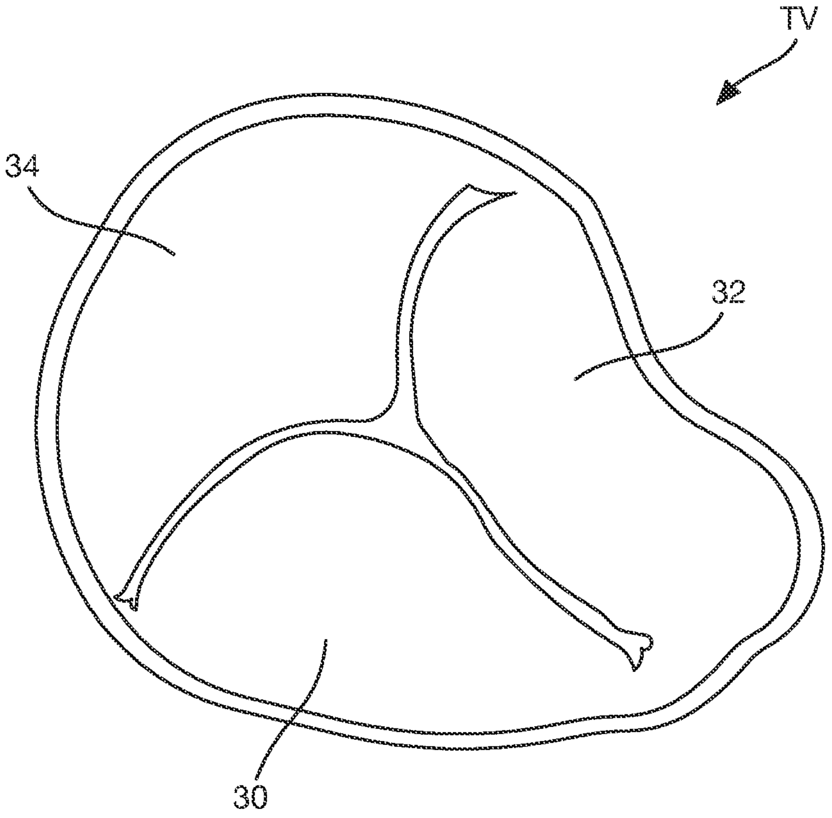
FIG. 7 illustrates a tricuspid valve viewed from an atrial side of the tricuspid valve.

Referring to FIG. 5, when a healthy mitral valve MV is in a closed position, the anterior leaflet 20 and the posterior leaflet 22 coapt, which prevents blood from leaking from the left ventricle LV to the left atrium LA. Referring to FIGS. 3 and 6, mitral regurgitation MR occurs when the anterior leaflet 20 and/or the posterior leaflet 22 of the mitral valve MV is displaced into the left atrium LA during systole so that the edges of the leaflets 20, 22 are not in contact with each other. This failure to coapt causes a gap 26 between the anterior leaflet 20 and the posterior leaflet 22, which allows blood to flow back into the left atrium LA from the left ventricle LV during systole, as illustrated by the mitral regurgitation MR flow path shown in FIG. 3. Referring to FIG. 6, the gap 26 can have a width W between about 2.5 mm and about 17.5 mm, between about 5 mm and about 15 mm, between about 7.5 mm and about 12.5 mm, or about 10 mm. In some situations, the gap 26 can have a width W greater than 15 mm. As set forth above, there are several different ways that a leaflet (e.g., leaflets 20, 22 of mitral valve MV) may malfunction which can thereby lead to valvular regurgitation.

In any of the above-mentioned situations, a valve repair device or implant is desired that is capable of engaging the anterior leaflet 20 and the posterior leaflet 22 to close the gap 26 and prevent regurgitation of blood through the mitral valve MV. As can be seen in FIG. 4, an abstract representation of an implantable device, valve repair device, or implant 10 is shown implanted between the leaflets 20, 22 such that regurgitation does not occur during systole (compare FIG. 3 with FIG. 4). In some implementations, the coaptation element (e.g., spacer, coaption element, gap filler, etc.) of the device 10 has a generally tapered or triangular shape that naturally adapts to the native valve geometry and to its expanding leaflet nature (toward the annulus). In this application, the terms spacer, coaption element, coaptation element, and gap filler are used interchangeably and refer to an element that fills a portion of the space between native valve leaflets and/or that is configured such that the native valve leaflets engage or "coapt" against (e.g., such that the native leaflets coapt against the coaption element, coaptation element, spacer, etc. instead of only against one another).).

Although stenosis or regurgitation can affect any valve, stenosis is predominantly found to affect either the aortic valve AV or the pulmonary valve PV, and regurgitation is predominantly found to affect either the mitral valve MV or the tricuspid valve TV Both valve stenosis and valve regurgitation increase the workload of the heart H and may lead to very serious conditions if left un-treated; such as endocarditis, congestive heart failure, permanent heart damage, cardiac arrest, and ultimately death. Because the left side of the heart (i.e., the left atrium LA, the left ventricle LV, the mitral valve MV, and the aortic valve AV) are primarily responsible for circulating the flow of blood throughout the body. Accordingly, because of the substantially higher pressures on the left side heart dysfunction of the mitral valve MV or the aortic valve AV is particularly problematic and often life threatening.

Malfunctioning native heart valves may either be repaired or replaced. Repair typically involves the preservation and correction of the patient's native valve. Replacement typically involves replacing the patient's native valve with a biological or mechanical substitute. Typically, the aortic valve AV and pulmonary valve PV are more prone to stenosis. Because stenotic damage sustained by the leaflets is irreversible, treatments for a stenotic aortic valve or stenotic pulmonary valve can be removal and replacement of the valve with a surgically implanted heart valve, or displacement of the valve with a transcatheter heart valve. The mitral valve MV and the tricuspid valve TV are more prone to deformation of leaflets and/or surrounding tissue, which, as described above, prevents the mitral valve MV or tricuspid valve TV from closing properly and allows for regurgitation or back flow of blood from the ventricle into the atrium (e.g., a deformed mitral valve MV may allow for regurgitation or back flow from the left ventricle LV to the left atrium LA as shown in FIG. 3). The regurgitation or back flow of blood from the ventricle to the atrium results in valvular insufficiency. Deformations in the structure or shape of the mitral valve MV or the tricuspid valve TV are often repairable. In addition, regurgitation can occur due to the chordae tendineae CT becoming dysfunctional (e.g., the chordae tendineae CT may stretch or rupture), which allows the anterior leaflet 20 and the posterior leaflet 22 to be reverted such that blood is regurgitated into the left atrium LA. The problems occurring due to dysfunctional chordae tendineae CT can be repaired by repairing the chordae tendineae CT or the structure of the mitral valve MV (e.g., by securing the leaflets 20, 22 at the affected portion of the mitral valve).

The devices and procedures disclosed herein often make reference to repairing the structure of a mitral valve. However, it should be understood that the devices and concepts provided herein can be used to repair any native valve, as well as any component of a native valve. Such devices can be used between the leaflets 20, 22 of the mitral valve MV to prevent or inhibit regurgitation of blood from the left ventricle into the left atrium. With respect to the tricuspid valve TV (FIG. 7), any of the devices and concepts herein can be used between any two of the anterior leaflet 30, septal leaflet 32, and posterior leaflet 34 to prevent or inhibit regurgitation of blood from the right ventricle into the right atrium. In addition, any of the devices and concepts provided herein can be used on all three of the leaflets 30, 32, 34 together to prevent or inhibit regurgitation of blood from the right ventricle to the right atrium. That is, the valve repair devices or implants provided herein can be centrally located between the three leaflets 30, 32, 34.

An example implantable device (e.g., implantable device, etc.) or implant can optionally have a coaptation element (e.g., spacer, coaption element, gap filler, etc.) and at least one anchor (e.g., one, two, three, or more). In some implementations, an implantable device or implant can have any combination or sub-combination of the features disclosed herein without a coaptation element. When included, the coaptation element (e.g., coaption element, spacer, etc.) is configured to be positioned within the native heart valve orifice to help fill the space between the leaflets and form a more effective seal, thereby reducing or preventing regurgitation described above. The coaptation element can have a structure that is impervious to blood (or that resists blood flow therethrough) and that allows the native leaflets to close around the coaptation element during ventricular systole to block blood from flowing from the left or right ventricle back into the left or right atrium, respectively. The device or implant can be configured to seal against two or three native valve leaflets; that is, the device may be used in the native mitral (bicuspid) and tricuspid valves. The coaptation element is sometimes referred to herein as a spacer because the coaptation element can fill a space between improperly functioning native leaflets (e.g., mitral leaflets 20, 22 or tricuspid leaflets 30, 32, 34) that do not close completely.

The optional coaptation element (e.g., spacer, coaption element, etc.) can have various shapes. In some implementations, the coaptation element can have an elongated cylindrical shape having a round cross-sectional shape. In some implementations, the coaptation element can have an oval cross-sectional shape, an ovoid cross-sectional shape, a crescent cross-sectional shape, a rectangular cross-sectional shape, or various other non-cylindrical shapes. In some implementations, the coaptation element can have an atrial portion positioned in or adjacent to the atrium, a ventricular or lower portion positioned in or adjacent to the ventricle, and a side surface that extends between the native leaflets. In some implementations configured for use in the tricuspid valve, the atrial or upper portion is positioned in or adjacent to the right atrium, and the ventricular or lower portion is positioned in or adjacent to the right ventricle, and the side surface that extends between the native tricuspid leaflets.

In some implementations, the anchor can be configured to secure the device to one or both of the native leaflets such that the coaptation element is positioned between the two native leaflets. In some implementations configured for use in the tricuspid valve, the anchor is configured to secure the device to one, two, or three of the tricuspid leaflets such that the coaptation element is positioned between the three native leaflets. In some implementations, the anchor can attach to the coaptation element at a location adjacent the ventricular portion of the coaptation element. In some implementations, the anchor can attach to an actuation element, such as a shaft or actuation wire, to which the coaptation element is also attached.

In some implementations, the anchor and the coaptation element can be positioned independently with respect to each other by separately moving each of the anchor and the coaptation element along the longitudinal axis of the actuation element (e.g., actuation shaft, actuation rod, actuation tube, actuation wire, etc.). In some implementations, the anchor and the coaptation element can be positioned simultaneously by moving the anchor and the coaptation element together along the longitudinal axis of the actuation element, e.g., shaft, actuation wire, etc.). The anchor can be configured to be positioned behind a native leaflet when implanted such that the leaflet is grasped by the anchor.

The device or implant can be configured to be implanted via a delivery system or other means for delivery. The delivery system can comprise one or more of a guide/delivery sheath, a delivery catheter, a steerable catheter, an implant catheter, tube, combinations of these, etc. The coaptation element and the anchor can be compressible to a radially compressed state and can be self-expandable to a radially expanded state when compressive pressure is released. The device can be configured for the anchor to be expanded radially away from the still compressed coaptation element initially in order to create a gap between the coaptation element and the anchor. A native leaflet can then be positioned in the gap. The coaptation element can be expanded radially, closing the gap between the coaptation element and the anchor and capturing the leaflet between the coaptation element and the anchor. In some implementations, the anchor and coaptation element are optionally configured to self-expand. The implantation methods for various implementations can be different and are more fully discussed below with respect to each implementation. Additional information regarding these and other delivery methods can be found in U.S. Pat. No. 8,449,599 and U.S. Patent Application Publication Nos. 2014/0222136, 2014/0067052, 2016/0331523, and PCT patent application publication Nos. WO2020/076898, each of which is incorporated herein by reference in its entirety for all purposes. These method(s) can be performed on a living animal or on a simulation, such as on a cadaver, cadaver heart, simulator (e.g., with the body parts, heart, tissue, etc. being simulated), etc. mutatis mutandis.

The disclosed devices or implants can be configured such that the anchor is connected to a leaflet, taking advantage of the tension from native chordae tendineae to resist high systolic pressure urging the device toward the left atrium. During diastole, the devices can rely on the compressive and retention forces exerted on the leaflet that is grasped by the anchor.

Referring now to FIGS. 8-15, a schematically illustrated implantable device or implant 100 (e.g., a prosthetic spacer device, valve repair device, etc.) is shown in various stages of deployment. The device or implant 100 and other similar devices/implants are described in more detail in PCT patent application publication Nos. WO2018/195215, WO2020/076898, and WO 2019/139904, which are incorporated herein by reference in their entirety. The device 100 can include any other features for an implantable device or implant discussed in the present application or the applications cited above, and the device 100 can be positioned to engage valve tissue (e.g., leaflets 20, 22, 30, 32, 34) as part of any suitable valve repair system (e.g., any valve repair system disclosed in the present application or the applications cited above).

The device or implant 100 is deployed from a delivery system or other means for delivery 102. The delivery system 102 can comprise one or more of a catheter, a sheath, a guide catheter/sheath, a delivery catheter/sheath, a steerable catheter, an implant catheter, a tube, a channel, a pathway, combinations of these, etc. The device or implant 100 includes a coaption or coaptation portion 104 and an anchor portion 106.

In some implementations, the coaptation portion 104 of the device or implant 100 includes a coaptation element or means for coapting 110 (e.g., spacer, plug, filler, foam, sheet, membrane, coaption element, etc.) that is adapted to be implanted between leaflets of a native valve (e.g., a native mitral valve, native tricuspid valve, etc.) and is slidably attached to an actuation element 112 (e.g., actuation wire, actuation shaft, actuation tube, etc.). The anchor portion 106 includes one or more anchors 108 that are actuatable between open and closed conditions and can take a wide variety of forms, such as, for example, paddles, gripping elements, or the like. Actuation of the means for actuating or actuation element 112 opens and closes the anchor portion 106 of the device 100 to grasp the native valve leaflets during implantation. The means for actuating or actuation element 112 (as well as other means for actuating and actuation elements herein) can take a wide variety of different forms (e.g., as a wire, rod, shaft, tube, screw, suture, line, strip, combination of these, etc.), be made of a variety of different materials, and have a variety of configurations. As one example, the actuation element can be threaded such that rotation of the actuation element moves the anchor portion 106 relative to the coaptation portion 104. Or, the actuation element can be unthreaded, such that pushing or pulling the actuation element 112 moves the anchor portion 106 relative to the coaptation portion 104.

The anchor portion 106 and/or anchors of the device 100 include outer paddles 120 and inner paddles 122 that are, in some implementations, connected between a cap 114 and the means for coapting or coaptation element 110 by portions 124, 126, 128. The portions 124, 126, 128 can be jointed and/or flexible to move between all of the positions described below. The interconnection of the outer paddles 120, the inner paddles 122, the coaptation element 110, and the cap 114 by the portions 124, 126, and 128 can constrain the device to the positions and movements illustrated herein.

In some implementations, the delivery system 102 includes a steerable catheter, implant catheter, and means for actuating or actuation element 112 (e.g., actuation wire, actuation shaft, etc.). These can be configured to extend through a guide catheter/sheath (e.g., a transseptal sheath, etc.). In some implementations, the means for actuating or actuation element 112 extends through a delivery catheter and the means for coapting or coaptation element 110 to the distal end (e.g., a cap 114 or other attachment portion at the distal connection of the anchor portion 106). Extending and retracting the actuation element 112 increases and decreases the spacing between the coaptation element 110 and the distal end of the device (e.g., the cap 114 or other attachment portion), respectively. In some implementations, a collar or other attachment element removably attaches the coaptation element 110 to the delivery system 102, either directly or indirectly, so that the means for actuating or actuation element 112 slides through the collar or other attachment element and, in some implementations, through a means for coapting or coaptation element 110 during actuation to open and close the paddles 120, 122 of the anchor portion 106 and/or anchors 108.

In some implementation, the anchor portion 106 and/or anchors 108 can include attachment portions or gripping members. The illustrated gripping members can comprise clasps 130 that include a base or fixed arm 132, a moveable arm 134, optional barbs, friction-enhancing elements, or other means for securing 136 (e.g., protrusions, ridges, grooves, textured surfaces, adhesive, etc.), and a joint portion 138. The fixed arms 132 are attached to the inner paddles 122. In some implementations, the fixed arms 132 are attached to the inner paddles 122 with the joint portion 138 disposed proximate means for coapting or coaptation element 110. In some implementations, the clasps (e.g., barbed clasps, etc.) have flat surfaces and do not fit in a recess of the inner paddle. Rather, the flat portions of the clasps are disposed against the surface of the inner paddle 122. The joint portion 138 provides a spring force between the fixed and moveable arms 132, 134 of the clasp 130. The joint portion 138 can be any suitable joint, such as a flexible joint, a spring joint, a pivot joint, or the like. In some implementations, the joint portion 138 is a flexible piece of material integrally formed with the fixed and moveable arms 132, 134. The fixed arms 132 are attached to the inner paddles 122 and remain stationary or substantially stationary relative to the inner paddles 122 when the moveable arms 134 are opened to open the clasps 130 and expose the barbs, friction-enhancing elements, or means for securing 136.

In some implementations, the clasps 130 are opened by applying tension to actuation lines 116 attached to the moveable arms 134, thereby causing the moveable arms 134 to articulate, flex, or pivot on the joint portions 138. The actuation lines 116 extend through the delivery system 102 (e.g., through a steerable catheter and/or an implant catheter). Other actuation mechanisms are also possible.

The actuation line 116 can take a wide variety of forms, such as, for example, a line, a suture, a wire, a rod, a catheter, or the like. The clasps 130 can be spring loaded so that in the closed position the clasps 130 continue to provide a pinching force on the grasped native leaflet. This pinching force remains constant regardless of the position of the inner paddles 122. Optional barbs, friction-enhancing elements, or other means for securing 136 of the clasps 130 can grab, pinch, and/or pierce the native leaflets to further secure the native leaflets.

During implantation, the paddles 120, 122 can be opened and closed, for example, to grasp the native leaflets (e.g., native mitral valve leaflets, etc.) between the paddles 120, 122 and/or between the paddles 120, 122 and a means for coapting or coaptation element 110. The clasps 130 can be used to grasp and/or further secure the native leaflets by engaging the leaflets with barbs, friction-enhancing elements, or means for securing 136 and pinching the leaflets between the moveable and fixed arms 134, 132. The barbs, friction-enhancing elements, or other means for securing 136 (e.g., barbs, protrusions, ridges, grooves, textured surfaces, adhesive, etc.) of the clasps or barbed clasps 130 increase friction with the leaflets or may partially or completely puncture the leaflets. The actuation lines 116 can be actuated separately so that each clasp 130 can be opened and closed separately. Separate operation allows one leaflet to be grasped at a time, or for the repositioning of a clasp 130 on a leaflet that was insufficiently grasped, without altering a successful grasp on the other leaflet. The clasps 130 can be opened and closed relative to the position of the inner paddle 122 (as long as the inner paddle is in an open or at least partially open position), thereby allowing leaflets to be grasped in a variety of positions as the particular situation requires.

Figure 8:
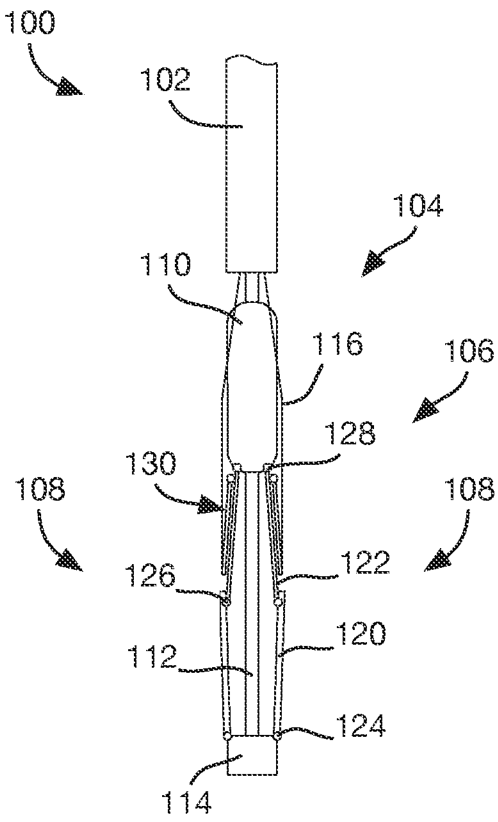
FIGS. 8-14 show an example of an implantable device or implant, in various stages of deployment.

Referring now to FIG. 8, the device 100 is shown in an elongated or fully open condition for deployment from an implant delivery catheter of the delivery system 102. The device 100 is disposed at the end of the catheter of the delivery system 102 in the fully open position, because the fully open position takes up the least space and allows the smallest catheter to be used (or the largest device 100 to be used for a given catheter size). In the elongated condition the cap 114 is spaced apart from the means for coapting or coaptation element 110 such that the paddles 120, 122 are fully extended. In some implementations, an angle formed between the interior of the outer and inner paddles 120, 122 is approximately 180 degrees. The clasps 130 are kept in a closed condition during deployment through the delivery system 102 so that the barbs, friction-enhancing elements, or other means for securing 136 (FIG. 9) do not catch or damage the delivery system 102 or tissue in the patient's heart. The actuation lines 116 can extend and attach to the moveable arms 134.

Figure 9:
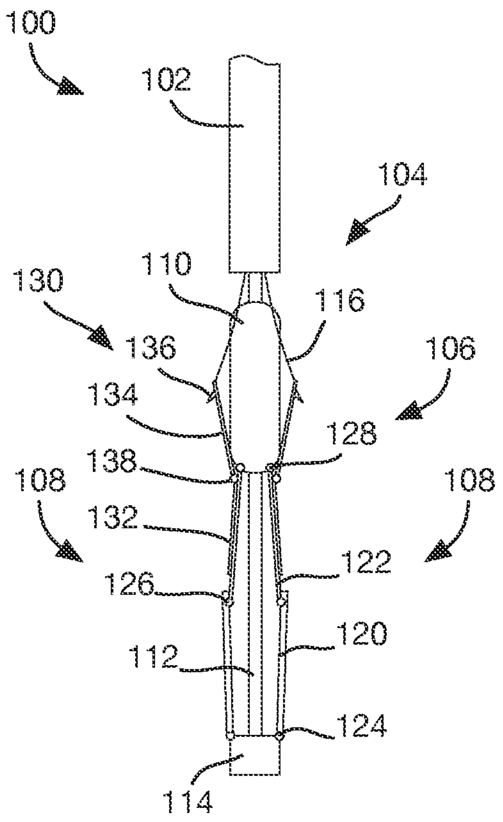

Referring now to FIG. 9, the device 100 is shown in an elongated detangling condition, similar to FIG. 8, but with the clasps 130 in a fully open position, ranging from about 140 degrees to about 200 degrees, from about 170 degrees to about 190 degrees, or about 180 degrees between fixed and moveable portions 132, 134 of the clasps 130. Fully opening the paddles 120, 122 and the clasps 130 has been found to improve ease of detanglement or detachment from anatomy of the patient, such as the chordae tendineae CT, during implantation of the device 100.

Figure 10:
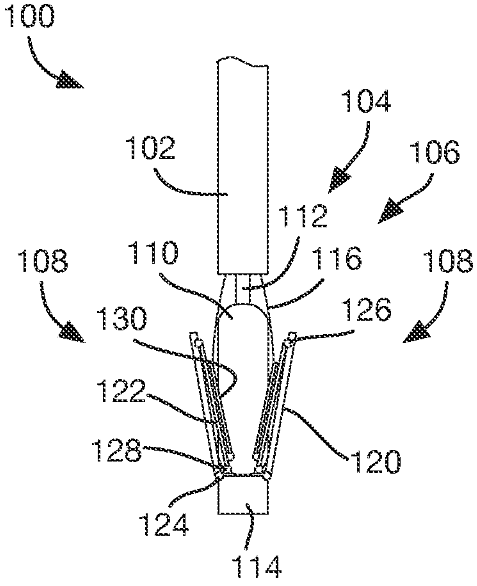
Figure 11:
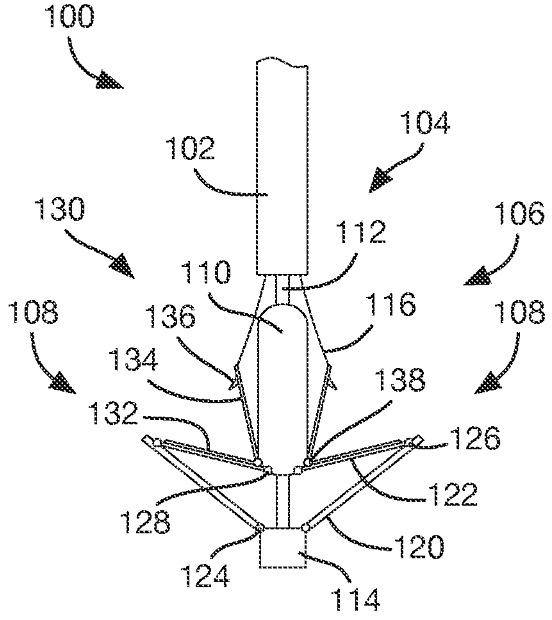

Referring now to FIG. 10, the device 100 is shown in a shortened or fully closed condition. The compact size of the device 100 in the shortened condition allows for easier maneuvering and placement within the heart. To move the device 100 from the elongated condition to the shortened condition, the means for actuating or actuation element 112 is retracted to pull the cap 114 towards the means for coapting or coaptation element 110. The connection portion (s) 126 (e.g., joint(s), flexible connection(s), etc.) between the outer paddle 120 and inner paddle 122 are constrained in movement such that compression forces acting on the outer paddle 120 from the cap 114 being retracted towards the means for coapting or coaptation element 110 cause the paddles or gripping elements to move radially outward. During movement from the open to closed position, the outer paddles 120 maintain an acute angle with the means for actuating or actuation element 112. The outer paddles 120 can optionally be biased toward a closed position. The inner paddles 122 during the same motion move through a considerably larger angle as they are oriented away from the means for coapting or coaptation element 110 in the open condition and collapse along the sides of the means for coapting or coaptation element 110 in the closed condition. In some implementations, the inner paddles 122 are thinner and/or narrower than the outer paddles 120, and the connection portions 126, 128 (e.g., joints, flexible connections, etc.) connected to the inner paddles 122 can be thinner and/or more flexible. For example, this increased flexibility can allow more movement than the connection portion 124 connecting the outer paddle 120 to the cap 114. In some implementations, the outer paddles 120 are narrower than the inner paddles 122. The connection portions 126, 128 connected to the inner paddles 122 can be more flexible, for example, to allow more movement than the connection portion 124 connecting the outer paddle 120 to the cap 114. In some implementations, the inner paddles 122 can be the same or substantially the same width as the outer paddles Referring now to FIGS. 11-13, the device 100 is shown in a partially open, grasp-ready condition. To transition from the fully closed to the partially open condition, the means for actuating or actuation element (e.g., actuation wire, actuation shaft, etc.) is extended to push the cap 114 away from the means for coapting or coaptation element 110, thereby pulling on the outer paddles 120, which in turn pull on the inner paddles 122, causing the anchors or anchor portion 106 to partially unfold. The actuation lines 116 are also retracted to open the clasps 130 so that the leaflets can be grasped. In some implementations, the pair of inner and outer paddles 122, 120 are moved in unison, rather than independently, by a single means for actuating or single actuation element 112. Also, the positions of the clasps 130 are dependent on the positions of the paddles 122, 120. For example, referring to FIG. 10 closing the paddles 122, 120 also closes the clasps. In some implementations, the paddles 120, 122 can be independently controllable. For example, the device 100 can have two actuation elements and two independent caps (or other attachment portions), such that one independent actuation element (e.g., wire, shaft, etc.) and cap (or other attachment portion) are used to control one paddle, and the other independent actuation element and cap (or other attachment portion) are used to control the other paddle.

Figure 12:
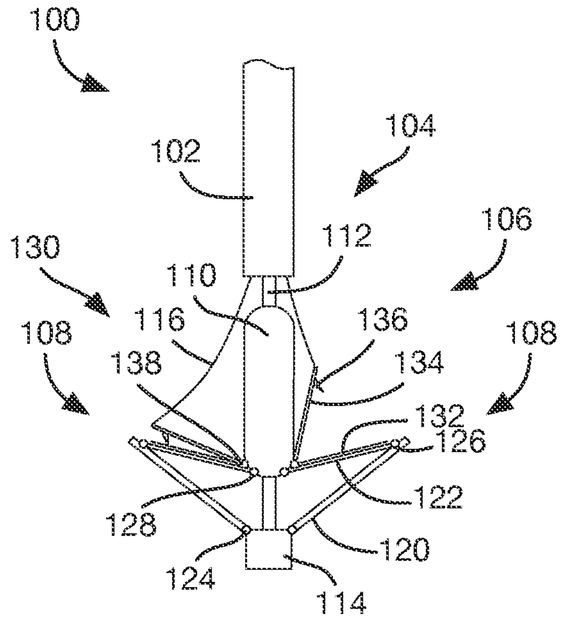
Figure 13:
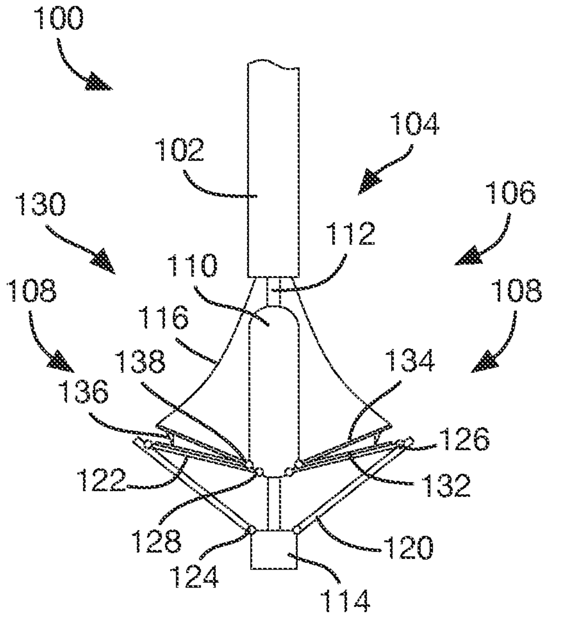

Referring now to FIG. 12, one of the actuation lines 116 is extended to allow one of the clasps 130 to close. Referring now to FIG. 13, the other actuation line 116 is extended to allow the other clasp 130 to close. Either or both of the actuation lines 116 can be repeatedly actuated to repeatedly open and close the clasps 130.

Figure 14:
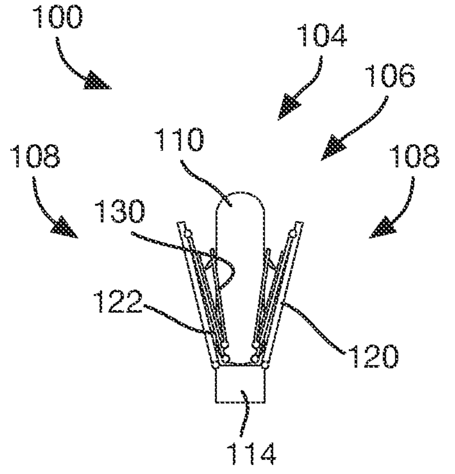

Referring now to FIG. 14, the device 100 is shown in a fully closed and deployed condition. The delivery system or means for delivery 102 and means for actuating or actuation element 112 are retracted and the paddles 120, 122 and clasps 130 remain in a fully closed position. Once deployed, the device 100 can be maintained in the fully closed position with a mechanical latch or can be biased to remain closed through the use of spring materials, such as steel, other metals, plastics, composites, etc. or shape-memory alloys such as Nitinol. For example, the connection portions 124, 126, 128, the joint portions 138, and/or the inner and outer paddles 122, and/or an additional biasing component (not shown) can be formed of metals such as steel or shape-memory alloy, such as Nitinol—produced in a wire, sheet, tubing, or laser sintered powder—and are biased to hold the outer paddles 120 closed around the means for coapting or coaptation element 110 and the clasps 130 pinched around native leaflets. Similarly, the fixed and moveable arms 132, 134 of the clasps 130 are biased to pinch the leaflets. In some implementations, the attachment or connection portions 124, 126, 128, joint portions 138, and/or the inner and outer paddles 122, and/or an additional biasing component (not shown) can be formed of any other suitably elastic material, such as a metal or polymer material, to maintain the device 100 in the closed condition after implantation.

Figure 15:
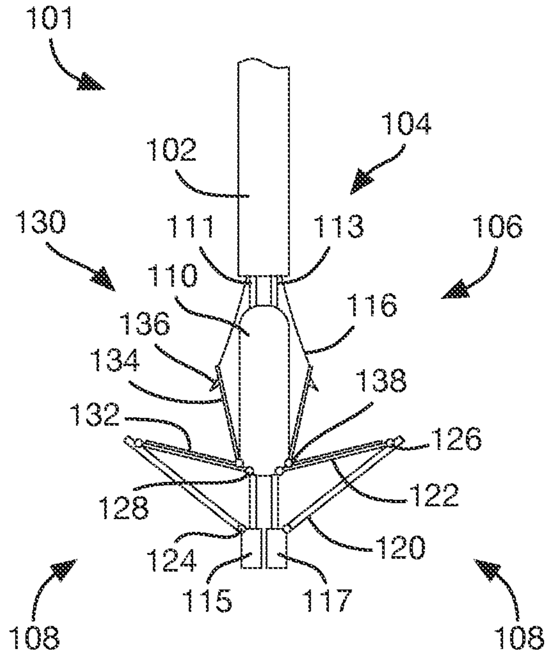
FIG. 15 shows an example of an implantable device or implant that is similar to the device illustrated by FIGS. 8-14, but where the paddles are independently controllable.

FIG. 15 illustrates an example where the paddles 120, 122 are independently controllable. The device 101 illustrated by FIG. 15 is similar to the device illustrated by FIG. 11, except the device 100 of FIG. 15 includes an actuation element that is configured as two independent actuation elements or actuation wires 111, 113 that are coupled to two independent caps 115, 117. To transition a first inner paddle 122 and a first outer paddle 120 from the fully closed to the partially open condition, the means for actuating or actuation element 111 is extended to push the cap 115 away from the means for coapting or coaptation element 110, thereby pulling on the outer paddle 120, which in turn pulls on the inner paddle 122, causing the first anchor 108 to partially unfold. To transition a second inner paddle 122 and a second outer paddle 120 from the fully closed to the partially open condition, the means for actuating or actuation element 113 is extended to push the cap 115 away from the means for coapting or coaptation element 110, thereby pulling on the outer paddle 120, which in turn pulls on the inner paddle 122, causing the second anchor 108 to partially unfold. The independent paddle control illustrated by FIG. 15 can be implemented on any of the devices disclosed by the present application. For comparison, in the example illustrated by FIG. 11, the pair of inner and outer paddles 122, 120 are moved in unison, rather than independently, by a single means for actuating or actuation element 112.

Figure 16:
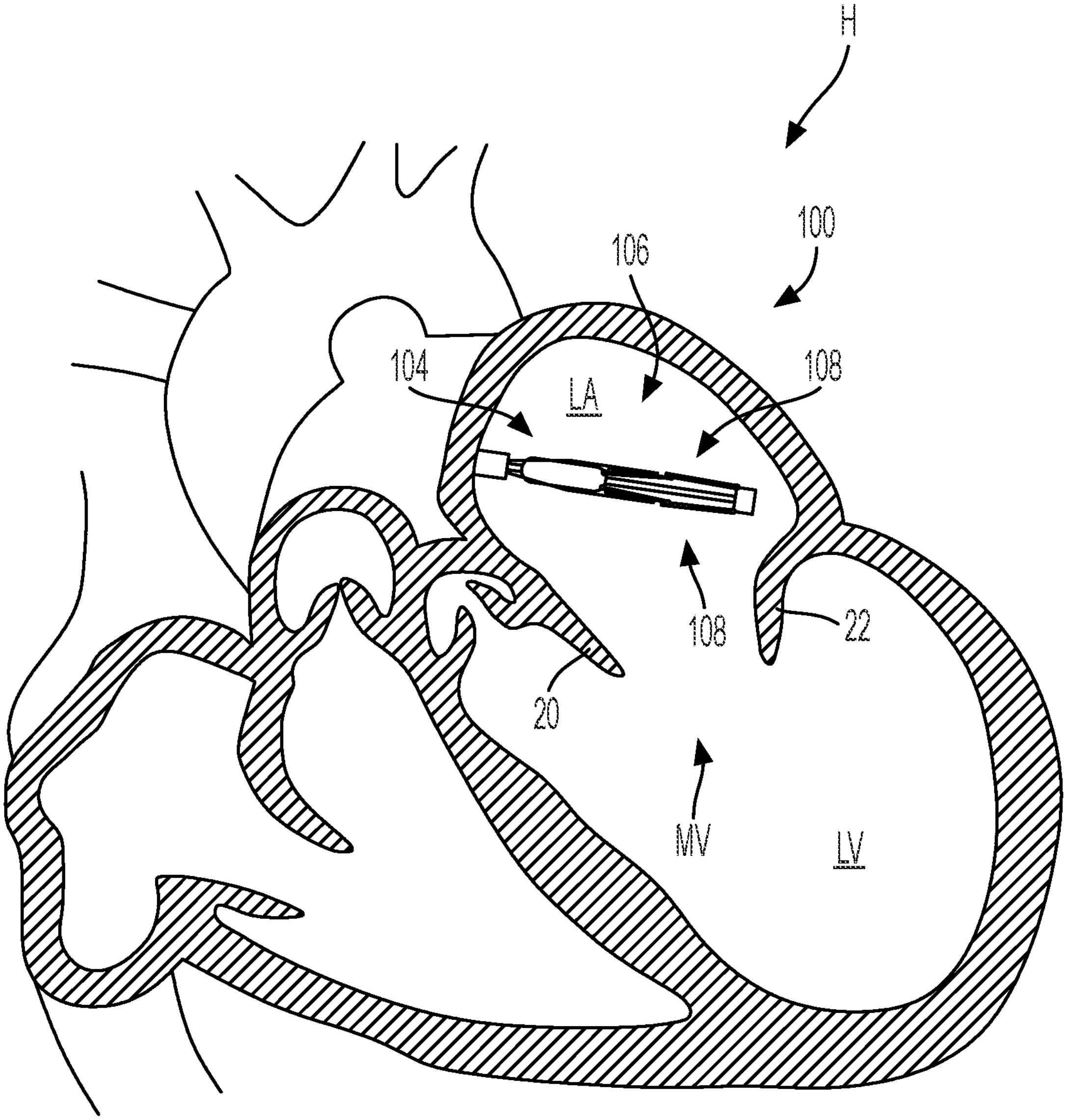
FIGS. 16-21 show the example implantable device or implant of FIGS. 8-14 being delivered and implanted within a native valve.
Figure 17:
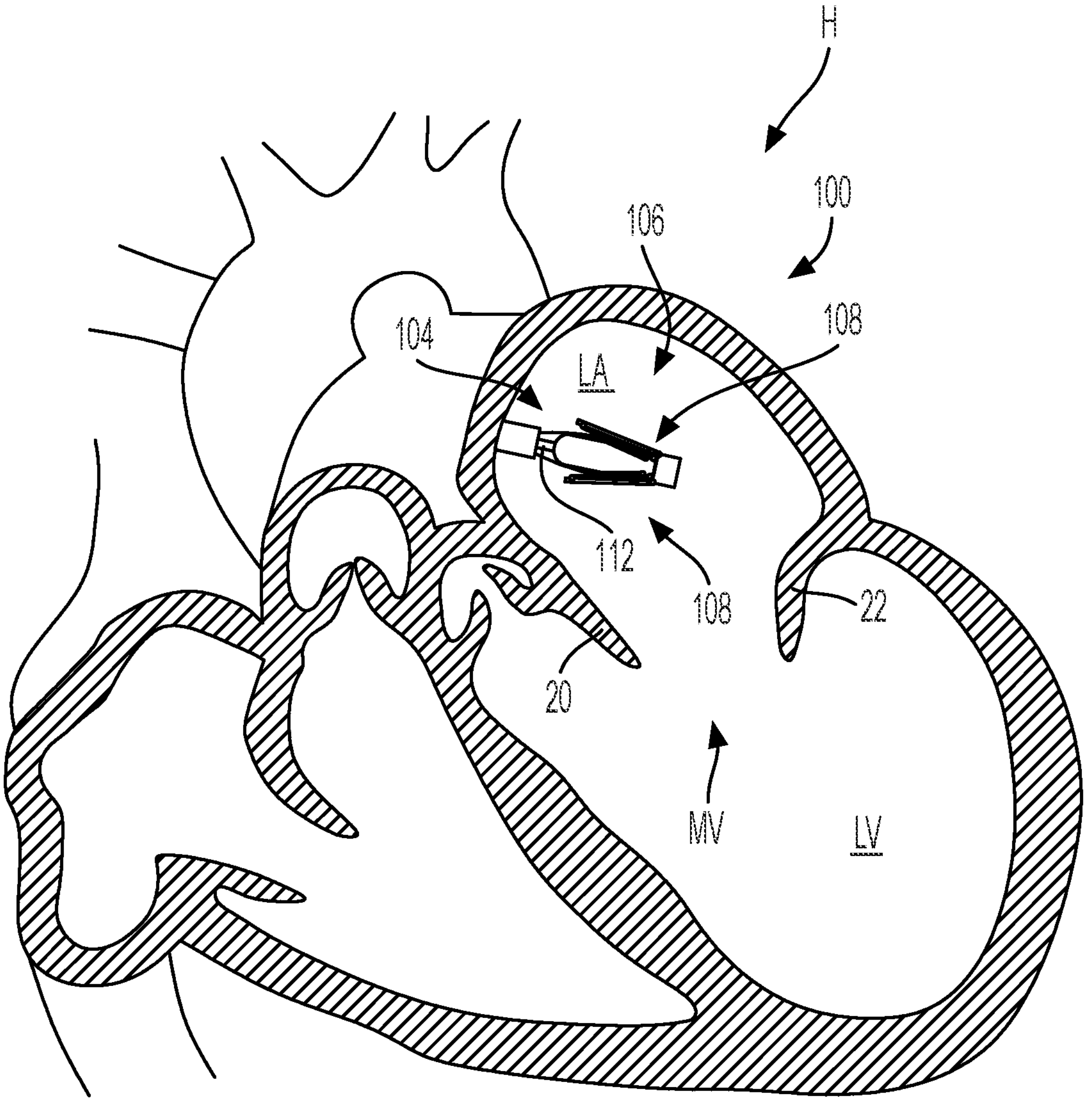

Referring now to FIGS. 16-21, the implantable device 100 of FIGS. 8-14 is shown being delivered and implanted within the native mitral valve MV of the heart H. Referring to FIG. 16, a delivery sheath/catheter is inserted into the left atrium LA through the septum and the implant/device 100 is deployed from the delivery catheter/sheath in the fully open condition as illustrated in FIG. 16. The means for actuating or actuation element 112 is then retracted to move the implant/device into the fully closed condition shown in FIG. 17.

Figure 18:
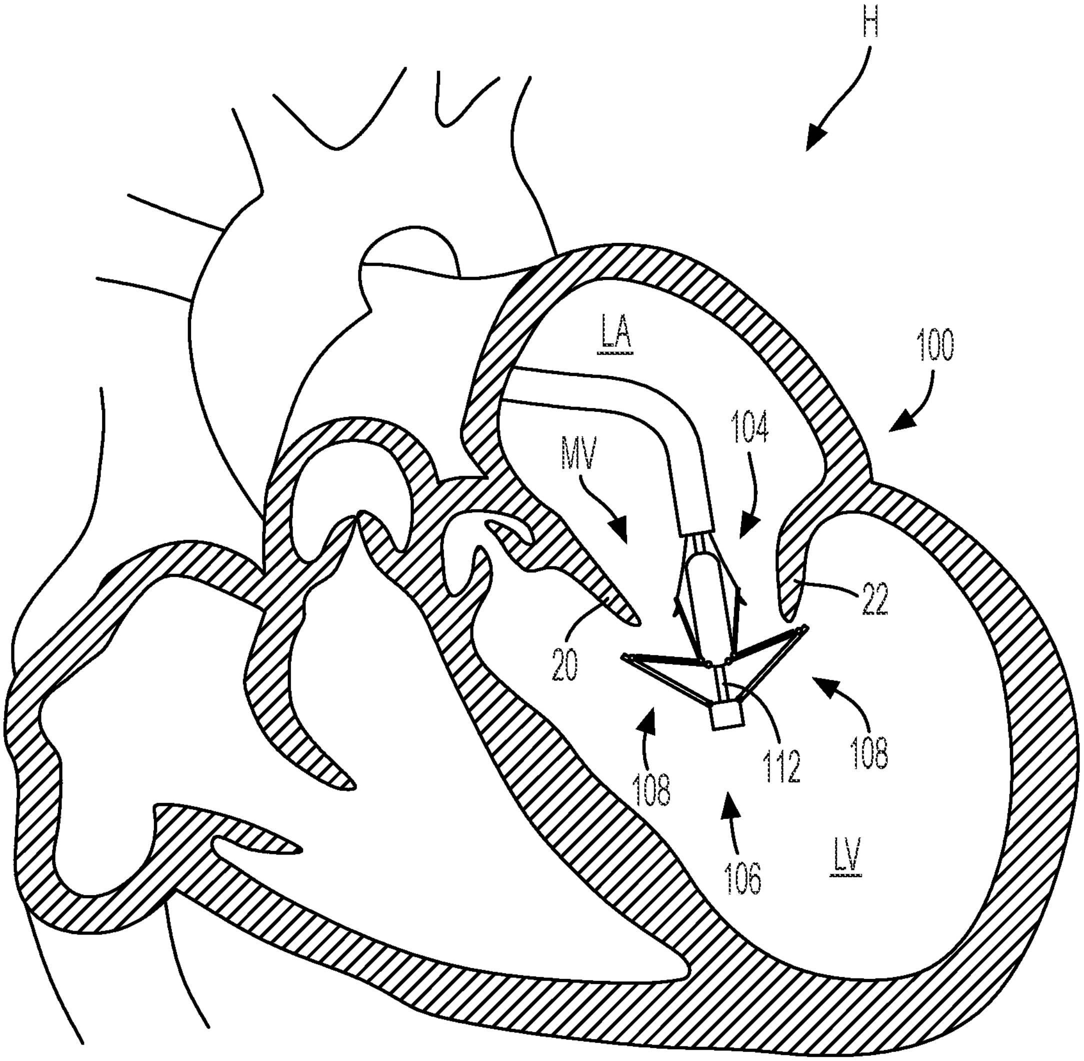

As can be seen in FIG. 18, the implant/device is moved into position within the mitral valve MV into the ventricle LV and partially opened so that the leaflets 20, 22 can be grasped. For example, a steerable catheter can be advanced and steered or flexed to position the steerable catheter as illustrated by FIG. 18. The implant catheter connected to the implant/device can be advanced from inside the steerable catheter to position the implant as illustrated by FIG. 18.

Figure 19:
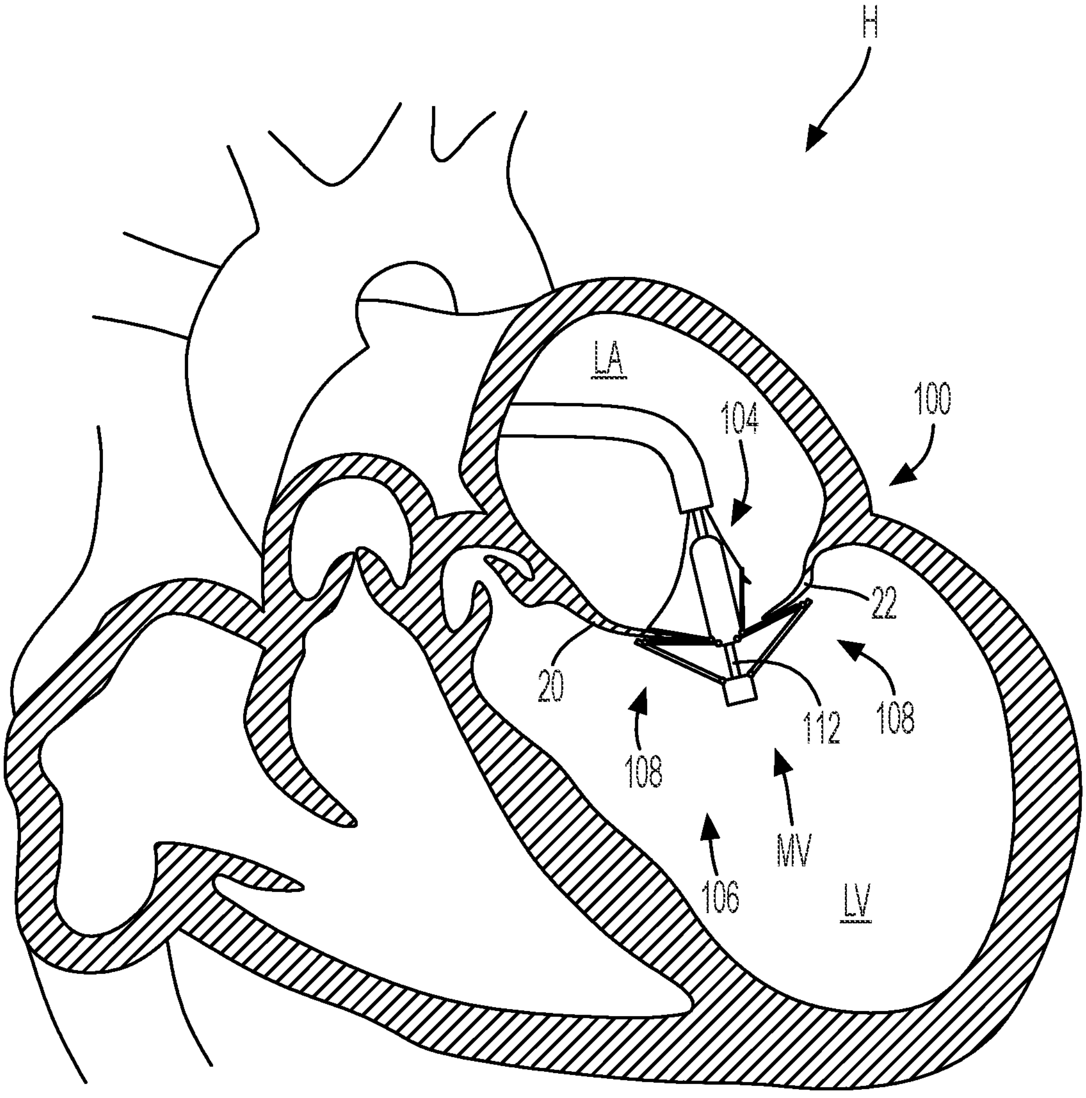
Figure 20:
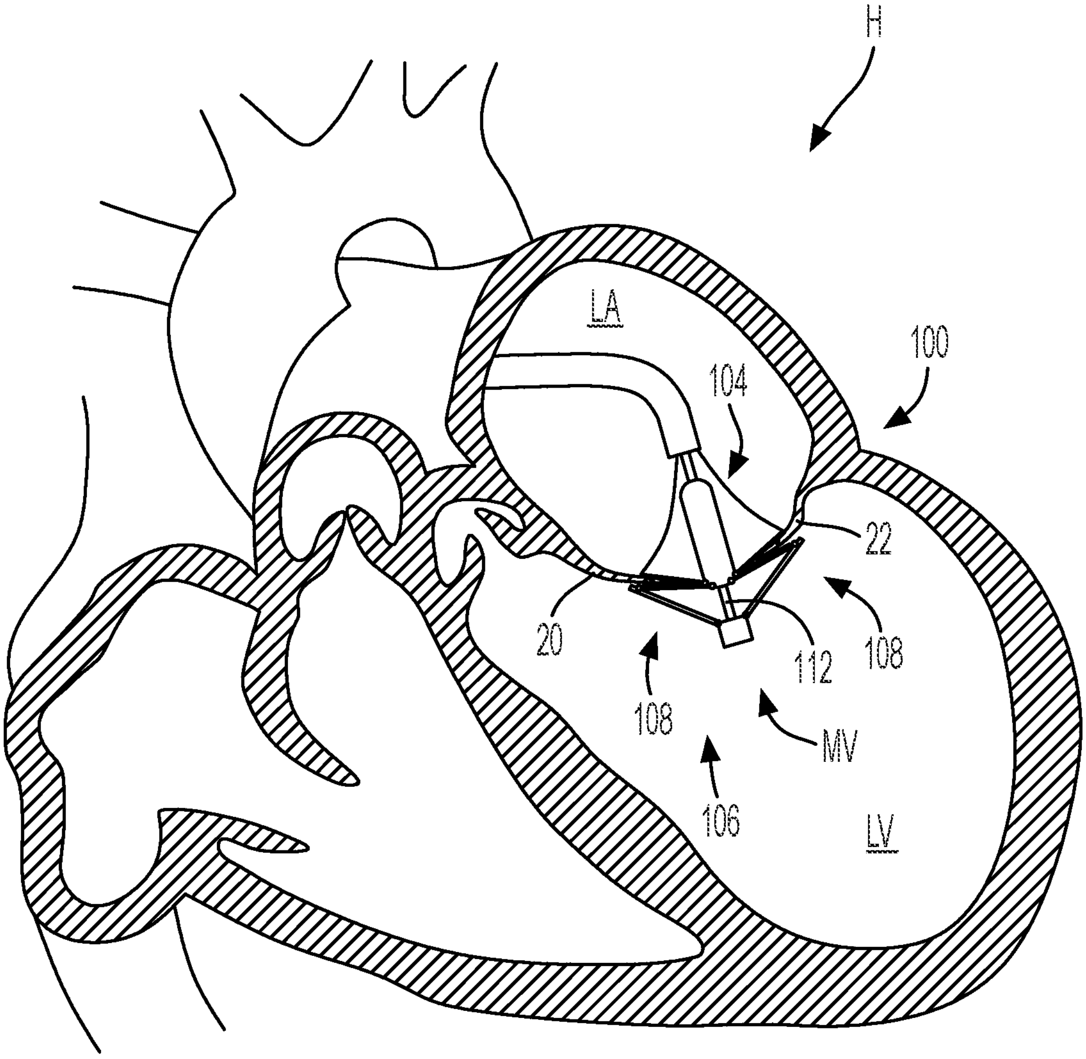
Figure 21:
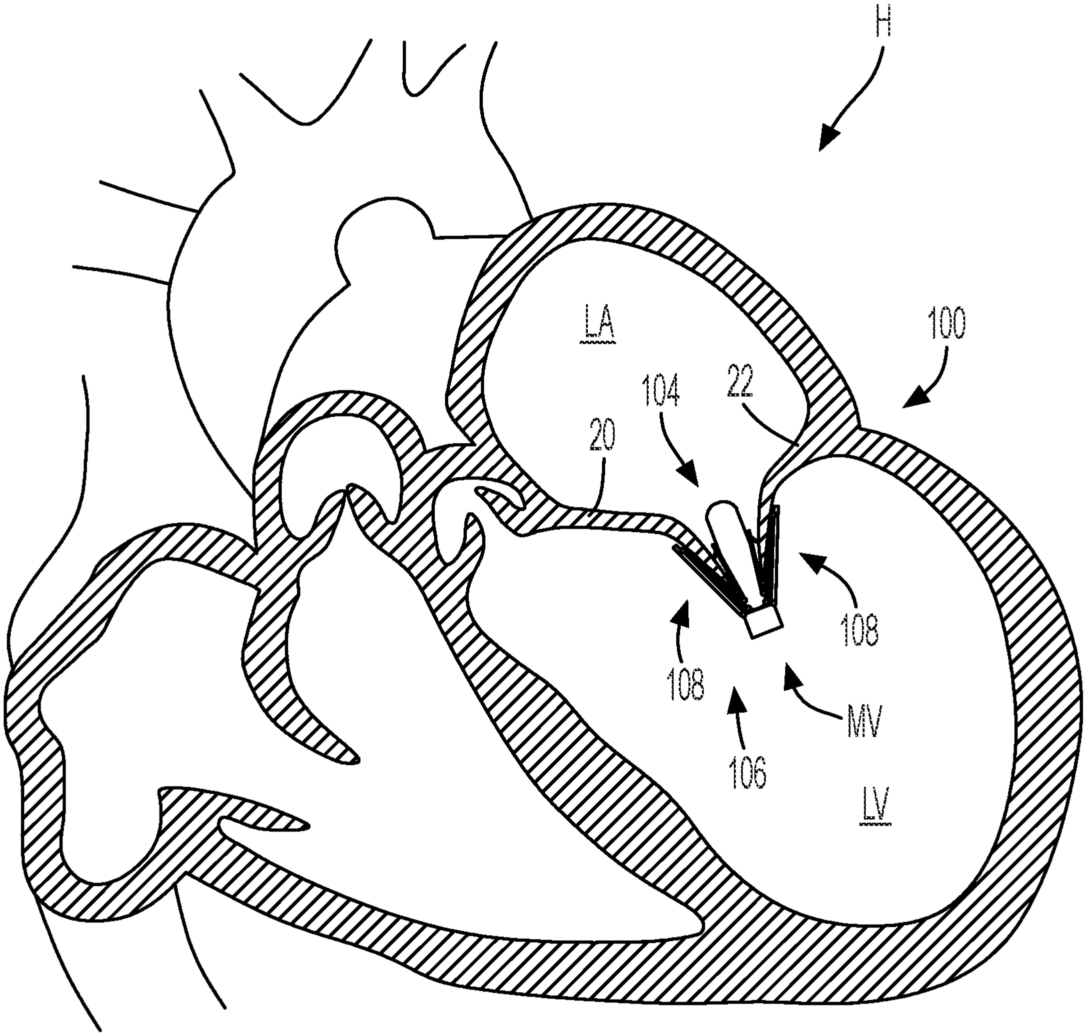
Figure 22:
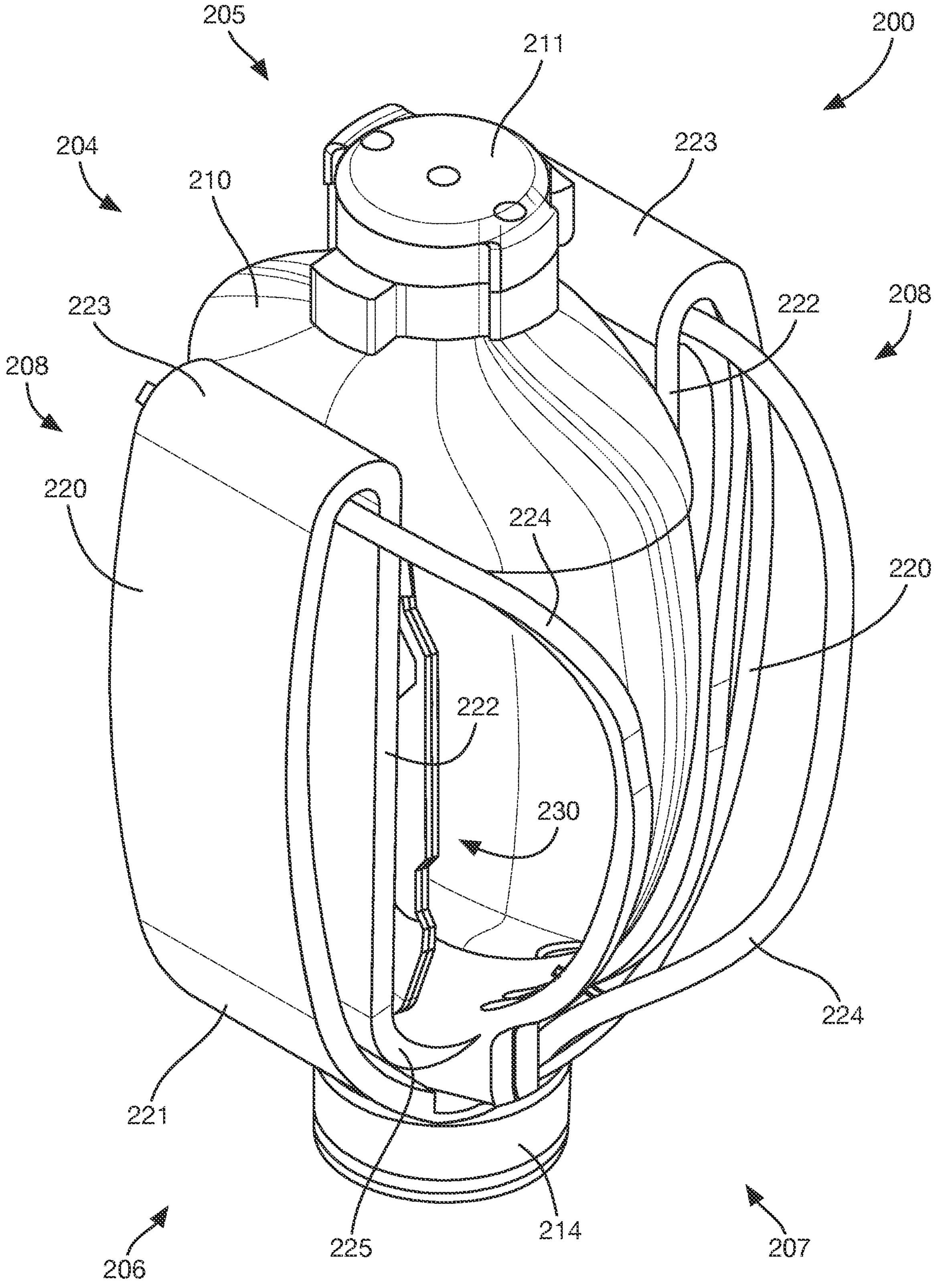
FIG. 22 shows a perspective view of an example implantable device or implant in a closed position.
Figure 23:
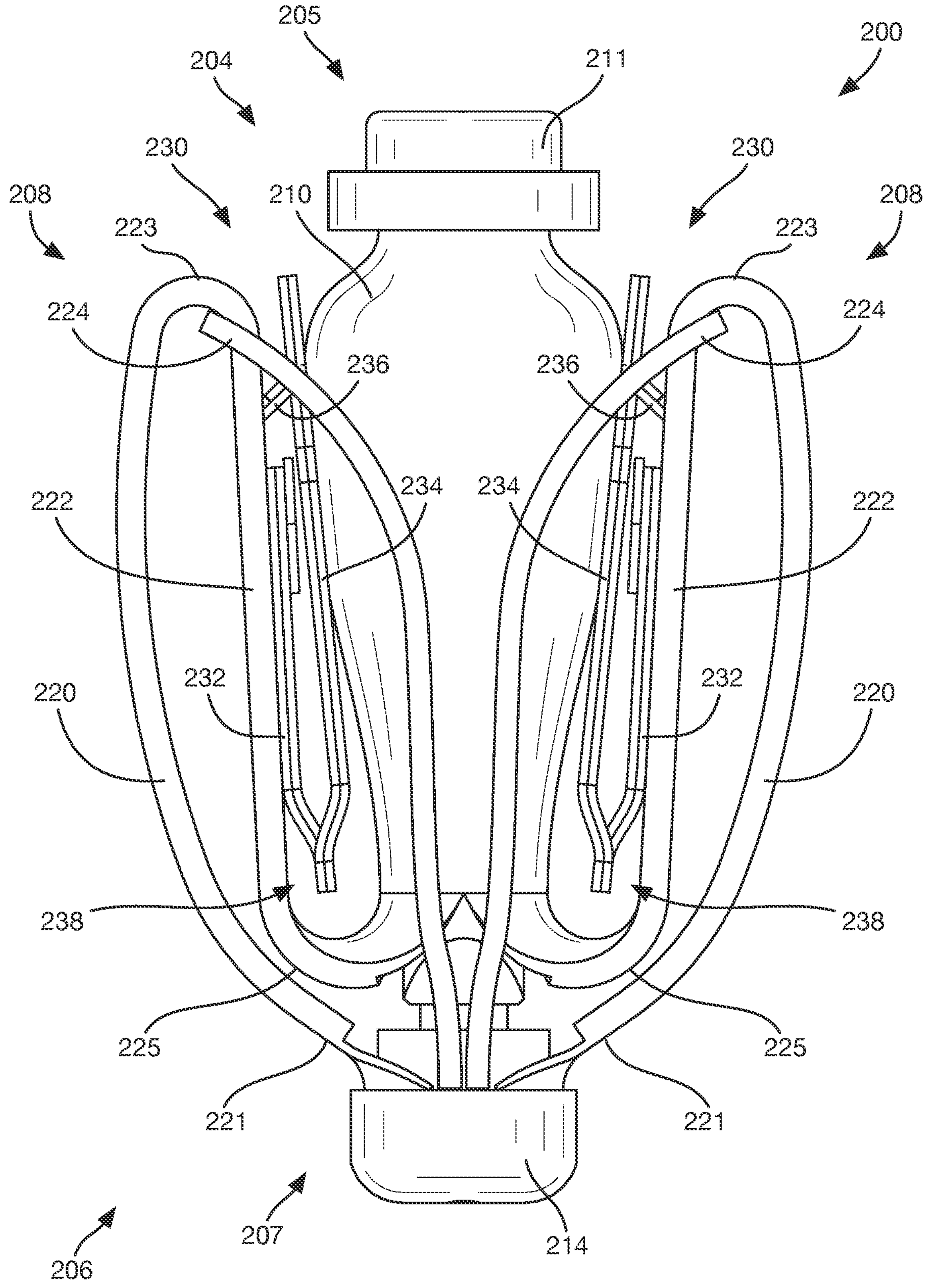
FIG. 23 shows a front view of the implantable device or implant of FIG. 22.

Referring now to FIG. 19, the implant catheter can be retracted into the steerable catheter to position the valve leaflets 20, 22 in the clasps 130. An actuation line 116 is extended to close one of the clasps 130, capturing a leaflet 20. FIG. 20 shows the other actuation line 116 being then extended to close the other clasp 130, capturing the remaining leaflet 22. Lastly, as can be seen in FIG. 21, the delivery system 102 (e.g., steerable catheter, implant catheter, etc.), means for actuating or actuation element 112 and actuation lines 116 are then retracted and the device or implant 100 is fully closed and deployed in the native mitral valve MV.

Referring now to FIGS. 22-27, an example of an implantable device or implant or implant 200 is shown. The implantable device 200 is one of the many different configurations that the device 100 that is schematically illustrated in FIGS. 8-14 can take.

The device 200 can include any other features for an implantable device or implant discussed in the present application, and the device 200 can be positioned to engage valve tissue 20, 22 as part of any suitable valve repair system (e.g., any valve repair system disclosed in the present application). The device/implant 200 can be a prosthetic spacer device, valve repair device, or another type of implant that attaches to leaflets of a native valve.

In some implementations, the implantable device or implant 200 includes a coaption or coaptation portion 204, a proximal or attachment portion 205, an anchor portion 206, and a distal portion 207. In some implementations, the coaption or coaptation portion 204 of the device optionally includes a coaptation element 210 (e.g., a spacer, coaption element, plug, membrane, sheet, etc.) for implantation between leaflets of a native valve. In some implementations, the anchor portion 206 includes a plurality of anchors 208. The anchors can be configured in a variety of ways. In some implementations, each anchor 208 includes outer paddles 220, inner paddles 222, paddle extension members or paddle frames 224, and clasps 230. In some implementations, the attachment portion 205 includes a first or proximal collar 211 (or other attachment element) for engaging with a capture mechanism 213 (FIGS. 43-49) of a delivery system 202 (FIGS. 38-42 and 49). Delivery system 202 can be the same as or similar to delivery system 102 described elsewhere and can comprise one or more of a catheter, a sheath, a guide catheter/sheath, a delivery catheter/sheath, a steerable catheter, an implant catheter, a tube, a channel, a pathway, combinations of these, etc.

In some implementations, the coaptation element 210 and paddles 220, 222 are formed from a flexible material that can be a metal fabric, such as a mesh, woven, braided, or formed in any other suitable way or a laser cut or otherwise cut flexible material. The material can be cloth, shape-memory alloy wire-such as Nitinol—to provide shape-setting capability, or any other flexible material suitable for implantation in the human body.

An actuation element 212 (e.g., actuation shaft, actuation rod, actuation tube, actuation wire, actuation line, etc.) extends from the delivery system 202 to engage and enable actuation of the implantable device or implant 200. In some implementations, the actuation element 212 extends through the capture mechanism 213, proximal collar 211, and coaptation element 210 to engage a cap 214 of the distal portion 207. The actuation element 212 can be configured to removably engage the cap 214 with a threaded connection, or the like, so that the actuation element 212 can be disengaged and removed from the device 200 after implantation.

The coaptation element 210 extends from the proximal collar 211 (or other attachment element) to the inner paddles 222. In some implementations, the coaptation element 210 has a generally elongated and round shape, though other shapes and configurations are possible. In some implementations, the coaptation element 210 has an elliptical shape or cross-section when viewed from above (e.g., FIG. 51) and has a tapered shape or cross-section when seen from a front view (e.g., FIG. 23) and a round shape or cross-section when seen from a side view (e.g., FIG. 24). A blend of these three geometries can result in the three-dimensional shape of the illustrated coaptation element 210 that achieves the benefits described herein. The round shape of the coaptation element 210 can also be seen, when viewed from above, to substantially follow or be close to the shape of the paddle frames 224.

The size and/or shape of the coaptation element 210 can be selected to minimize the number of implants that a single patient will require (preferably one), while at the same time maintaining low transvalvular gradients. In some implementations, the anterior-posterior distance at the top of the coaptation element is about 5 mm, and the medial-lateral distance of the coaptation element at its widest is about 10 mm. In some implementations, the overall geometry of the device 200 can be based on these two dimensions and the overall shape strategy described above. It should be readily apparent that the use of other anterior-posterior distance anterior-posterior distance and medial-lateral distance as starting points for the device will result in a device having different dimensions. Further, using other dimensions and the shape strategy described above will also result in a device having different dimensions.

In some implementations, the outer paddles 220 are jointably attached to the cap 214 of the distal portion 207 by connection portions 221 and to the inner paddles 222 by connection portions 223. The inner paddles 222 are jointably attached to the coaptation element by connection portions 225. In this manner, the anchors 208 are configured similar to legs in that the inner paddles 222 are like upper portions of the legs, the outer paddles 220 are like lower portions of the legs, and the connection portions 223 are like knee portions of the legs.

In some implementations, the inner paddles 222 are stiff, relatively stiff, rigid, have rigid portions and/or are stiffened by a stiffening member or a fixed portion 232 of the clasps 230. The stiffening of the inner paddle allows the device to move to the various different positions shown and described herein. The inner paddle 222, the outer paddle 220, the coaptation can all be interconnected as described herein, such that the device 200 is constrained to the movements and positions shown and described herein.

In some implementations, the paddle frames 224 are attached to the cap 214 at the distal portion 207 and extend to the connection portions 223 between the inner and outer paddles 222, 220. In some implementations, the paddle frames 224 are formed of a material that is more rigid and stiff than the material forming the paddles 222, 220 so that the paddle frames 224 provide support for the paddles 222, 220.

Figure 51:
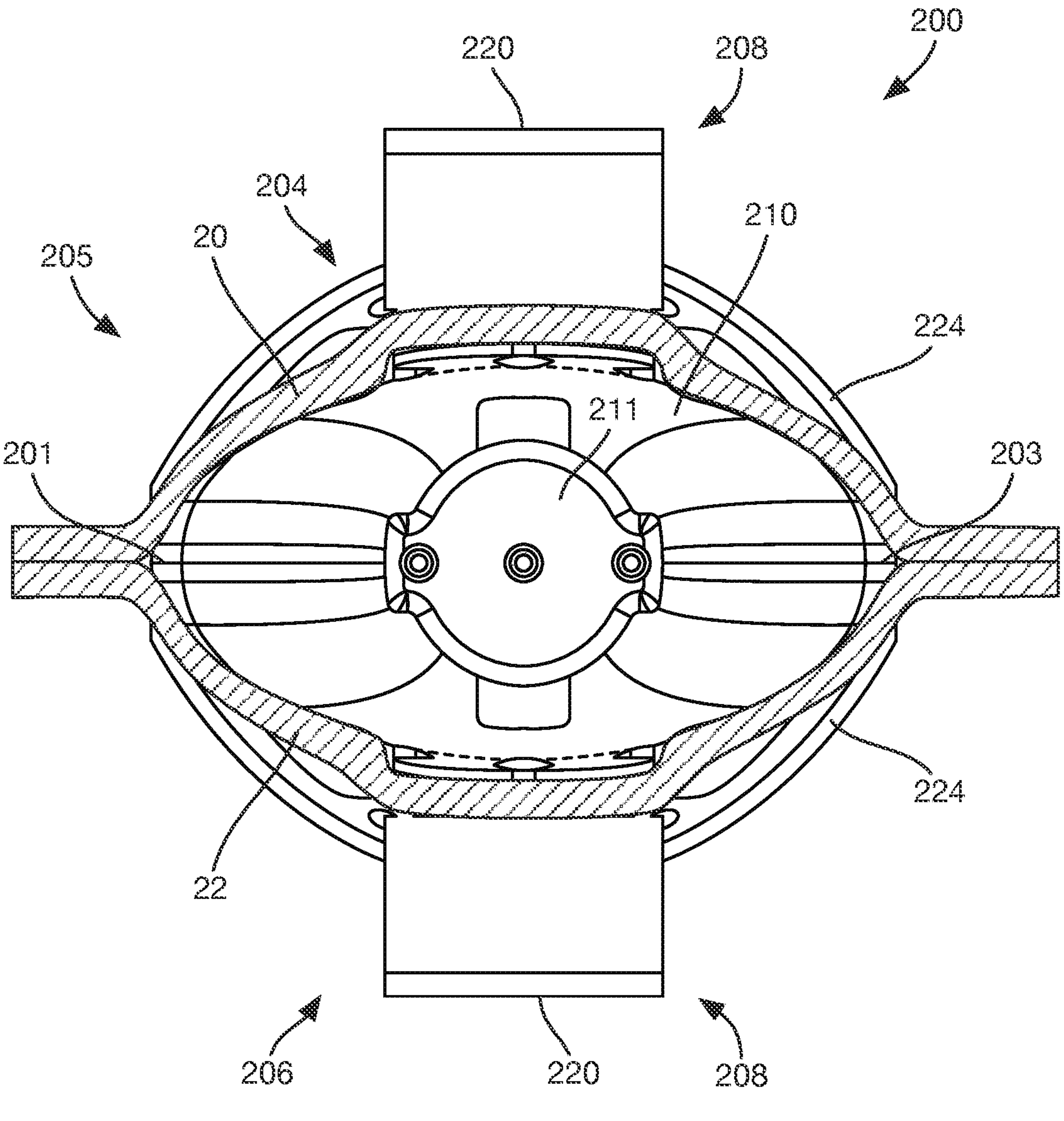
FIG. 51 is a top schematic view illustrating a path of native valve leaflets around a coaptation element or spacer of an example valve repair device or implant.
Figure 52:
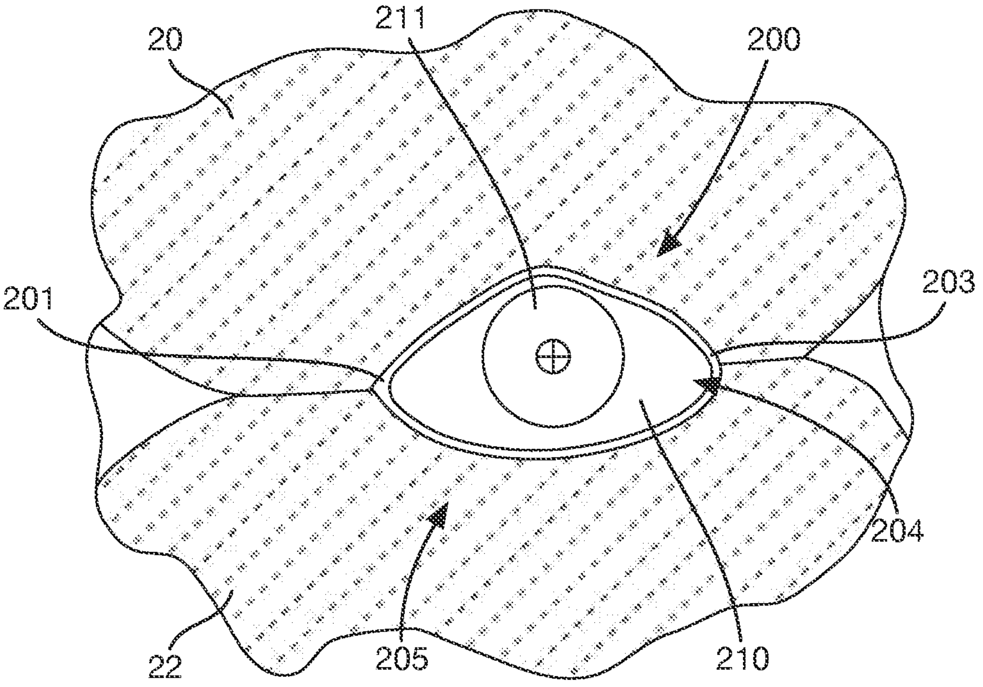
FIG. 52 illustrates a coaptation element or spacer in a gap of a native valve as viewed from an atrial side of the native valve.
Figure 53:
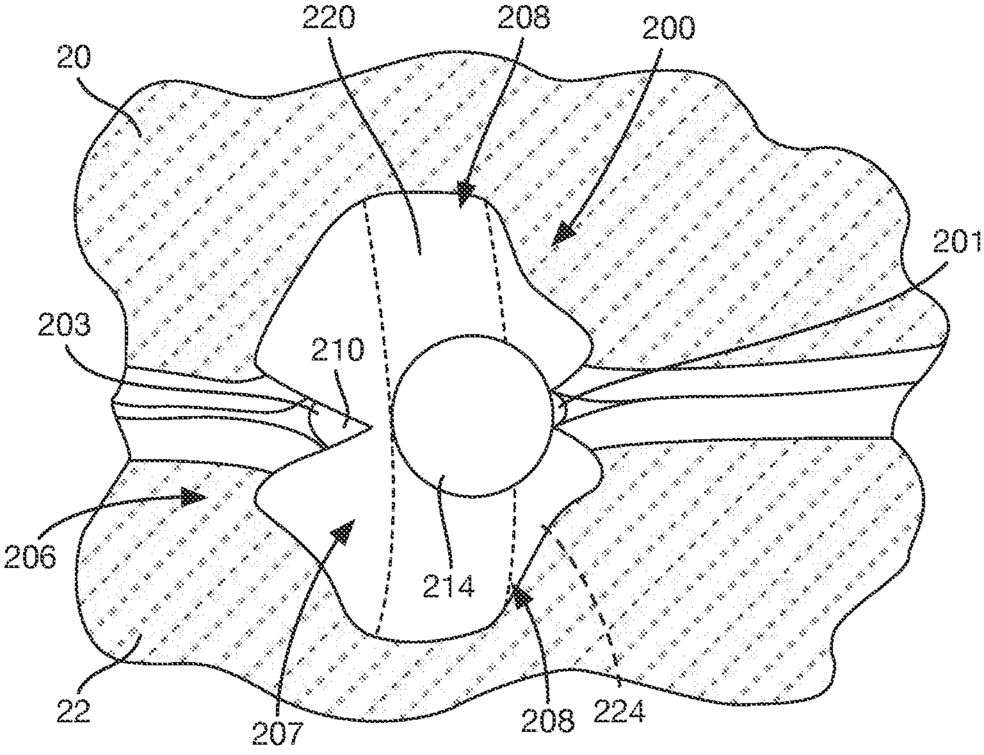
FIG. 53 illustrates a valve repair device or implant attached to native valve leaflets with the coaptation element or spacer in the gap of the native valve as viewed from a ventricular side of the native valve.

The paddle frames 224 provide additional pinching force between the inner paddles 222 and the coaptation element 210 and assist in wrapping the leaflets around the sides of the coaptation element 210 for a better seal between the coaptation element 210 and the leaflets, as can be seen in FIG. 51. That is, the paddle frames 224 can be configured with a round three-dimensional shape extending from the cap 214 to the connection portions 223 of the anchors 208. The connections between the paddle frames 224, the outer and inner paddles 220, 222, the cap 214, and the coaptation element 210 can constrain each of these parts to the movements and positions described herein. In particular the connection portion 223 is constrained by its connection between the outer and inner paddles 220, 222 and by its connection to the paddle frame 224. Similarly, the paddle frame 224 is constrained by its attachment to the connection portion 223 (and thus the inner and outer paddles 222, 220) and to the cap 214.

Configuring the paddle frames 224 in this manner provides increased surface area compared to the outer paddles 220 alone. This can, for example, make it easier to grasp and secure the native leaflets. The increased surface area can also distribute the clamping force of the paddles 220 and paddle frames 224 against the native leaflets over a relatively larger surface of the native leaflets in order to further protect the native leaflet tissue. Referring again to FIG. 51, the increased surface area of the paddle frames 224 can also allow the native leaflets to be clamped to the implantable device or implant 200, such that the native leaflets coapt entirely around the coaptation member or coaptation element 210. This can, for example, improve sealing of the native leaflets 20, 22 and thus prevent or further reduce mitral regurgitation.

In some implementations the clasps comprise a moveable arm coupled to the anchors. In some implementations, the clasps 230 include a base or fixed arm 232, a moveable arm 234, barbs 236, and a joint portion 238. The fixed arms 232 are attached to the inner paddles 222, with the joint portion 238 disposed proximate the coaptation element 210. The joint portion 238 is spring-loaded so that the fixed and moveable arms 232, 234 are biased toward each other when the clasp 230 is in a closed condition. In some implementations, the clasps 230 include friction-enhancing elements or means for securing, such as barbs, protrusions, ridges, grooves, textured surfaces, adhesive, etc.

In some implementations, the fixed arms 232 are attached to the inner paddles 222 through holes or slots 231 with sutures (not shown). The fixed arms 232 can be attached to the inner paddles 222 with any suitable means, such as screws or other fasteners, crimped sleeves, mechanical latches or snaps, welding, adhesive, clamps, latches, or the like. The fixed arms 232 remain substantially stationary relative to the inner paddles 222 when the moveable arms 234 are opened to open the clasps 230 and expose the barbs or other friction-enhancing elements 236. The clasps 230 are opened by applying tension to actuation lines 216 (e.g., as shown in FIGS. 43-48) attached to holes 235 in the moveable arms 234, thereby causing the moveable arms 234 to articulate, pivot, and/or flex on the joint portions 238.

Figure 29:
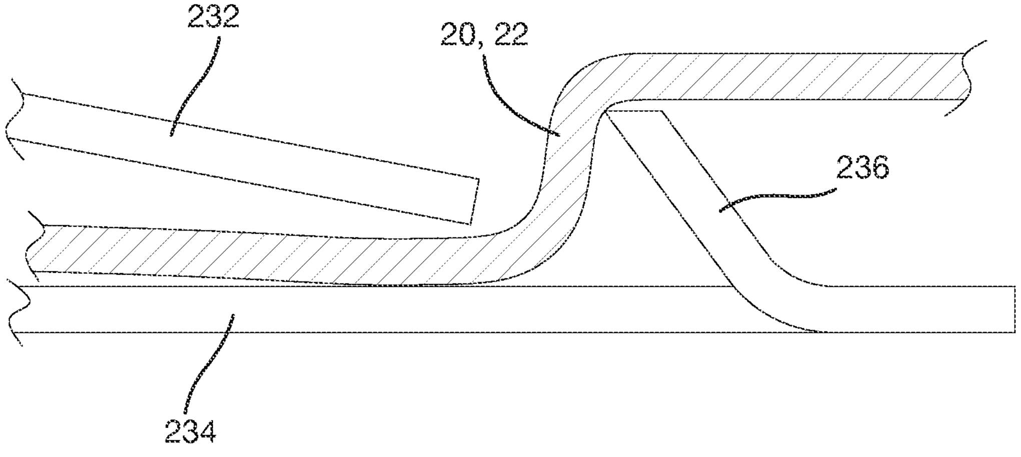
FIG. 29 shows a portion of native valve tissue grasped by a clasp.

Referring now to FIG. 29, a close-up view of one of the leaflets 20, 22 grasped by a clasp such as clasp 230 is shown. The leaflet 20, 22 is grasped between the moveable and fixed arms 234 of the clasp 230. The tissue of the leaflet 20, 22 is not pierced by the barbs or friction-enhancing elements 236, though in some implementations the barbs 236 may partially or fully pierce through the leaflet 20, 22. The angle and height of the barbs or friction-enhancing elements 236 relative to the moveable arm 234 helps to secure the leaflet 20, 22 within the clasp 230. In particular, a force pulling the implant off of the native leaflet 20, 22 will encourage the barbs or friction-enhancing elements 236 to further engage the tissue, thereby ensuring better retention. Retention of the leaflet 20, 22 in the clasp 230 is further improved by the position of fixed arm 232 near the barbs/friction-enhancing elements 236 when the clasp 230 is closed. In this arrangement, the tissue is formed by the fixed arms 232 and the moveable arms 234 and the barbs/friction-enhancing elements 236 into an S-shaped torturous path. Thus, forces pulling the leaflet 20, 22 away from the clasp 230 will encourage the tissue to further engage the barbs/friction-enhancing elements 236 before the leaflets 20, 22 can escape. For example, leaflet tension during diastole can encourage the barbs 236 to pull toward the end portion of the leaflet 20, 22. Thus, the S-shaped path can utilize the leaflet tension during diastole to engage the leaflets more tightly 20, 22 with the barbs/friction-enhancing elements 236.

Figure 25:
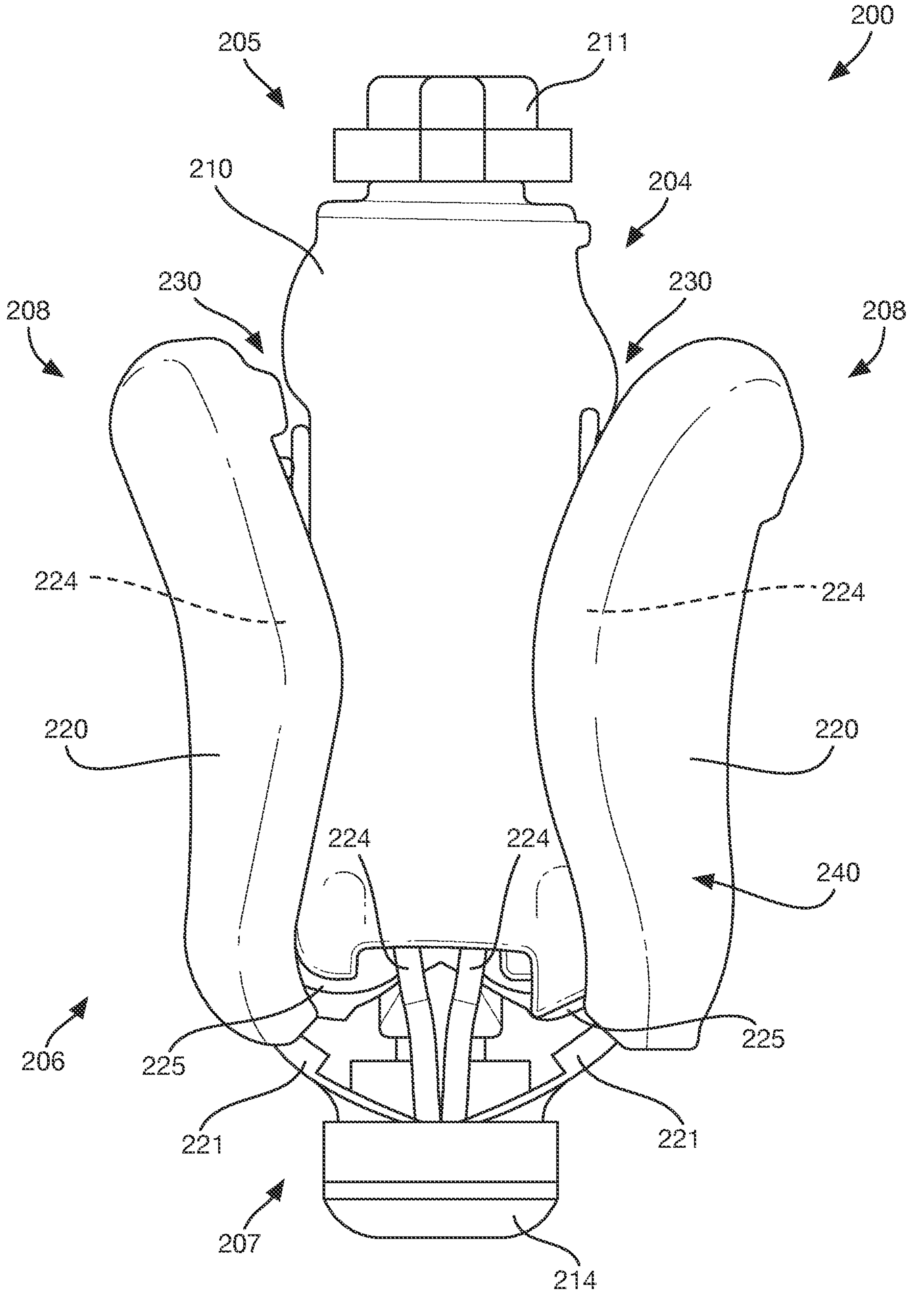
FIG. 25 shows a front view of the implantable device or implant of FIG. 22 with a cover covering the paddles and a coaptation element or spacer.
Figure 26:
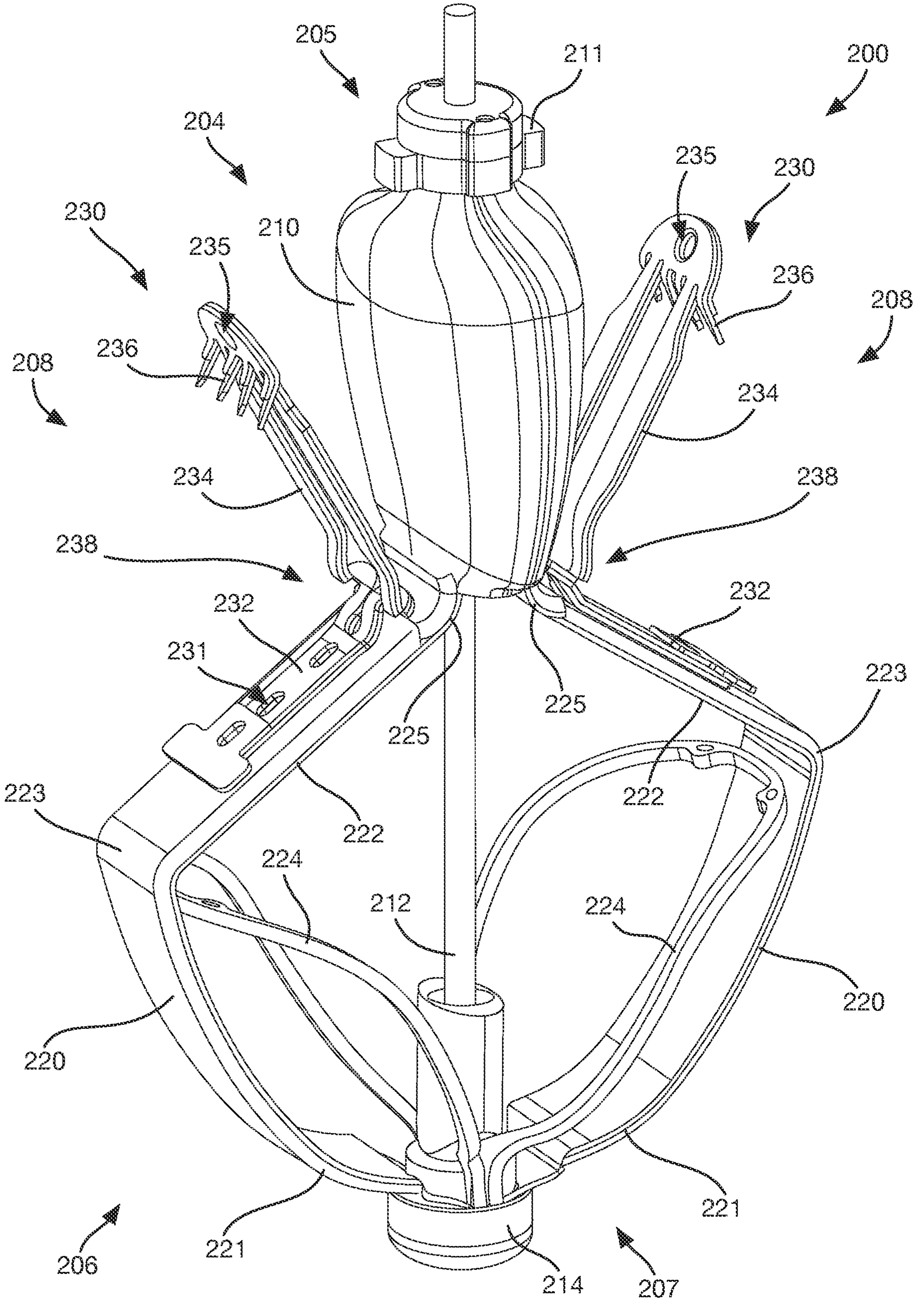
FIG. 26 shows a top perspective view of the implantable device or implant of FIG. 22 in an open position.
Figure 27:
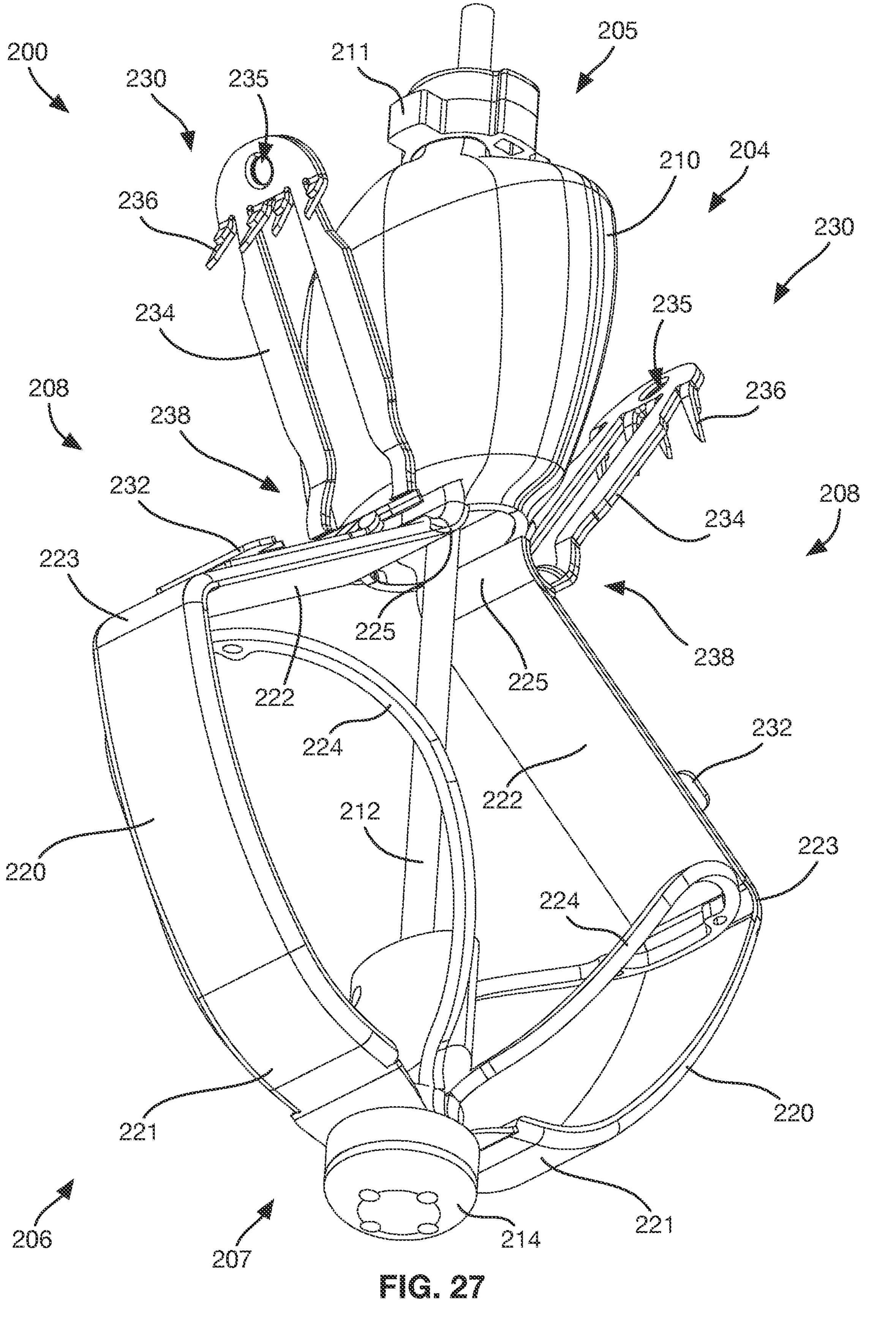
FIG. 27 shows a bottom perspective view of the implantable device or implant of FIG. 22 in an open position.
Figure 28:
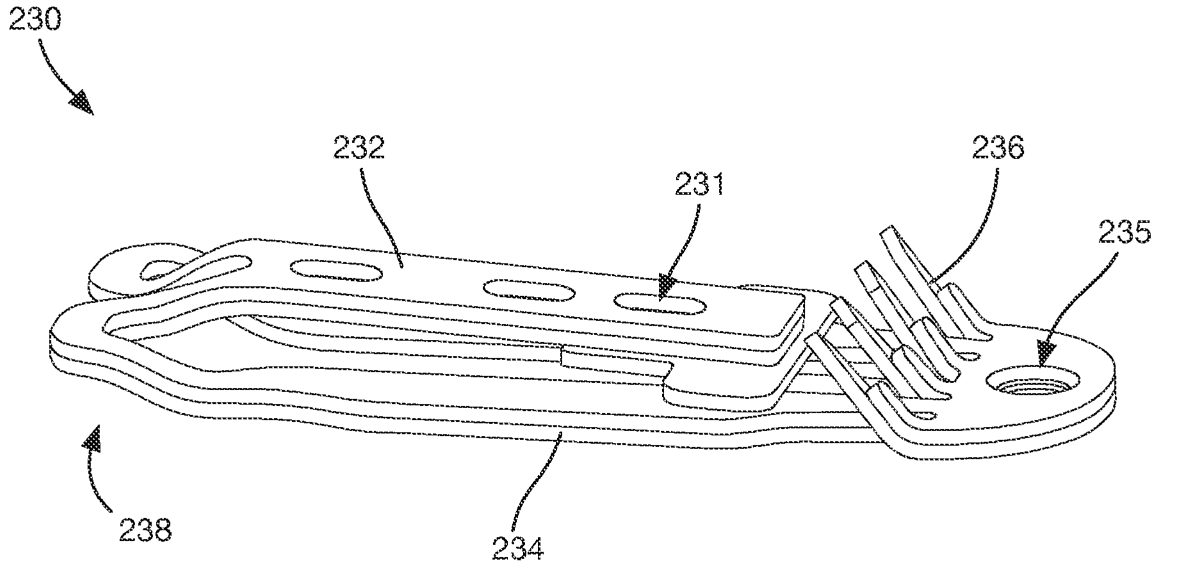
FIG. 28 shows a clasp for use in an implantable device or implant.

Referring to FIG. 25, the prosthetic device or implant 200 can also include a cover 240. In some implementations, the cover 240 can be disposed on the coaptation element 210, the outer and inner paddles 220, 222, and/or the paddle frames 224. The cover 240 can be configured to prevent or reduce blood-flow through the prosthetic device or implant 200 and/or to promote native tissue ingrowth. In some implementations, the cover 240 can be a cloth or fabric such as PET, velour, or other suitable fabric. In some implementations, in lieu of or in addition to a fabric, the cover 240 can include a coating (e.g., polymeric) that is applied to the implantable device or implant 200.

During implantation, the paddles 220, 222 of the anchors 208 are opened and closed to grasp the native valve leaflets 20, 22 between the paddles 220, 222 and the coaptation element 210. The anchors 208 are moved between a closed position (FIGS. 22-25) to various open positions (FIGS. 26-37) by extending and retracting the actuation element 212. Extending and retracting the actuation element 212 increases and decreases the spacing between the coaptation element 210 and the cap 214, respectively. The proximal collar 211 (or other attachment element) and the coaptation element 210 slide along the actuation element 212 during actuation so that changing of the spacing between the coaptation element 210 and the cap 214 causes the paddles 220, 220 to move between different positions to grasp the mitral valve leaflets 20, 22 during implantation.

As the device 200 is opened and closed, the pair of inner and outer paddles 222, 220 are moved in unison, rather than independently, by a single actuation element 212. Also, the positions of the clasps 230 are dependent on the positions of the paddles 222, 220. For example, the clasps 230 are arranged such that closure of the anchors 208 simultaneously closes the clasps 230. In some implementations, the device 200 can be made to have the paddles 220, 222 be independently controllable in the same manner (e.g., the device 100 illustrated in FIG. 15).

In some implementations, the clasps 230 further secure the native leaflets 20, 22 by engaging the leaflets 20, 22 with barbs and/or other friction-enhancing elements 236 and pinching the leaflets 20, 22 between the moveable and fixed arms 234, 232. In some implementations, the clasps 230 are barbed clasps that include barbs that increase friction with and/or may partially or completely puncture the leaflets 20, 22. The actuation lines 216 (FIGS. 43-48) can be actuated separately so that each clasp 230 can be opened and closed separately. Separate operation allows one leaflet 20, 22 to be grasped at a time, or for the repositioning of a clasp 230 on a leaflet 20, 22 that was insufficiently grasped, without altering a successful grasp on the other leaflet 20, 22. The clasps 230 can be fully opened and closed when the inner paddle 222 is not closed, thereby allowing leaflets 20, 22 to be grasped in a variety of positions as the particular situation requires.

Referring now to FIGS. 22-25, the device 200 is shown in a closed position. When closed, the inner paddles 222 are disposed between the outer paddles 220 and the coaptation element 210. The clasps 230 are disposed between the inner paddles 222 and the coaptation element 210. Upon successful capture of native leaflets 20, 22 the device 200 is moved to and retained in the closed position so that the leaflets 20, 22 are secured within the device 200 by the clasps 230 and are pressed against the coaptation element 210 by the paddles 220, 222. The outer paddles 220 can have a wide curved shape that fits around the curved shape of the coaptation element 210 to more securely grip the leaflets 20, 22 when the device 200 is closed (e.g., as can be seen in FIG. 51). The curved shape and rounded edges of the outer paddle 220 also prohibits or inhibits tearing of the leaflet tissue.

Referring now to FIGS. 30-37, the implantable device or implant 200 described above is shown in various positions and configurations ranging from partially open to fully open. The paddles 220, 222 of the device 200 transition between each of the positions shown in FIGS. 30-37 from the closed position shown in FIGS. 22-25 up extension of the actuation element 212 from a fully retracted to fully extended position.

Figure 30:
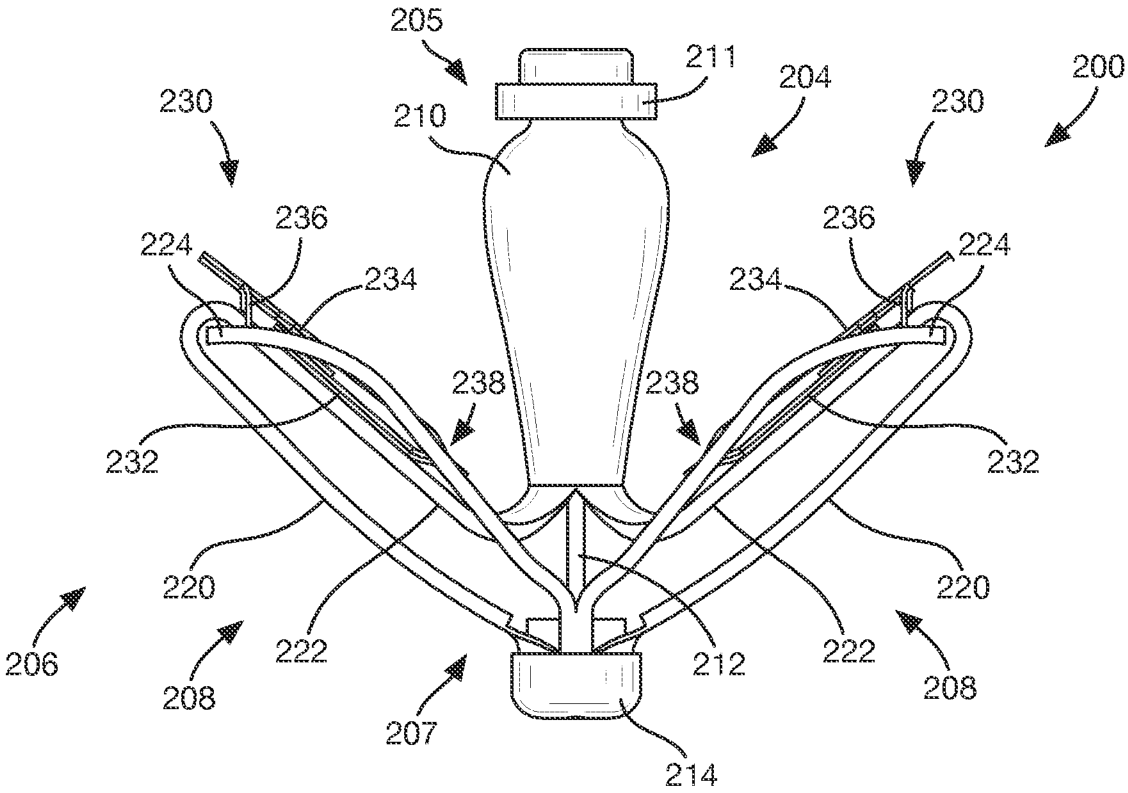
FIG. 30 shows a side view of an example implantable device or implant in a partially open position with clasps in a closed position.
Figure 31:
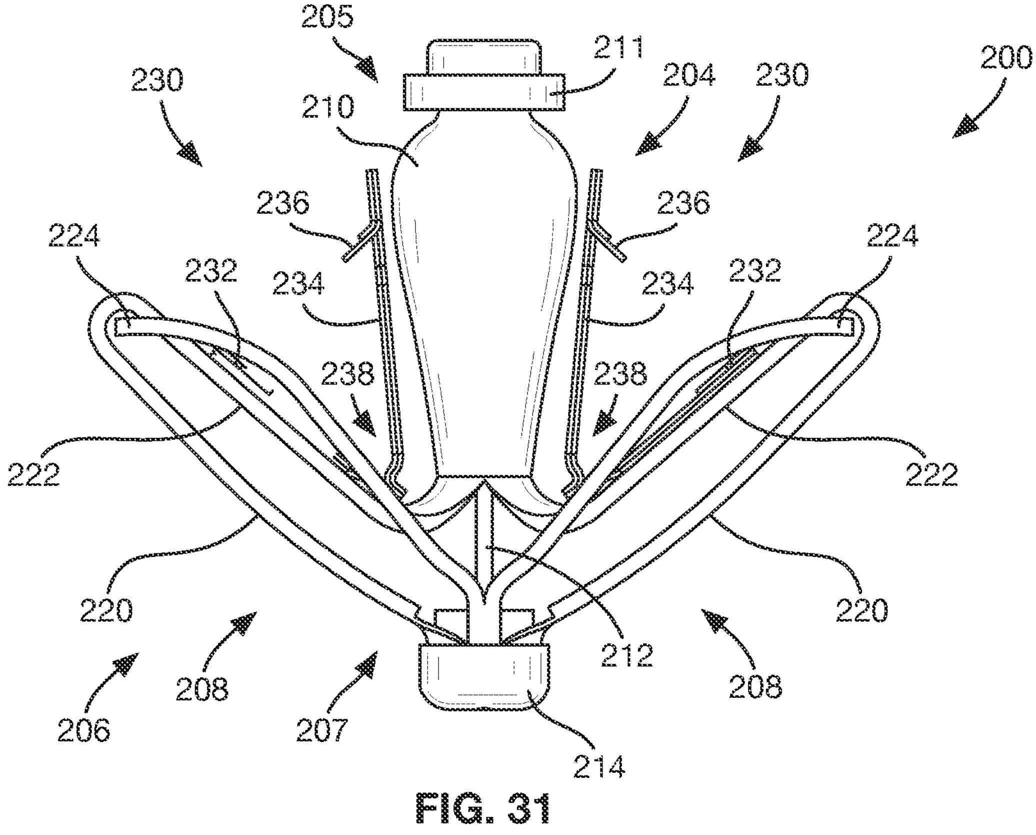
FIG. 31 shows a side view of an example implantable device or implant in a partially open position with clasps in an open position.

Referring now to FIGS. 30-31, the device 200 is shown in a partially open position. The device 200 is moved into the partially open position by extending the actuation element 212. Extending the actuation element 212 pulls down on the bottom portions of the outer paddles 220 and paddle frames 224. The outer paddles 220 and paddle frames 224 pull down on the inner paddles 222, where the inner paddles 222 are connected to the outer paddles 220 and the paddle frames 224. Because the proximal collar 211 (or other attachment element) and coaptation element 210 are held in place by the capture mechanism 213, the inner paddles 222 are caused to articulate, pivot, and/or flex in an opening direction. The inner paddles 222, the outer paddles 220, and the paddle frames all flex to the position shown in FIGS. 30-31. Opening the paddles 222, 220 and frames 224 forms a gap between the coaptation element 210 and the inner paddle 222 that can receive and grasp the native leaflets 20, 22. This movement also exposes the clasps 230 that can be moved between closed (FIG. 30) and open (FIG. 31) positions to form a second gap for grasping the native leaflets 20, 22. The extent of the gap between the fixed and moveable arms 232, 234 of the clasp 230 is limited to the extent that the inner paddle 222 has spread away from the coaptation element 210.

Figure 32:
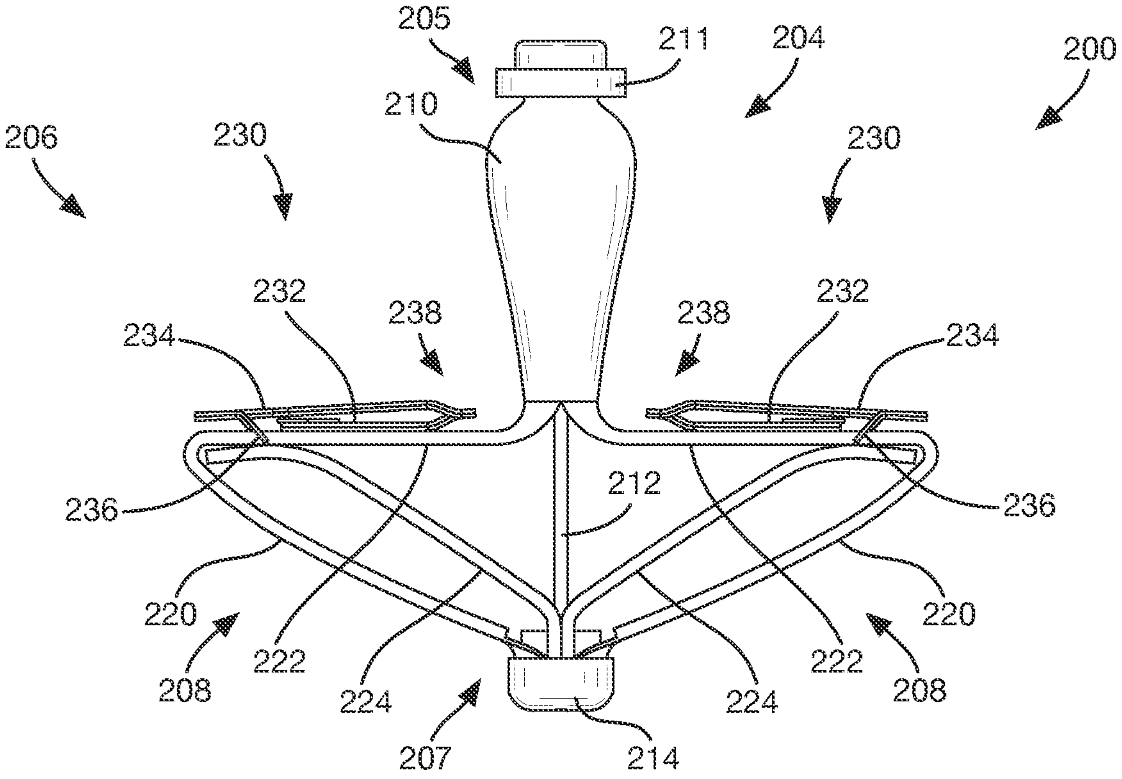
FIG. 32 shows a side view of an example implantable device or implant in a half-open position with clasps in a closed position.
Figure 33:
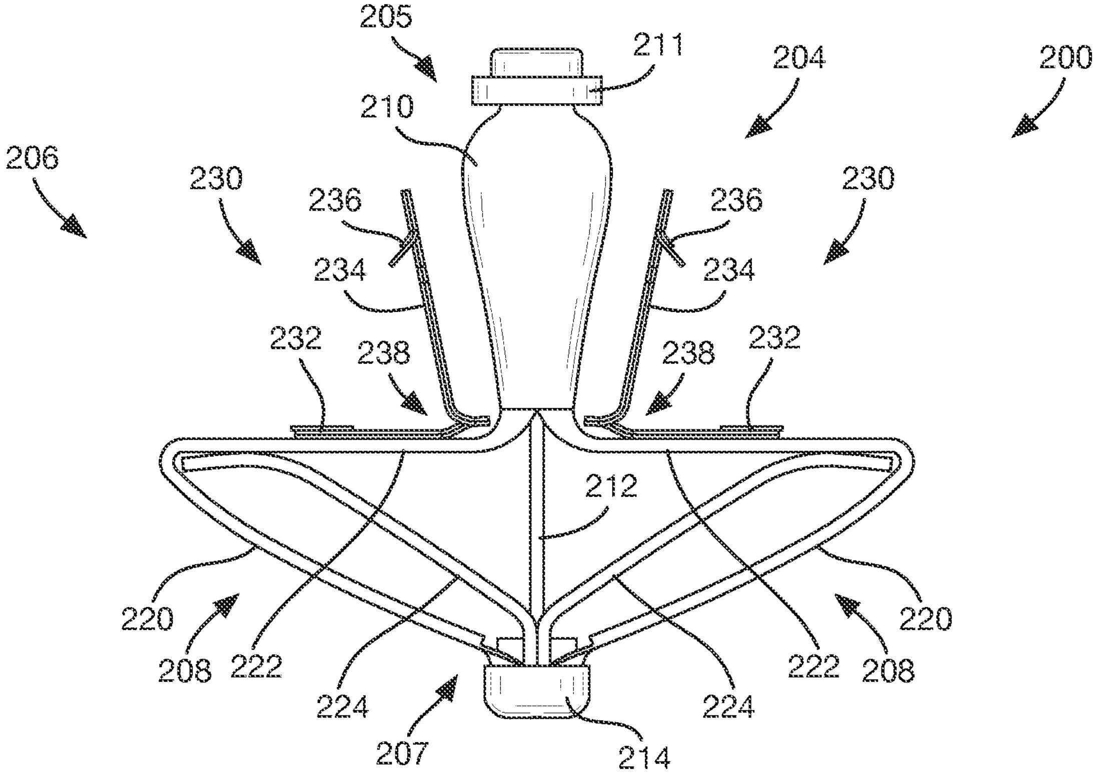
FIG. 33 shows a side view of an example implantable device or implant in a half-open position with clasps in an open position.

Referring now to FIGS. 32-33, the device 200 is shown in a laterally extended or open position. The device 200 is moved into the laterally extended or open position by continuing to extend the actuation element 212 described above, thereby increasing the distance between the coaptation element 210 and the cap 214 of the distal portion 207. Continuing to extend the actuation element 212 pulls down on the outer paddles 220 and paddle frames 224, thereby causing the inner paddles 222 to spread apart further from the coaptation element 210. In the laterally extended or open position, the inner paddles 222 extend horizontally more than in other positions of the device 200 and form an approximately 90-degree angle with the coaptation element 210. Similarly, the paddle frames 224 are at their maximum spread position when the device 200 is in the laterally extended or open position. The increased gap between the coaptation element 210 and inner paddle 222 formed in the laterally extended or open position allows clasps 230 to open further (FIG. 33) before engaging the coaptation element 210, thereby increasing the size of the gap between the fixed and moveable arms 232, 234.

Figure 34:
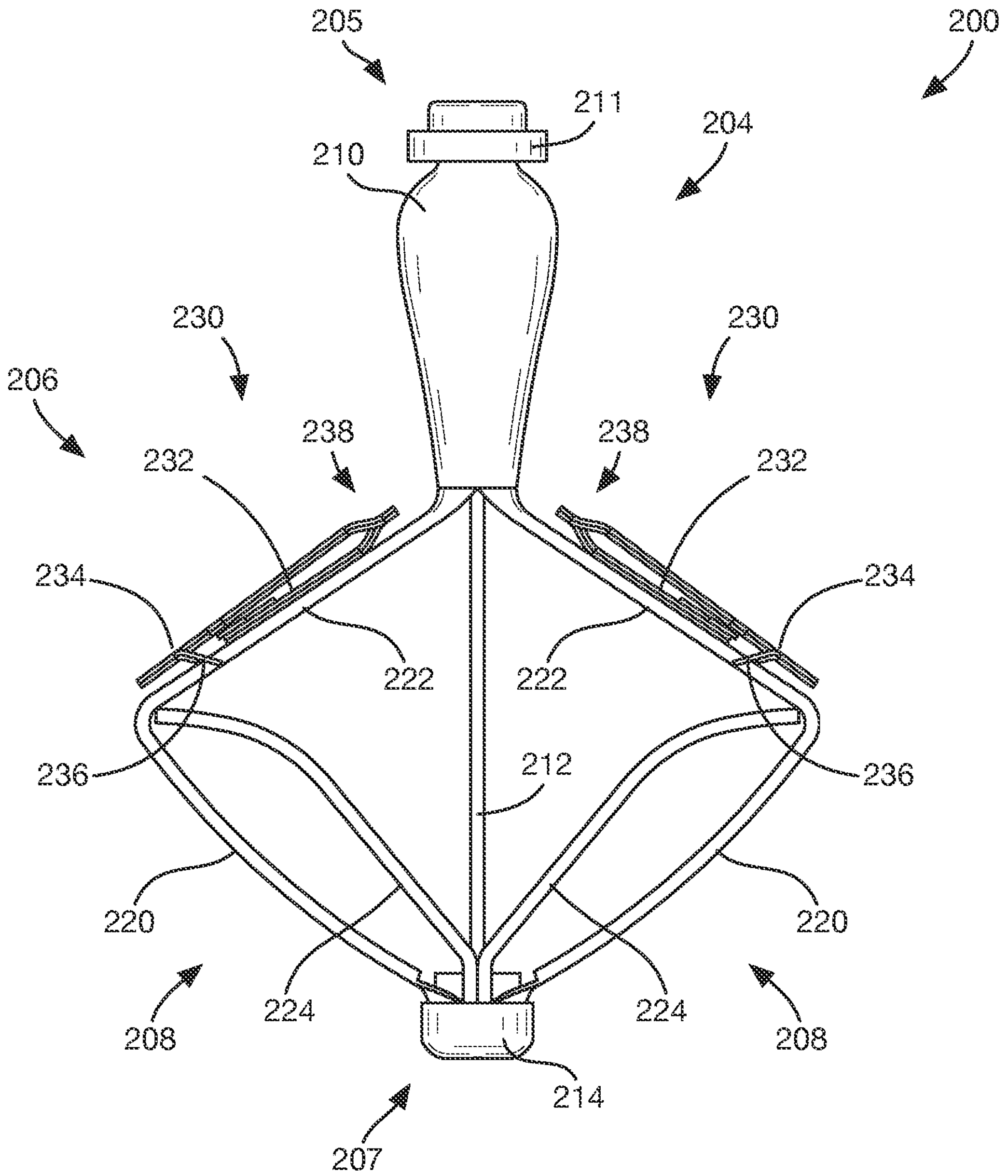
FIG. 34 shows a side view of an example implantable device or implant in a three-quarters-open position with clasps in a closed position.
Figure 35:
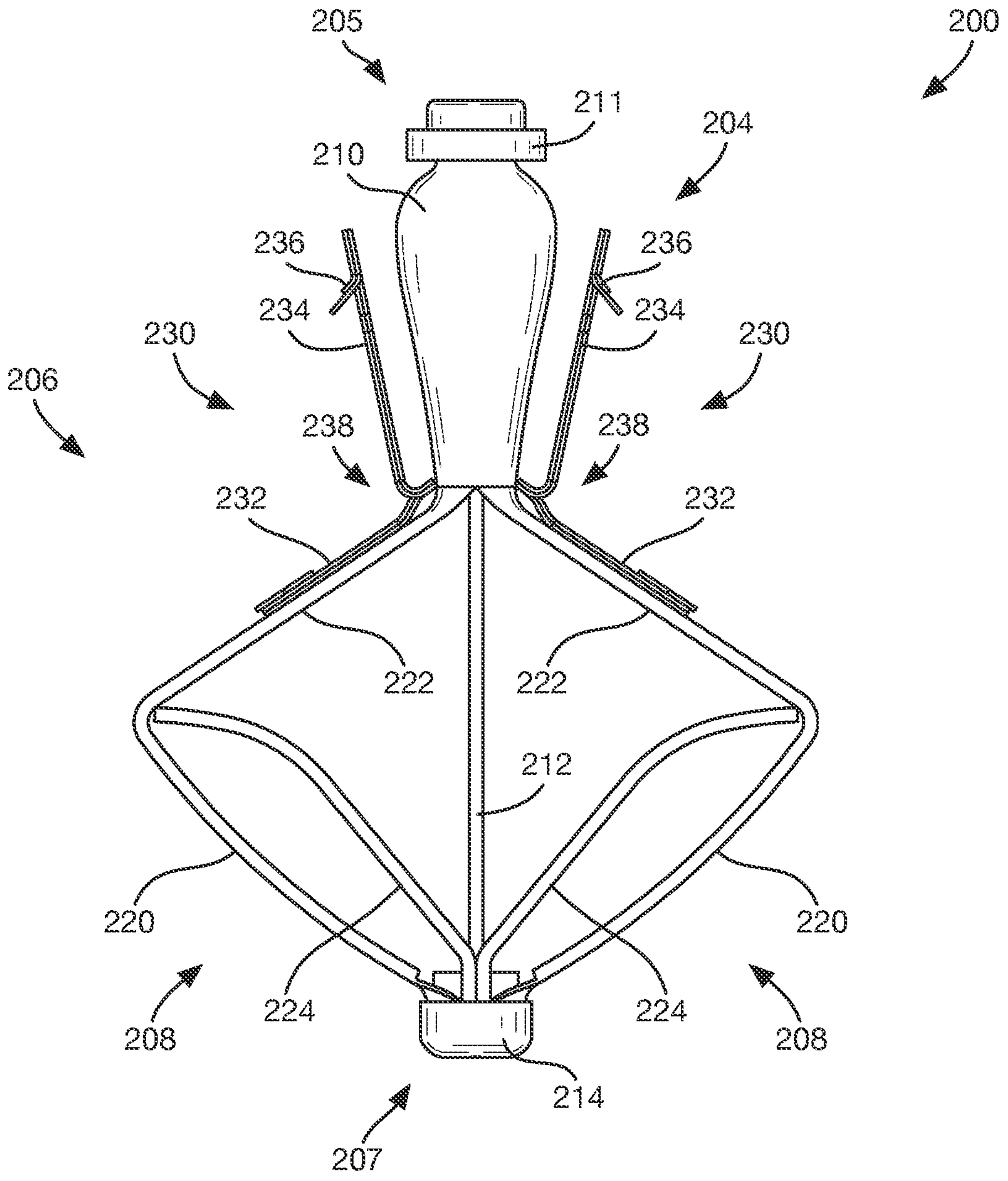
FIG. 35 shows a side view of an example implantable device or implant in a three-quarters-open position with clasps in an open position.

Referring now to FIGS. 34-35, the example device 200 is shown in a three-quarters extended position. The device 200 is moved into the three-quarters extended position by continuing to extend the actuation element 212 described above, thereby increasing the distance between the coaptation element 210 and the cap 214 of the distal portion 207. Continuing to extend the actuation element 212 pulls down on the outer paddles 220 and paddle frames 224, thereby causing the inner paddles 222 to spread apart further from the coaptation element 210. In the three-quarters extended position, the inner paddles 222 are open beyond 90 degrees to an approximately 135-degree angle with the coaptation element 210. The paddle frames 224 are less spread than in the laterally extended or open position and begin to move inward toward the actuation element 212 as the actuation element 212 extends further. The outer paddles 220 also flex back toward the actuation element 212. As with the laterally extended or open position, the increased gap between the coaptation element 210 and inner paddle 222 formed in the laterally extended or open position allows clasps 230 to open even further (FIG. 35), thereby increasing the size of the gap between the fixed and moveable arms 232, 234.

Figure 36:
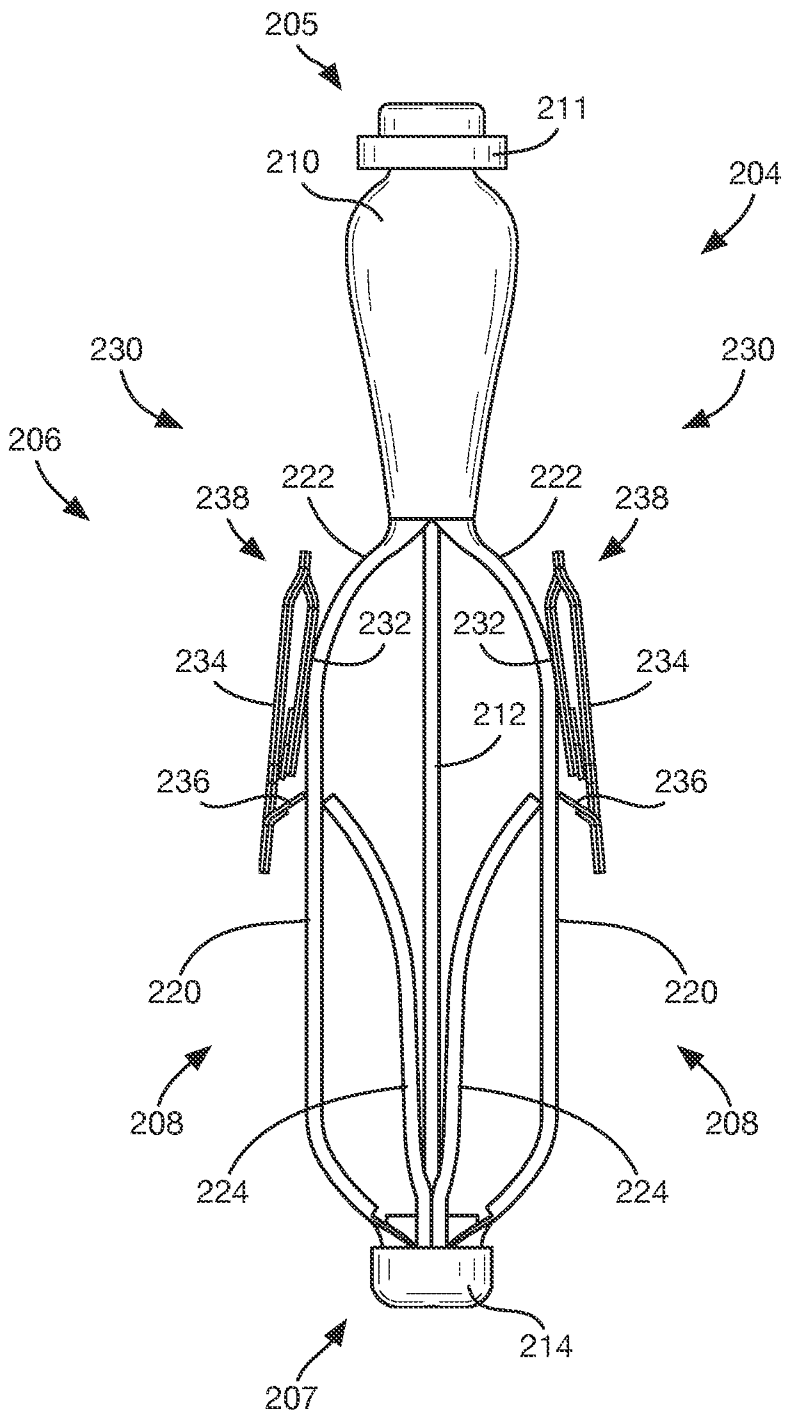
FIG. 36 shows a side view of an example implantable device in a fully open or full bailout position with clasps in a closed position.
Figure 37:
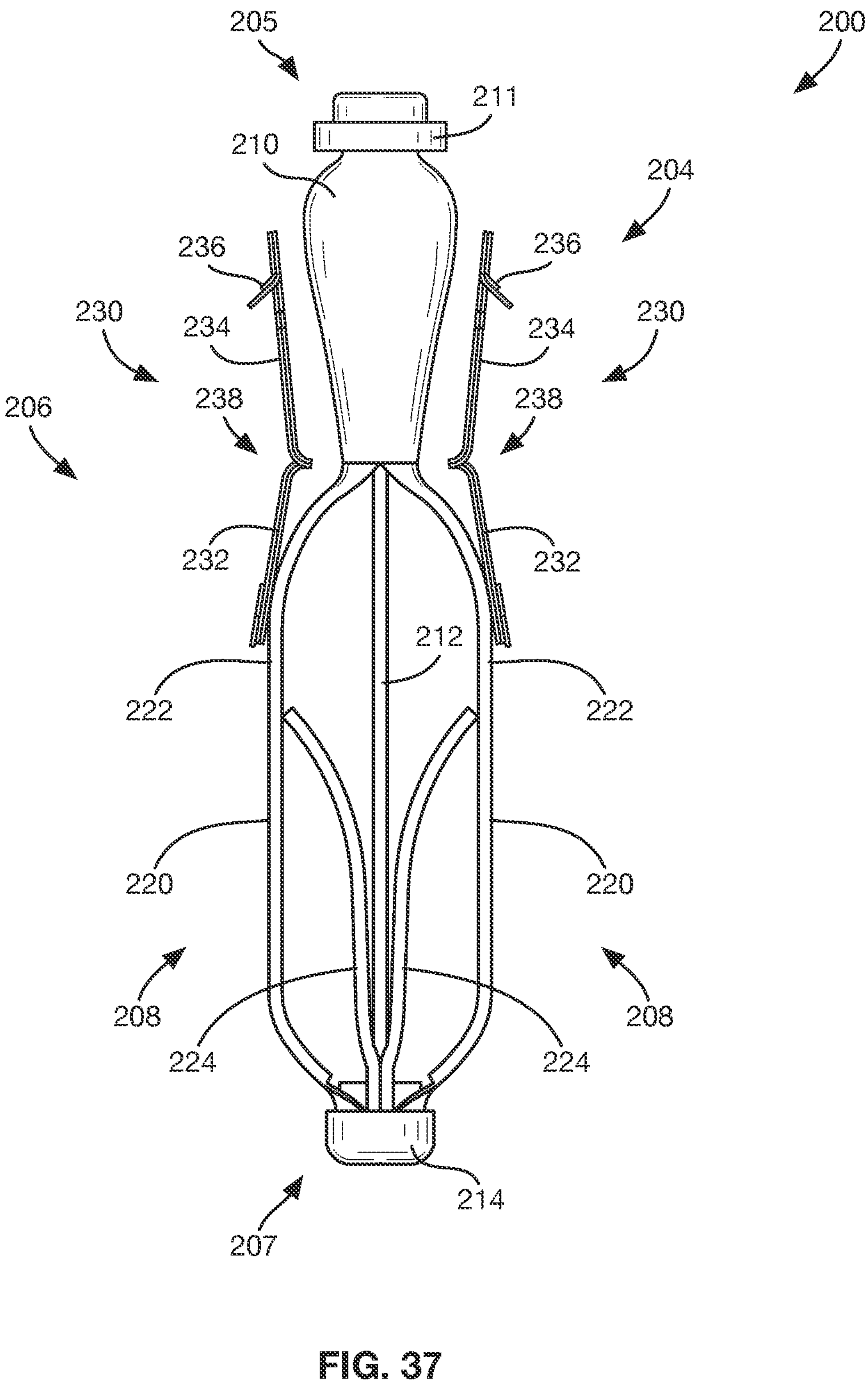
FIG. 37 shows a side view of an example implantable device in a fully open or full bailout position with clasps in an open position.

Referring now to FIGS. 36-37, the example device 200 is shown in a fully extended position. The device 200 is moved into the fully extended position by continuing to extend the actuation element 212 described above, thereby increasing the distance between the coaptation element 210 and the cap 214 of the distal portion 207 to a maximum distance allowable by the device 200. Continuing to extend the actuation element 212 pulls down on the outer paddles 220 and paddle frames 224, thereby causing the inner paddles 222 to spread apart further from the coaptation element 210. The outer paddles 220 and paddle frames 224 move to a position where they are close to the actuation element. In the fully extended position, the inner paddles 222 are open to an approximately 180-degree angle with the coaptation element 210. The inner and outer paddles 222, 220 are stretched straight in the fully extended position to form an approximately 180-degree angle between the paddles 222, 220. The fully extended position of the device 200 provides the maximum size of the gap between the coaptation element 210 and inner paddle 222, and, in some implementations, allows clasps 230 to also open fully to approximately 180 degrees (FIG. 37) between the fixed and moveable arms 232, 234 of the clasp 230. The position of the device 200 is the longest and the narrowest configuration. Thus, the fully extended position of the device 200 may be a desirable position for bailout of the device 200 from an attempted implantation or may be a desired position for placement of the device in a delivery catheter, or the like.

Configuring the prosthetic device or implant 200 such that the anchors 208 can extend to a straight or approximately straight configuration (e.g., approximately 120-180 degrees relative to the coaptation element 210) can provide several advantages. For example, this configuration can reduce the radial crimp profile of the prosthetic device or implant 200. It can also make it easier to grasp the native leaflets 20, 22 by providing a larger opening between the coaptation element 210 and the inner paddles 222 in which to grasp the native leaflets 20, 22. Additionally, the relatively narrow, straight configuration can prevent or reduce the likelihood that the prosthetic device or implant 200 will become entangled in native anatomy (e.g., chordae tendineae CT shown in FIGS. 3 and 4) when positioning and/or retrieving the prosthetic device or implant 200 into the delivery system 202.

Referring now to FIGS. 38-49, an example implantable device 200 is shown being delivered and implanted within the native mitral valve MV of the heart H. As described above, the device 200 shown in FIGS. 38-49 includes the optional covering 240 (e.g., FIG. 25) over the coaptation element 210, clasps 230, inner paddles 222 and/or the outer paddles 220. The device 200 is deployed from a delivery system 202 (e.g., which can comprise an implant catheter that is extendable from a steerable catheter and/or a guide sheath) and is retained by a capture mechanism 213 (see e.g., FIGS. 43 and 48) and is actuated by extending or retracting the actuation element 212. Fingers of the capture mechanism 213 removably attach the collar 211 to the delivery system 202. In some implementations, the capture mechanism 213 is held closed around the collar 211 by the actuation element 212, such that removal of the actuation element 212 allows the fingers of the capture mechanism 213 to open and release the collar 211 to decouple the capture mechanism 213 from the device 200 after the device 200 has been successfully implanted.

Figure 38:
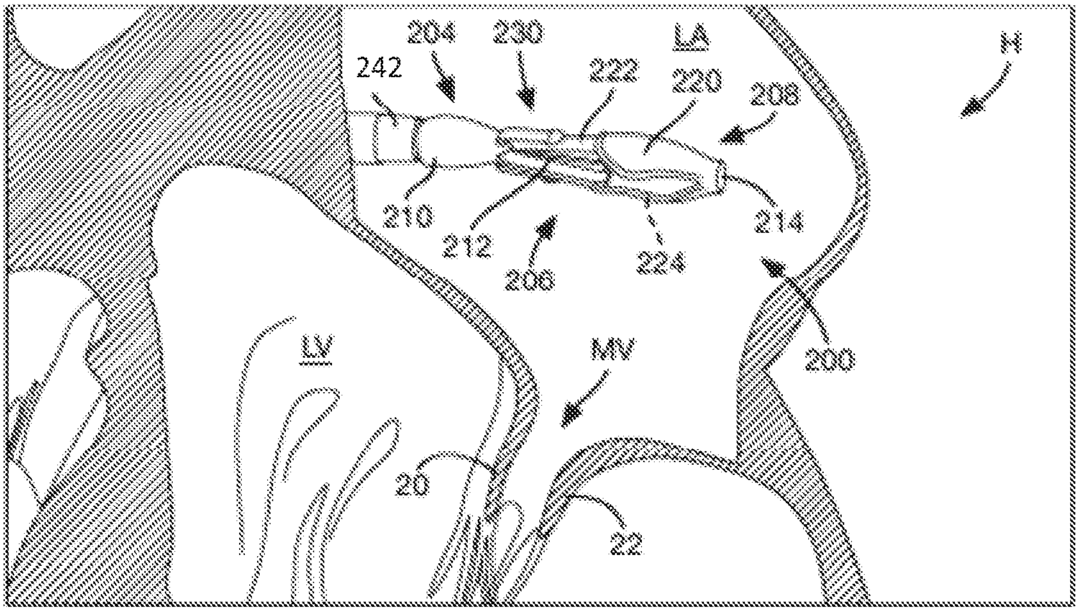
FIGS. 38-49 show the example implantable device or implant of FIGS. 30-38, including a cover, being delivered, and implanted within a native valve.
Figure 39:
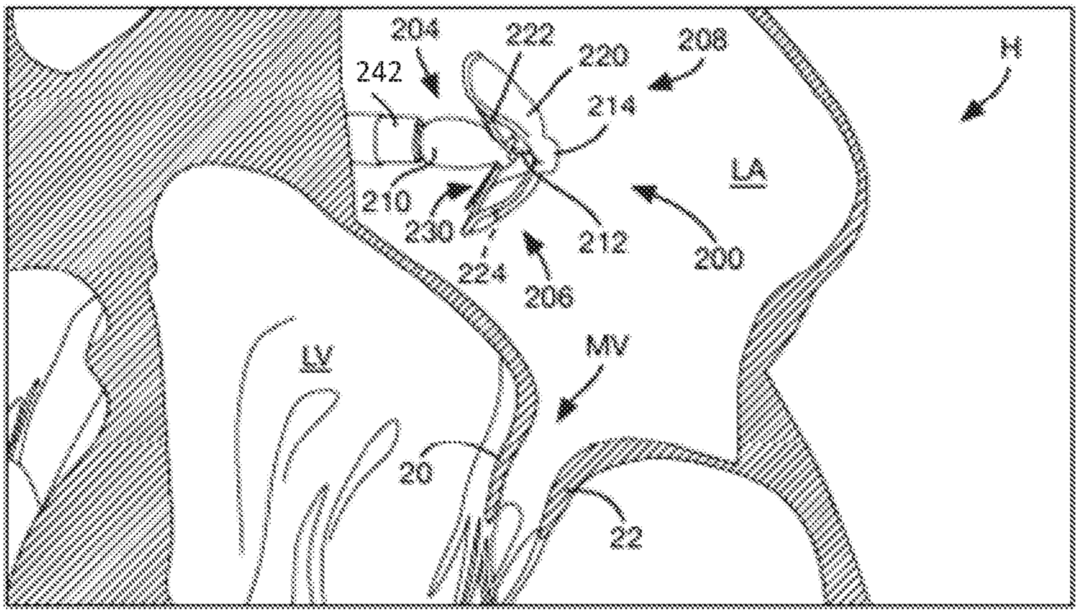
Figure 40:
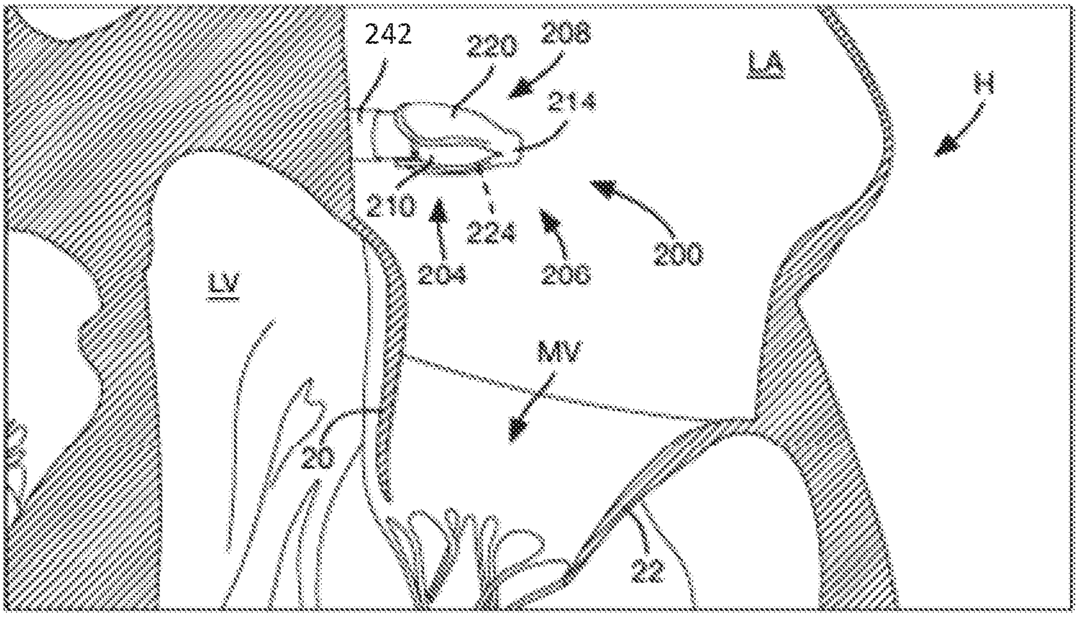
Figure 41:
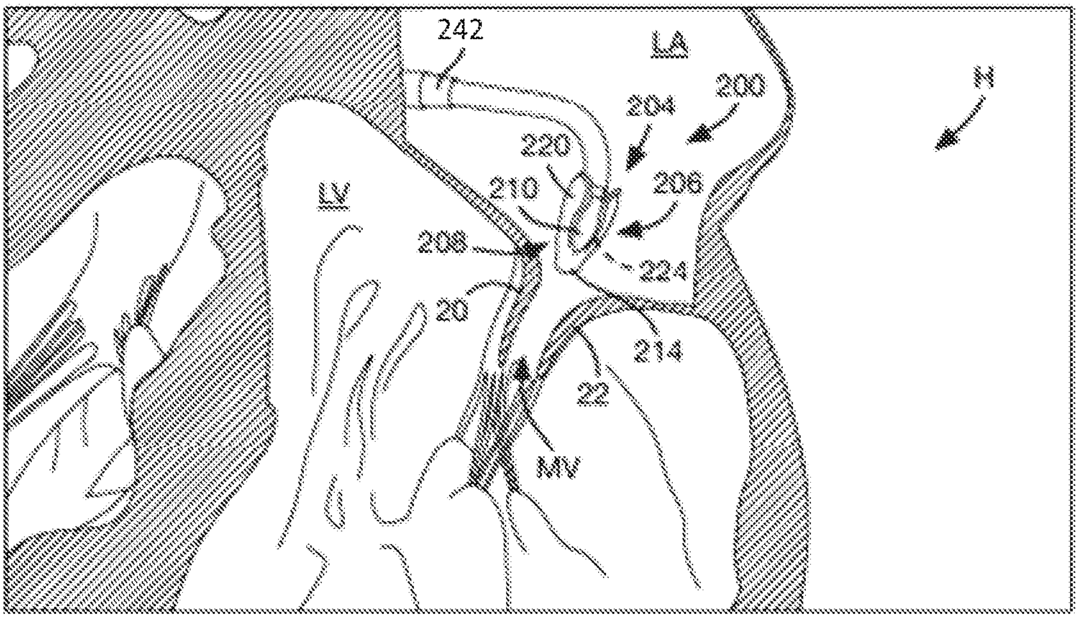
Figure 42:
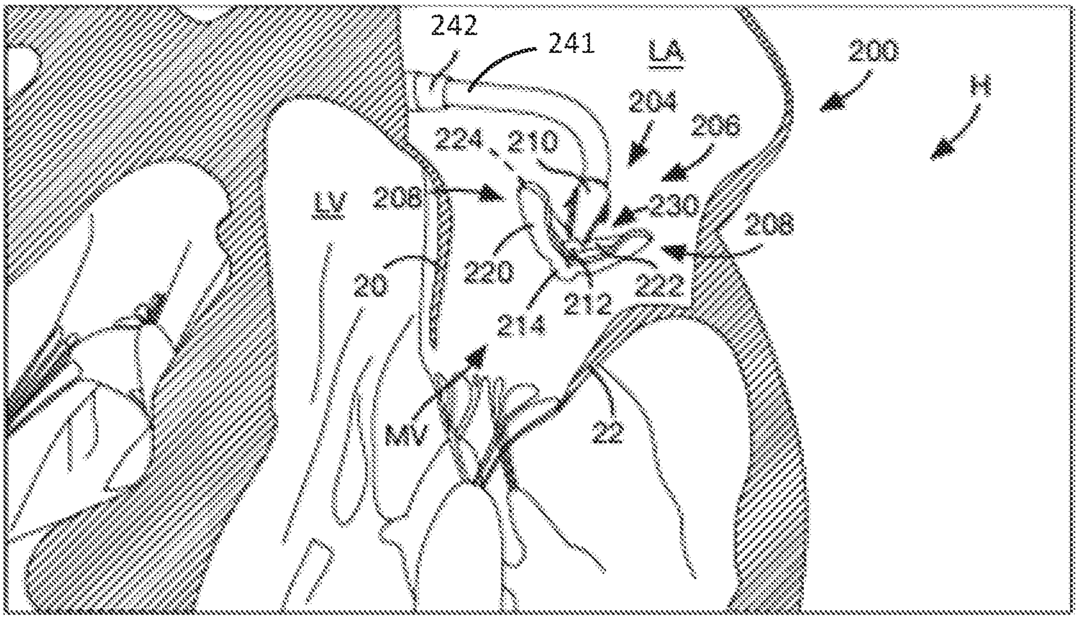
Figure 43:
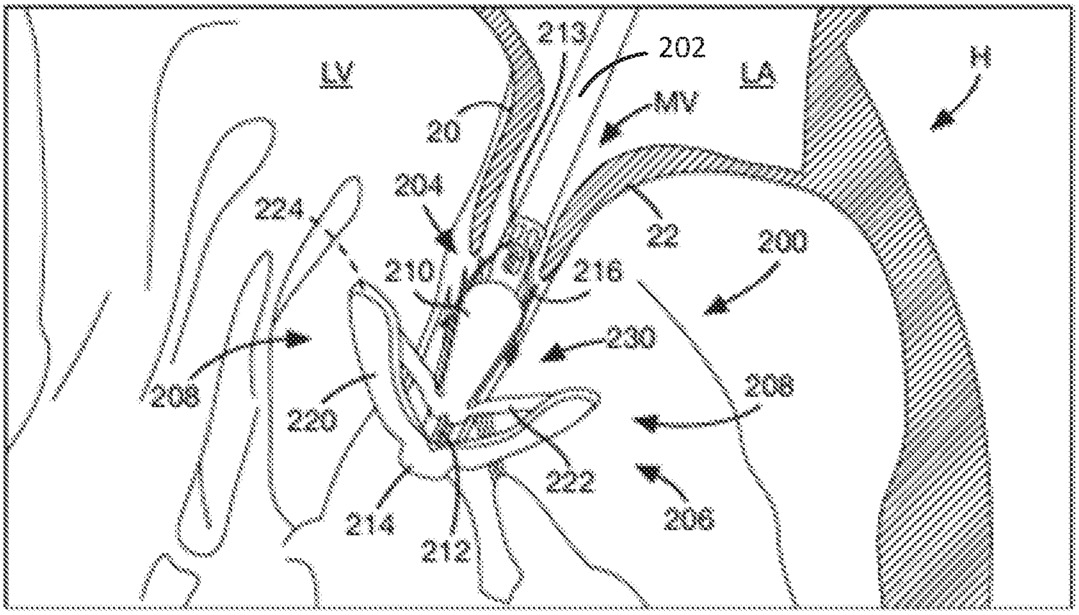
Figure 44:
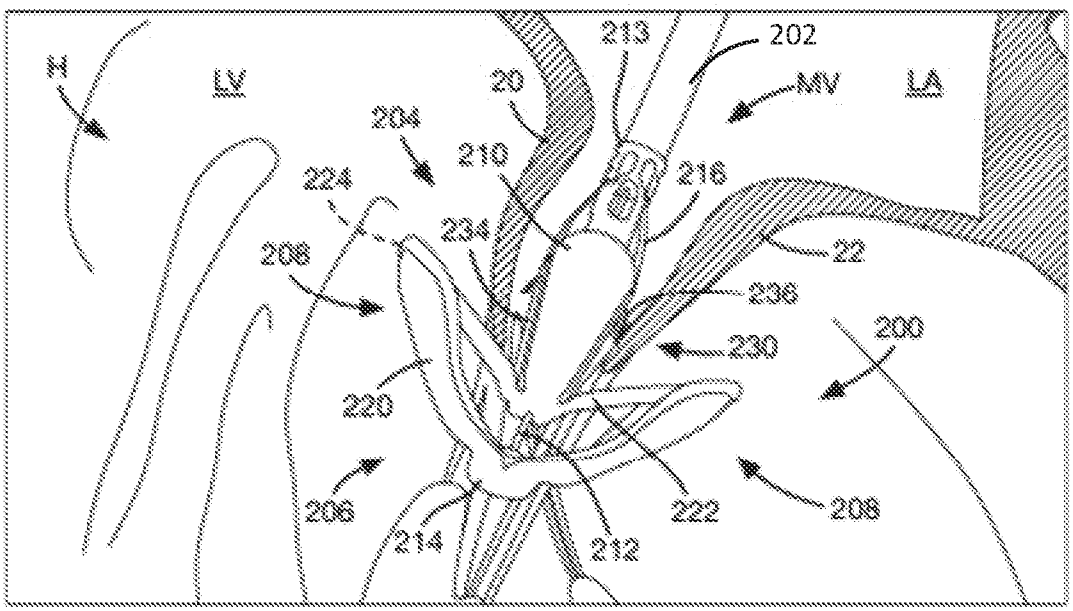

Referring now to FIG. 38, the delivery system 202 (e.g., a delivery catheter/sheath thereof) is inserted into the left atrium LA through the septum and the device/implant 200 is deployed from the delivery system 202 (e.g., an implant catheter retaining the device/implant can be extended to deploy the device/implant out from a steerable catheter) in the fully open condition for the reasons discussed above with respect to the device 100. The actuation element 212 is then retracted to move the device 200 through the partially closed condition (FIG. 39) and to the fully closed condition shown in FIGS. 40-41. Then the delivery system or catheter maneuvers the device/implant 200 towards the mitral valve MV as shown in FIG. 41. Referring now to FIG. 42, when the device 200 is aligned with the mitral valve MV, the actuation element 212 is extended to open the paddles 220, 222 into the partially opened position and the actuation lines 216 (FIGS. 43-48) are retracted to open the clasps 230 to prepare for leaflet grasp. Next, as shown in FIGS. 43-44, the partially open device 200 is inserted through the native valve (e.g., by advancing an implant catheter from a steerable catheter) until leaflets 20, 22 are properly positioned in between the inner paddles 222 and the coaptation element 210 and inside the open clasps 230.

Figure 45:
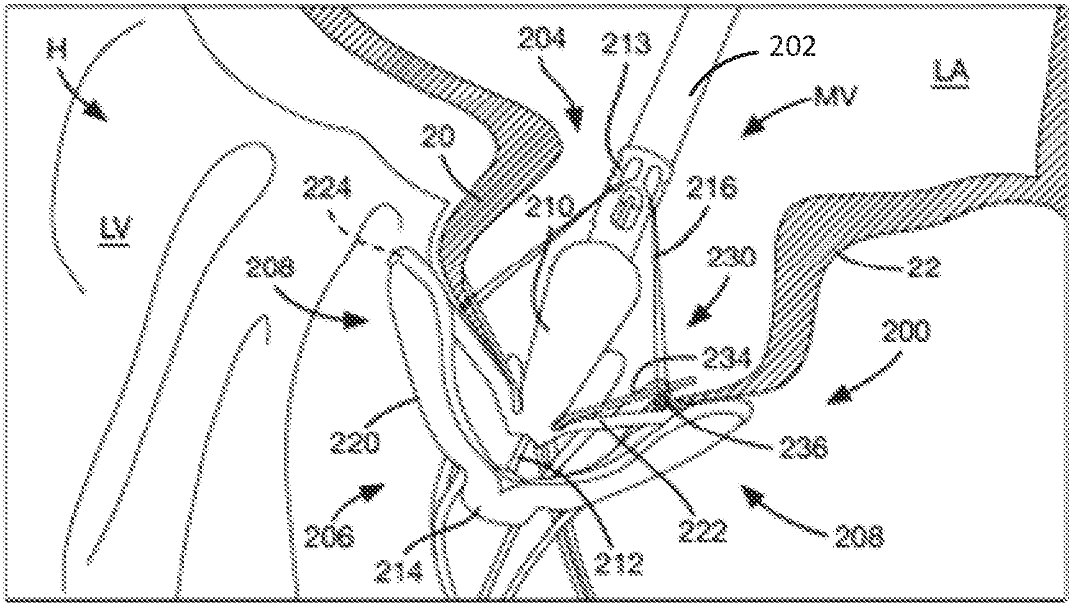
Figure 46:
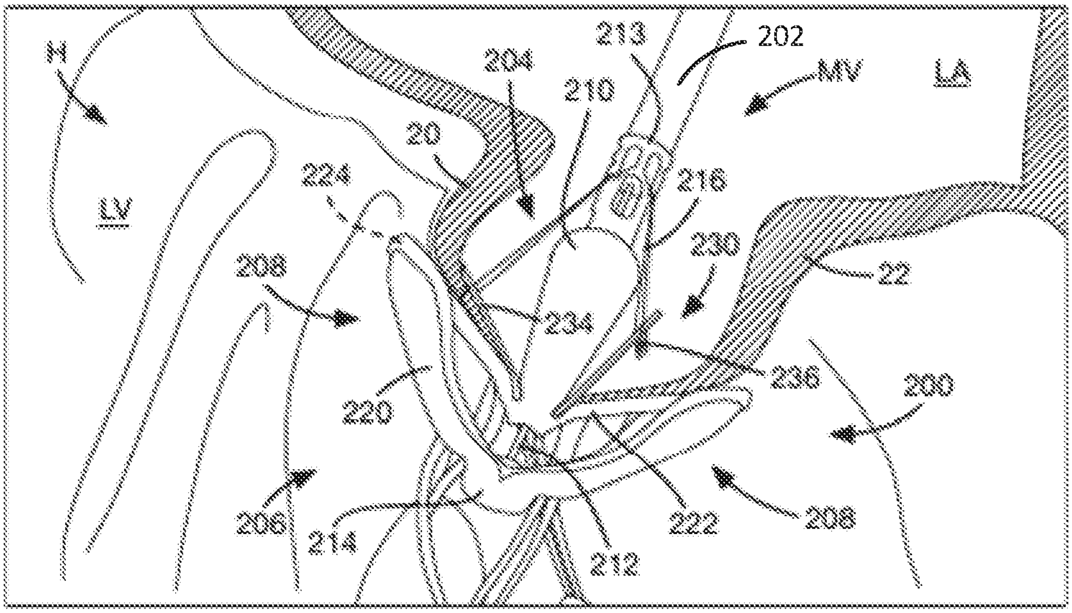
Figure 47:
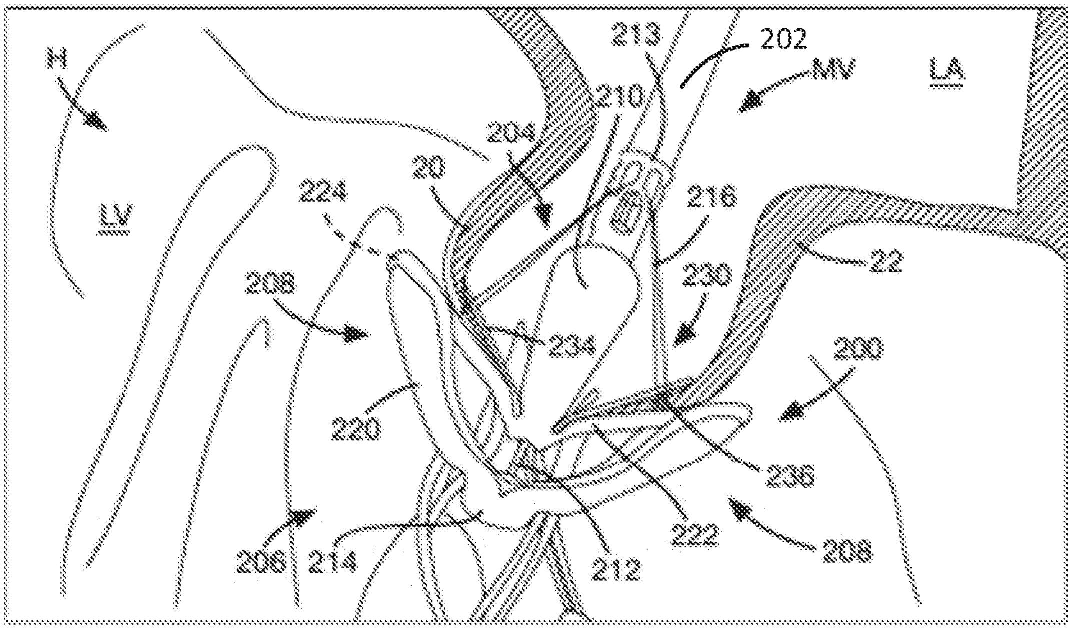
Figure 48:
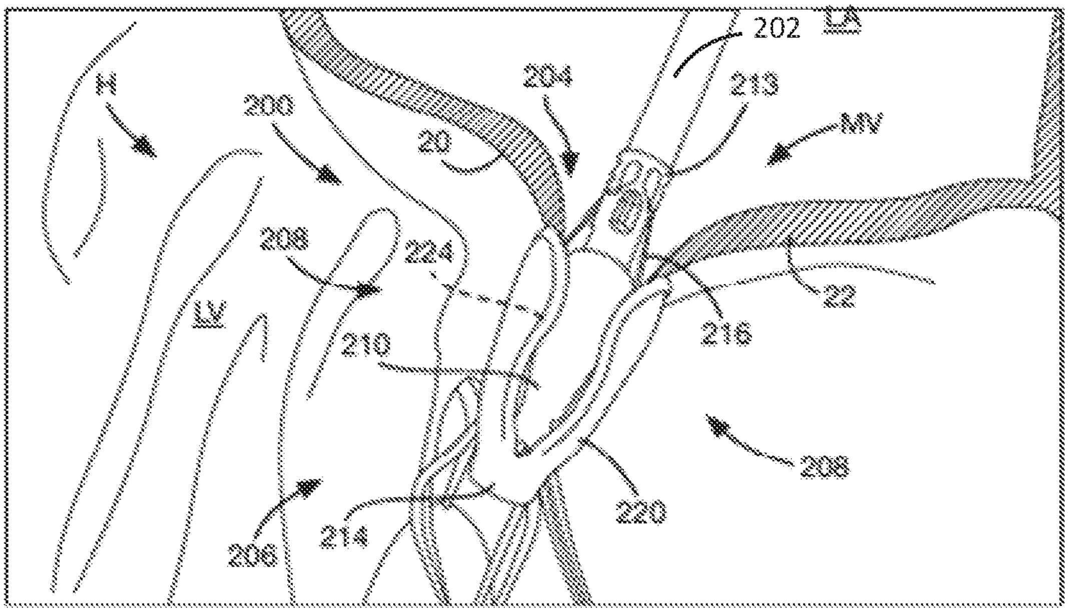
Figure 49:
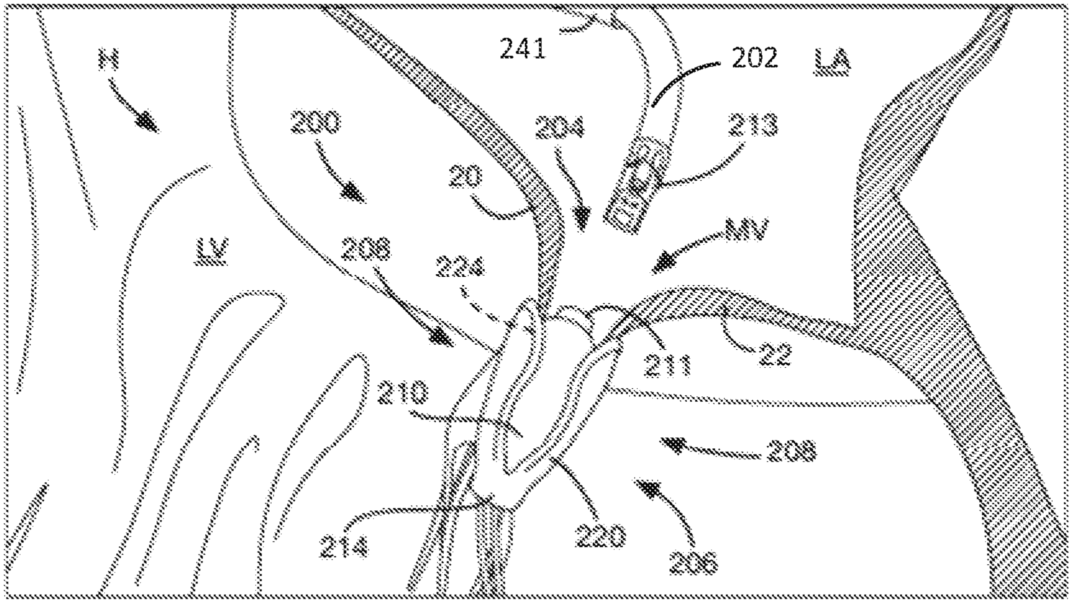

FIG. 45 shows the device 200 with both clasps 230 closed, though the barbs 236 of one clasp 230 missed one leaflet 22. As can be seen in FIGS. 45-47, the out of position clasp 230 is opened and closed again to properly grasp the missed leaflet 22. When both leaflets 20, 22 are grasped properly, the actuation element 212 is retracted to move the device 200 into the fully closed position shown in FIG. 48. With the device 200 fully closed and implanted in the native valve, the actuation element 212 is disengaged from the cap 214 and is withdrawn to release the capture mechanism 213 from the proximal collar 211 (or other attachment element) so that the capture mechanism 213 can be withdrawn into the delivery system 202 (e.g., into a catheter/sheath), as shown in FIG. 49. Once deployed, the device 200 can be maintained in the fully closed position with a mechanical means such as a latch or may be biased to remain closed through the use of spring material, such as steel, and/or shape-memory alloys such as Nitinol. For example, the paddles 220, 222 can be formed of steel or Nitinol shape-memory alloy—produced in a wire, sheet, tubing, or laser sintered powder—and are biased to hold the outer paddles 220 closed around the inner paddles 222, coaptation element 210, and/or the clasps 230 pinched around native leaflets 20, 22.

Referring to FIGS. 50-54, once the device 200 is implanted in a native valve, the coaptation element 210 functions as a gap filler in the valve regurgitant orifice, such as the gap 26 in the mitral valve MV illustrated by FIG. 6 or a gap in another native valve. In some implementations, when the device 200 has been deployed between the two opposing valve leaflets 20, 22, the leaflets 20, 22 no longer coapt against each other in the area of the coaptation element 210, but instead coapt against the coaptation element 210. This reduces the distance the leaflets 20, 22 need to be approximated to close the mitral valve MV during systole, thereby facilitating repair of functional valve disease that may be causing mitral regurgitation. A reduction in leaflet approximation distance can result in several other advantages as well. For example, the reduced approximation distance required of the leaflets 20, 22 reduces or minimizes the stress experienced by the native valve. Shorter approximation distance of the valve leaflets 20,22 can also require less approximation forces which can result in less tension experienced by the leaflets 20, 22 and less diameter reduction of the valve annulus. The smaller reduction of the valve annulus—or none at all—can result in less reduction in valve orifice area as compared to a device without a coaptation element or spacer. In this way, the coaptation element 210 can reduce the transvalvular gradients.

To adequately fill the gap 26 between the leaflets 20, 22, the device 200 and the components thereof can have a wide variety of different shapes and sizes. For example, the outer paddles 220 and paddle frames 224 can be configured to conform to the shape or geometry of the coaptation element 210 as is shown in FIGS. 50-54. As a result, the outer paddles 220 and paddle frames 224 can mate with both the coaptation element 210 and the native valve leaflets 20, 22. In some implementations, when the leaflets 20, 22 are coapted against the coaptation element 210, the leaflets 20, 22 fully surround or "hug" the coaptation element 210 in its entirety, thus small leaks at lateral and medial aspects 201, 203 of the coaptation element 210 can be prevented. The interaction of the leaflets 20, 22 and the device 200 is made clear in FIG. 51, which shows a schematic atrial or surgeon's view that shows the paddle frame 224 (which would not actually be visible from a true atrial view, e.g., FIG. 52), conforming to the coaptation element 210 geometry. The opposing leaflets 20, 22 (the ends of which would also not be visible in the true atrial view, e.g., FIG. 52) being approximated by the paddle frames 224, to fully surround or "hug" the coaptation element 210.

This coaptation of the leaflets 20, 22 against the lateral and medial aspects 201, 203 of the coaptation element 210 (shown from the atrial side in FIG. 52, and the ventricular side in FIG. 53) would seem to contradict the statement above that the presence of a coaptation element 210 minimizes the distance the leaflets need to be approximated. However, the distance the leaflets 20, 22 need to be approximated is still minimized if the coaptation element 210 is placed precisely at a regurgitant gap 26 and the regurgitant gap 26 is less than the width (medial-lateral) of the coaptation element 210.

Figure 50:
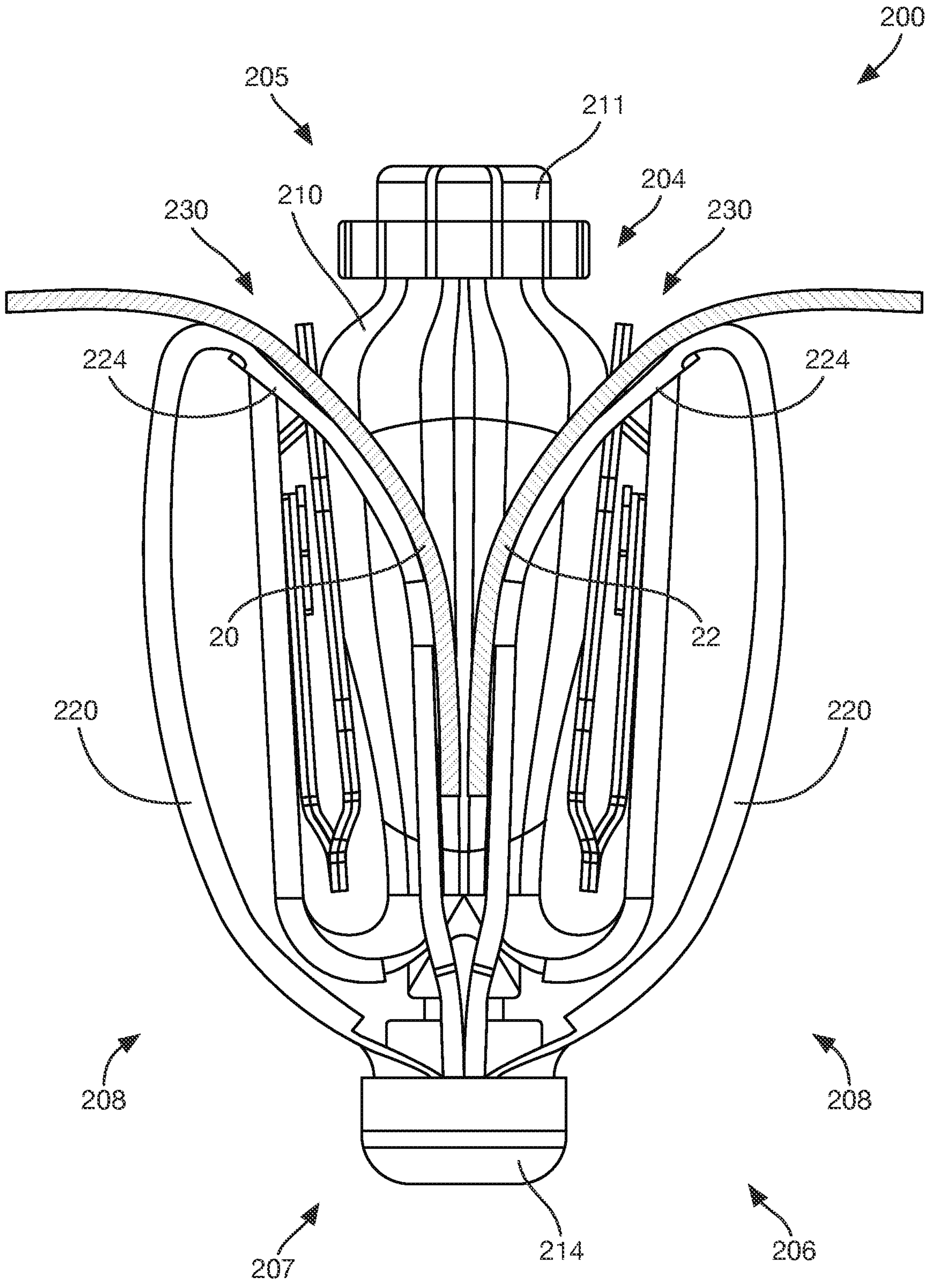
FIG. 50 is a schematic view illustrating a path of native valve leaflets along each side of a coaptation element or spacer of an example valve repair device or implant.

FIG. 50 illustrates the geometry of the coaptation element 210 and the paddle frame 224 from an LVOT perspective. As can be seen in this view, the coaptation element 210 has a tapered shape being smaller in dimension in the area closer to where the inside surfaces of the leaflets 20, 22 are required to coapt and increase in dimension as the coaptation element 210 extends toward the atrium. Thus, the depicted native valve geometry is accommodated by a tapered coaptation element geometry. Still referring to FIG. 50, the tapered coaptation element geometry, in conjunction with the illustrated expanding paddle frame 224 shape (toward the valve annulus) can help to achieve coaptation on the lower end of the leaflets, reduce stress, and minimize transvalvular gradients.

Figure 24:
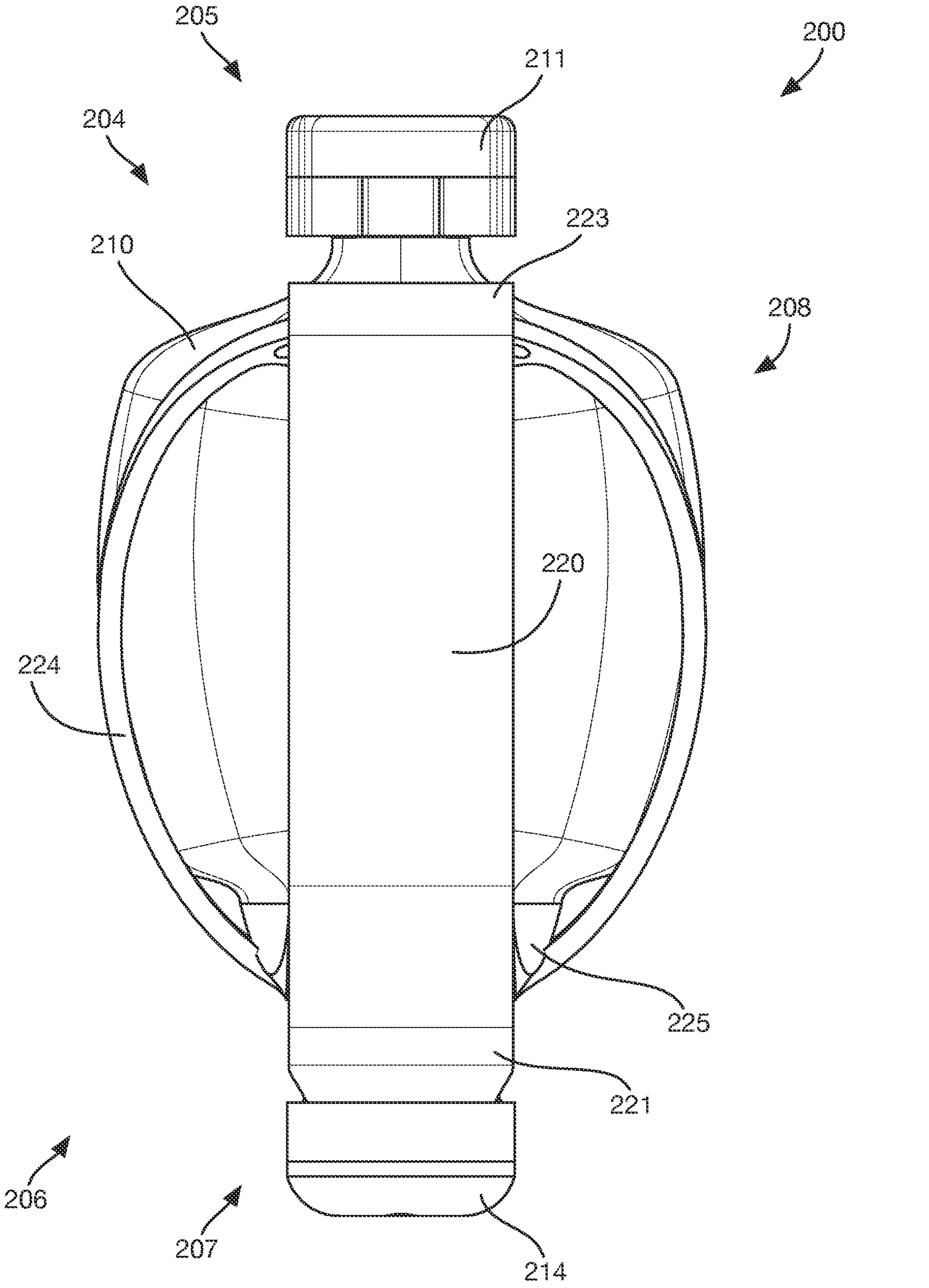
FIG. 24 shows a side view of the implantable device or implant of FIG. 22.
Figure 54:
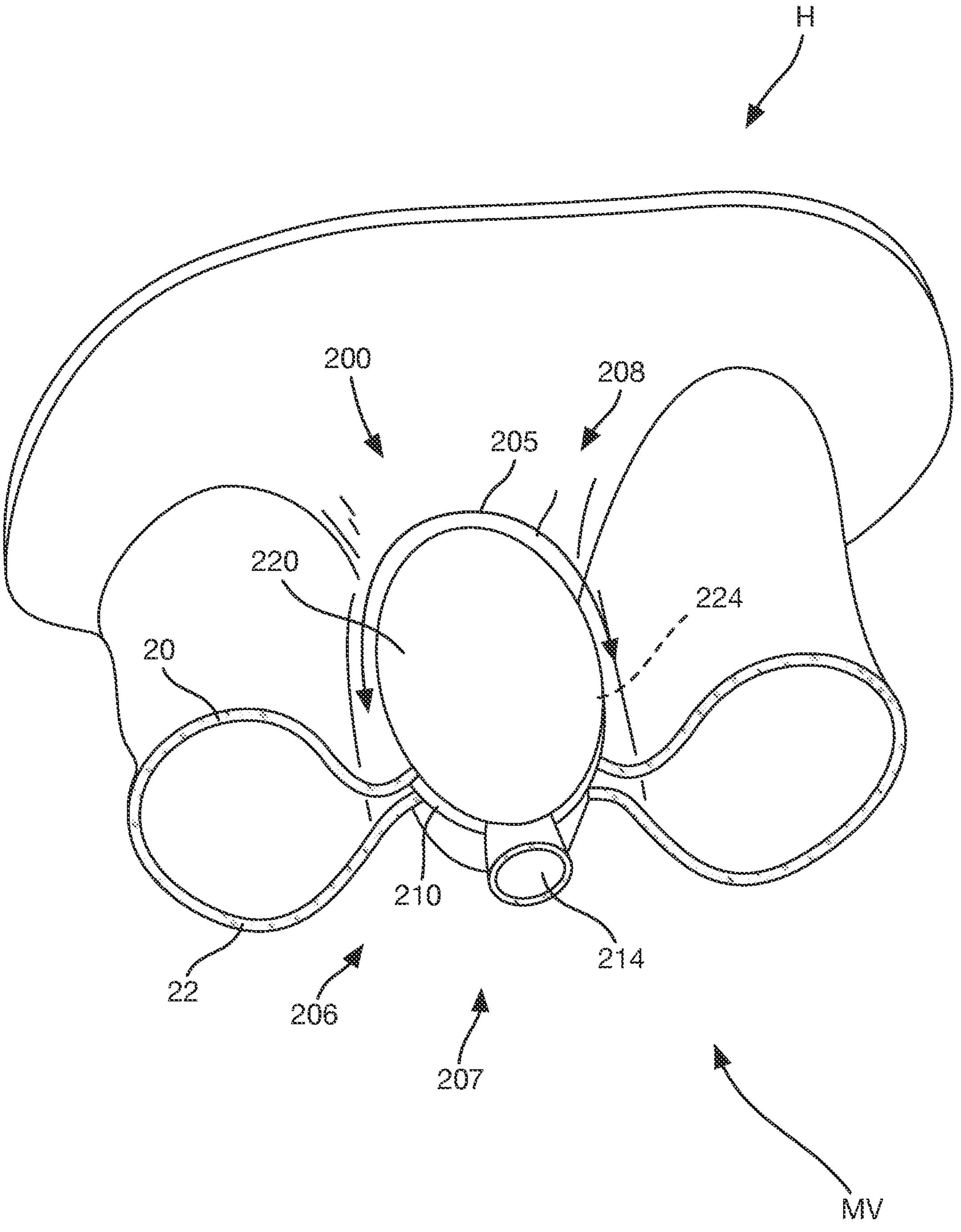
FIG. 54 is a perspective view of a valve repair device or implant attached to native valve leaflets with the coaptation element or spacer in the gap of the native valve shown from a ventricular side of the native valve.

Referring to FIG. 54, the shape of the coaptation element 210 and the paddle frames 224 can be defined based on an Intra-Commissural view of the native valve and the device 200. Two factors of these shapes are leaflet coaptation against the coaptation element 210 and reduction of stress on the leaflets due to the coaptation. Referring to FIGS. 54 and 24, to both coapt the valve leaflets 20, 22 against the coaptation element 210 and reduce the stress applied to the valve leaflets 20, 22 by the coaptation element 210 and/or the paddle frames 224, the coaptation element 210 can have a round or rounded shape and the paddle frames 224 can have a full radius that spans nearly the entirety of the paddle frame 224. The round shape of the coaptation element 210 and/or the illustrated fully rounded shape of the paddle frames 224 distributes the stresses on the leaflets 20, 22 across a large, curved engagement area 209. For example, in FIG. 54, the force on the leaflets 20, 22 by the paddle frames is spread along the entire rounded length of the paddle frame 224, as the leaflets 20 try to open during the diastole cycle.

Figure 55:
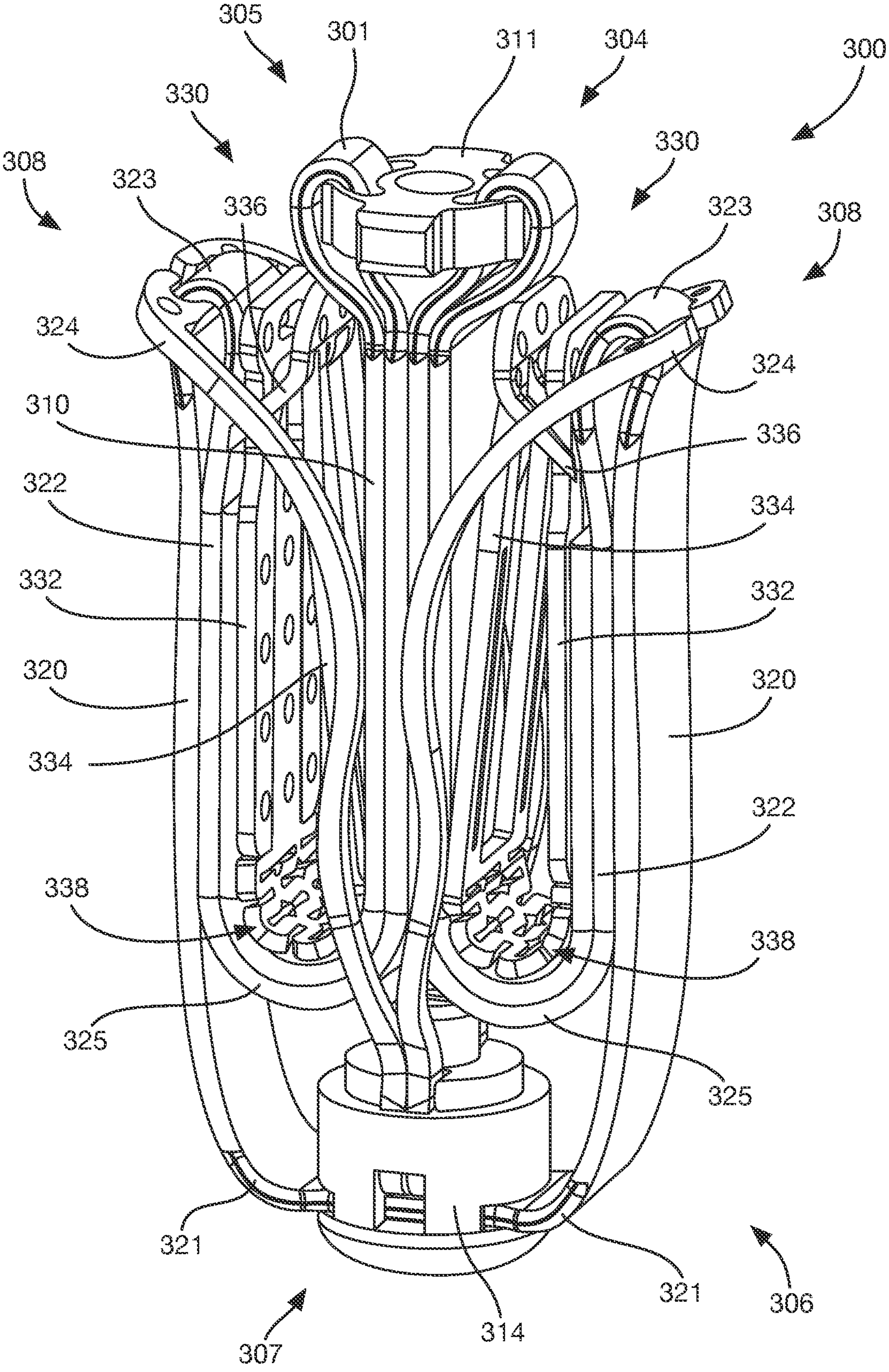
FIG. 55 shows a perspective view of an example implantable device or implant in a closed position.
Figure 56:
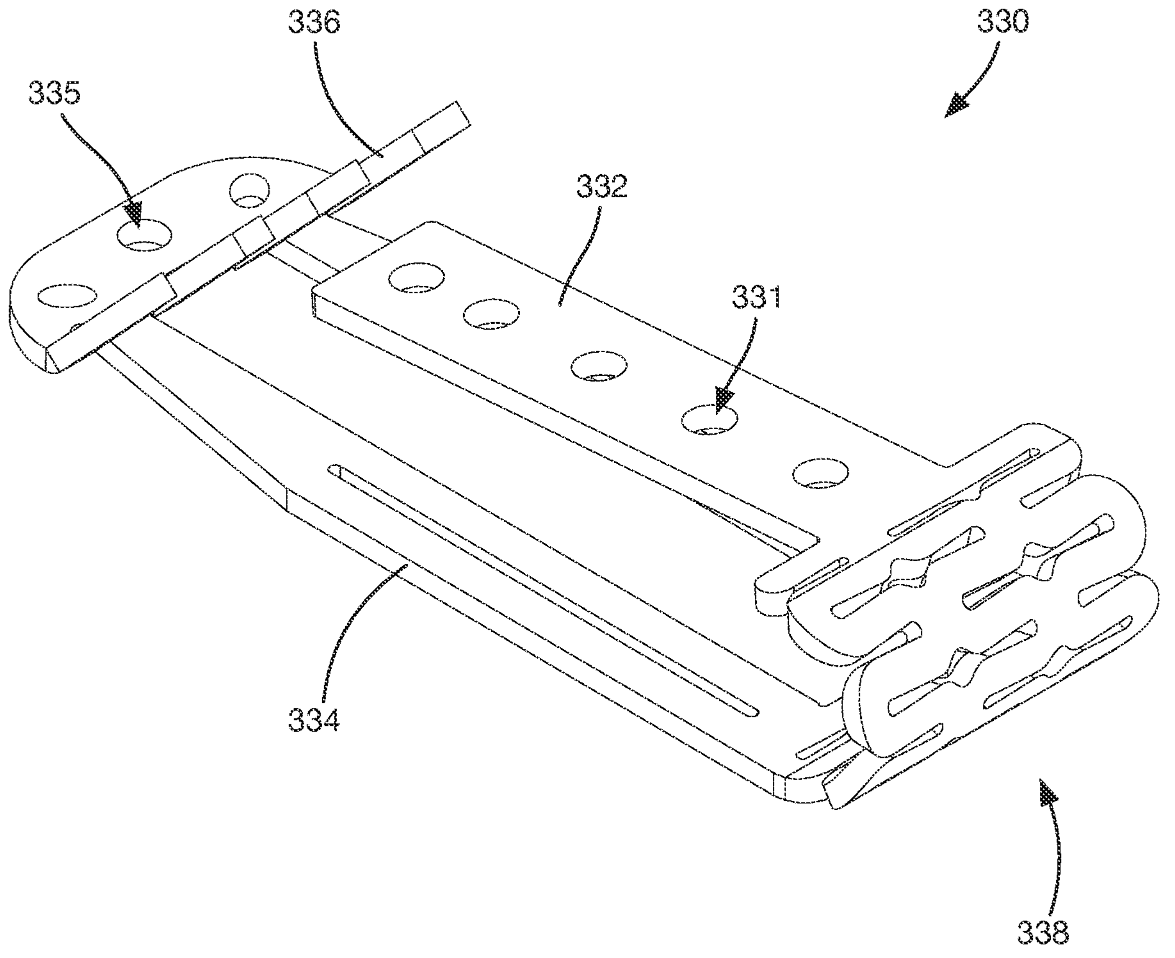
FIG. 56 shows a perspective view of an example clasp of an example implantable device or implant in a closed position.

Referring now to FIG. 55, an example of an implantable device or implant 300 is shown. The implantable device 300 is one of the many different configurations that the device 100 that is schematically illustrated in FIGS. 8-14 can take. The device 300 can include any other features for an implantable device or implant discussed in the present application, and the device 300 can be positioned to engage valve tissue 20, 22 as part of any suitable valve repair system (e.g., any valve repair system disclosed in the present application).

The implantable device or implant 300 includes a proximal or attachment portion 305, an anchor portion 306, and a distal portion 307. In some implementations, the device/implant 300 includes a coaptation portion 304, and the coaptation portion 304 can optionally include a coaptation element 310 (e.g., spacer, plug, membrane, sheet, etc.) for implantation between the leaflets 20, 22 of the native valve. In some implementations, the anchor portion 306 includes a plurality of anchors 308. In some implementations, each anchor 308 can include one or more paddles, e.g., outer paddles 320, inner paddles 322, paddle extension members or paddle frames 324. The anchors can also include and/or be coupled to clasps 330. In some implementations, the attachment portion 305 includes a first or proximal collar 311 (or other attachment element) for engaging with a capture mechanism (e.g., a capture mechanism such as the capture mechanism 213 shown in FIGS. 43-49) of a delivery system (e.g., a delivery system such as the system shown in FIGS. 38-42 and 49).

The anchors 308 can be attached to the other portions of the device and/or to each other in a variety of different ways (e.g., directly, indirectly, welding, sutures, adhesive, links, latches, integrally formed, a combination of some or all of these, etc.). In some implementations, the anchors 308 are attached to a coaptation member or coaptation element 310 by connection portions 325 and to a cap 314 by connection portions 321.

The anchors 308 can comprise first portions or outer paddles 320 and second portions or inner paddles 322 separated by connection portions 323. The connection portions 323 can be attached to paddle frames 324 that are hingeably attached to a cap 314 or other attachment portion. In this manner, the anchors 308 are configured similar to legs in that the inner paddles 322 are like upper portions of the legs, the outer paddles 320 are like lower portions of the legs, and the connection portions 323 are like knee portions of the legs.

In implementations with a coaptation member or coaptation element 310, the coaptation member or coaptation element 310 and the anchors 308 can be coupled together in various ways. For example, as shown in the illustrated example, the coaptation element 310 and the anchors 308 can be coupled together by integrally forming the coaptation element 310 and the anchors 308 as a single, unitary component. This can be accomplished, for example, by forming the coaptation element 310 and the anchors 308 from a continuous strip 301 of a braided or woven material, such as braided or woven nitinol wire. In the illustrated example, the coaptation element 310, the outer paddle portions 320, the inner paddle portions 322, and the connection portions 321, 323, 325 are formed from the continuous strip of fabric 301.

Like the anchors 208 of the implantable device or implant 200 described above, the anchors 308 can be configured to move between various configurations by axially moving the distal end of the device (e.g., cap 314, etc.) relative to the proximal end of the device (e.g., proximal collar 311 or other attachment element, etc.) and thus the anchors 308 move relative to a midpoint of the device. This movement can be along a longitudinal axis extending between the distal end (e.g., cap 314, etc.) and the proximal end (e.g., collar 311 or other attachment element, etc.) of the device. For example, the anchors 308 can be positioned in a fully extended or straight configuration (e.g., similar to the configuration of device 200 shown in FIG. 36) by moving the distal end (e.g., cap 314, etc.) away from the proximal end of the device.

In some implementations, in the straight configuration, the paddle portions 320, 322 are aligned or straight in the direction of the longitudinal axis of the device. In some implementations, the connection portions 323 of the anchors 308 are adjacent the longitudinal axis of the coaptation element 310 (e.g., similar to the configuration of device 200 shown in FIG. 36). From the straight configuration, the anchors 308 can be moved to a fully folded configuration (e.g., FIG. 55), e.g., by moving the proximal end and distal end toward each other and/or toward a midpoint or center of the device. Initially, as the distal end (e.g., cap 314, etc.) moves toward the proximal end and/or midpoint or center of the device, the anchors 308 bend at connection portions 321, 323, 325, and the connection portions 323 move radially outwardly relative to the longitudinal axis of the device 300 and axially toward the midpoint and/or toward the proximal end of the device (e.g., similar to the configuration of device 200 shown in FIG. 34). As the cap 314 continues to move toward the midpoint and/or toward the proximal end of the device, the connection portions 323 move radially inwardly relative to the longitudinal axis of the device 300 and axially toward the proximal end of the device (e.g., similar to the configuration of device 200 shown in FIG. 30).

In some implementations, the clasps comprise a moveable arm coupled to an anchor. In some implementations, the clasps 330 include a base or fixed arm 332, a moveable arm 334, optional barbs/friction-enhancing elements 336, and a joint portion 338. The fixed arms 332 are attached to the inner paddles 322, with the joint portion 338 disposed proximate the coaptation element 310. The joint portion 338 is spring-loaded so that the fixed and moveable arms 332, 334 are biased toward each other when the clasp 330 is in a closed condition.

The fixed arms 332 are attached to the inner paddles 322 through holes or slots 331 with sutures (not shown). The fixed arms 332 can be attached to the inner paddles 322 with any suitable means, such as screws or other fasteners, crimped sleeves, mechanical latches or snaps, welding, adhesive, or the like. The fixed arms 332 remain substantially stationary relative to the inner paddles 322 when the moveable arms 334 are opened to open the clasps 330 and expose the barbs 336. The clasps 330 are opened by applying tension to actuation lines (e.g., the actuation lines 216 shown in FIGS. 43-48) attached to holes 335 in the moveable arms 334, thereby causing the moveable arms 334 to articulate, pivot, and/or flex on the joint portions 338.

In short, the implantable device or implant 300 is similar in configuration and operation to the implantable device or implant 200 described above, except that the coaptation element 310, outer paddles 320, inner paddles 322, and connection portions 321, 323, 325 are formed from the single strip of material 301. In some implementations, the strip of material 301 is attached to the proximal collar 311, cap 314, and paddle frames 324 by being woven or inserted through openings in the proximal collar 311, cap 314, and paddle frames 324 that are configured to receive the continuous strip of material 301. The continuous strip 301 can be a single layer of material or can include two or more layers. In some implementations, portions of the device 300 have a single layer of the strip of material 301 and other portions are formed from multiple overlapping or overlying layers of the strip of material 301.

For example, FIG. 55 shows a coaptation element 310 and inner paddles 322 formed from multiple overlapping layers of the strip of material 301. The single continuous strip of material 301 can start and end in various locations of the device 300. The ends of the strip of material 301 can be in the same location or different locations of the device 300. For example, in the illustrated example of FIG. 55, the strip of material 301 begins and ends in the location of the inner paddles 322.

As with the implantable device or implant 200 described above, the size of the coaptation element 310 can be selected to minimize the number of implants that a single patient will require (preferably one), while at the same time maintaining low transvalvular gradients. In particular, forming many components of the device 300 from the strip of material 301 allows the device 300 to be made smaller than the device 200. For example, in some implementations, the anterior-posterior distance at the top of the coaptation element 310 is less than 2 mm, and the medial-lateral distance of the device 300 (i.e., the width of the paddle frames 324 which are wider than the coaptation element 310) at its widest is about 5 mm.

After implantation of an implantable device or implant, such as the devices/implants disclosed herein, to the native heart valve, forces may be applied to the leaflets via the connection with the implantable device or implant that causes tensile forces on the leaflets, and/or tensile forces may be applied to the implantable device or implant via its connection with the leaflets. For example, referring to FIG. 57, an implantable device or implant 400 can be connected to leaflets 20, 22 of the mitral valve MV to close a gap 26 between the leaflets 20, 22 and prevent regurgitation of blood through the mitral valve during the systolic phase of heart contraction. This connection between the device 400 and the leaflets 20, 22 causes a tension force F that pulls the leaflets 20, 22 away from the annulus 24 of the mitral valve MV. This connection between the device 400 and the leaflets 20, 22 can also cause a tension force T on the device 400.

The implantable device or implant 400 can take any suitable form that is capable of connecting to the leaflets 20, 22 of the mitral valve MV and preventing regurgitation of blood through the mitral valve MV, such as, for example, any form described in the present application or any form described in PCT patent application publication Nos. WO2018/195215, WO2020/076898, and WO 2019/139904, which are incorporated herein by reference in their entirety.

Figure 57:
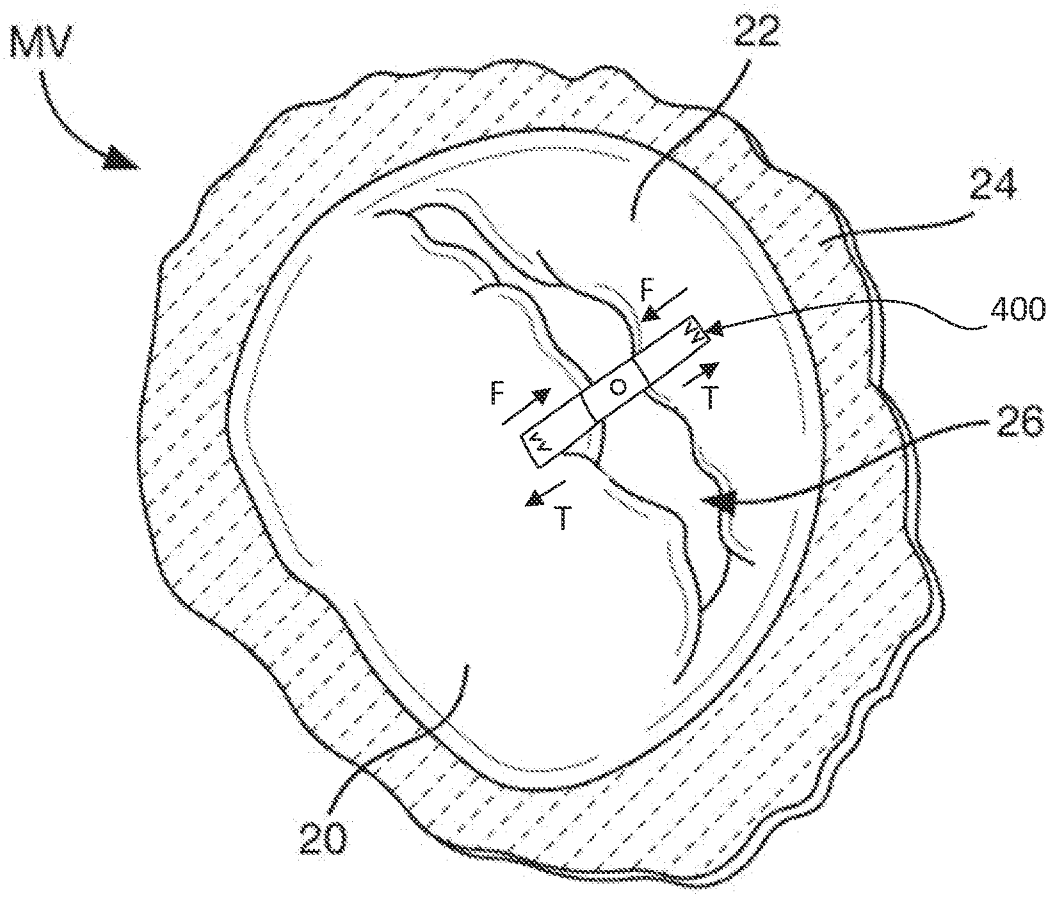
FIG. 57 shows an example implantable device or implant attached to leaflets of a dysfunctional mitral valve as viewed from an atrial side of the mitral valve, where implantable device or implant is causing a tension force to the leaflets.
Figure 59:
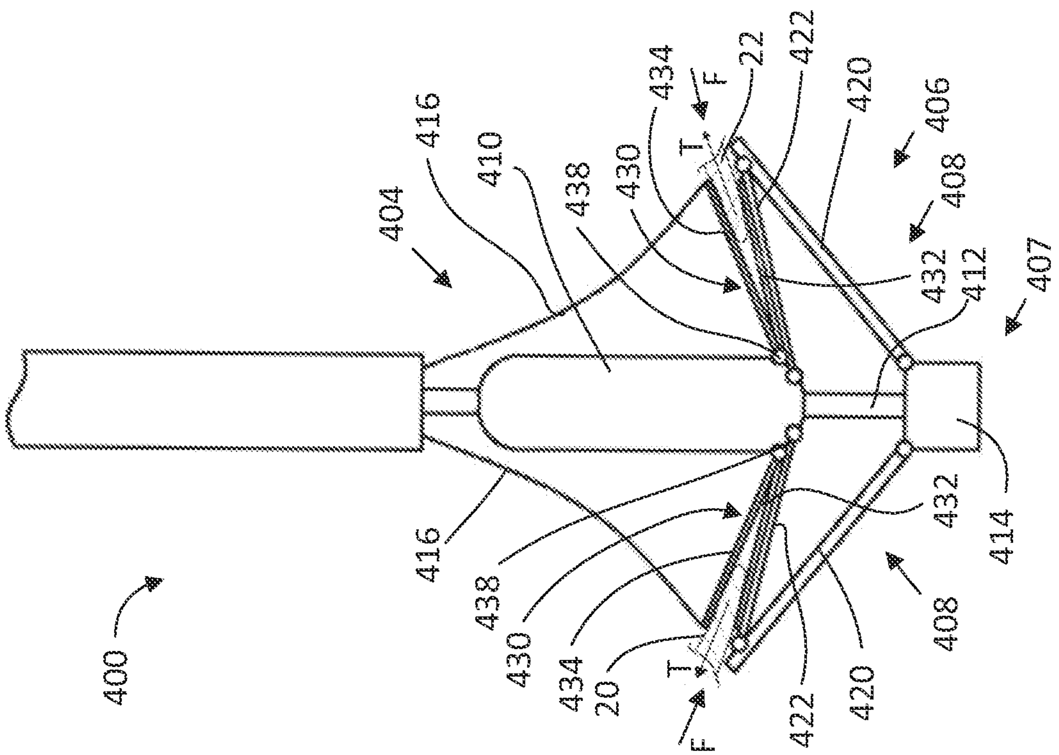
FIG. 59 shows the implantable device or implant of FIG. 58 attached to leaflets of a native valve and providing a tension force to the leaflets.
Figure 58:
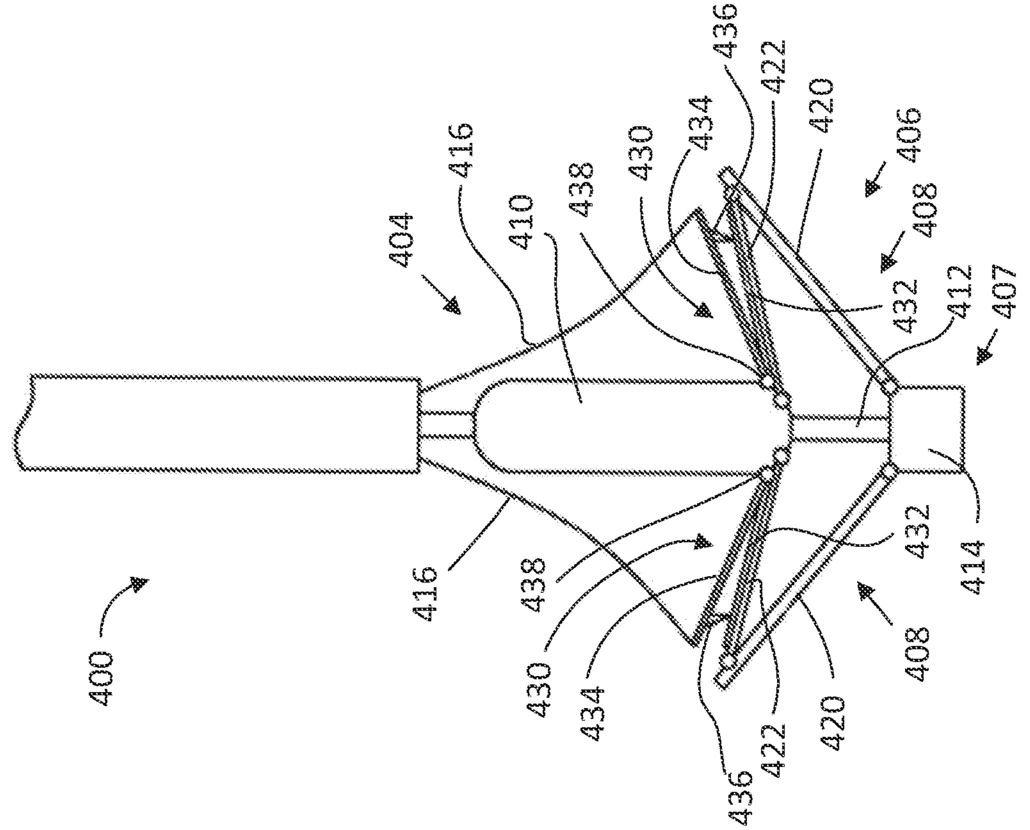
FIG. 58 shows an example of an implantable device or implant that can be used to cause the tension force to the leaflets as shown in FIG. 57.

In some implementations, referring to FIGS. 58 and 59, the device 400 can include an optional spacer, coaption, or coaptation portion 404, a proximal or attachment portion (e.g., attachment portion 205 shown in FIGS. 22-37), an anchor portion 406, and a distal portion 407. In some implementations, the optional spacer, coaption, or coaptation portion 404 is not included (See, e.g., FIG. 57). In some implementations, the optional coaptation portion 404 of the device optionally includes a coaptation element 410 (e.g., a spacer, coaption element, plug, etc.) for implantation between leaflets of a native valve. The optional coaptation element 410 can take any suitable form, such as, for example, any form described in the present application.

In some implementations, the anchor portion 406 includes a plurality of anchors 408. The anchors 408 can be configured in a variety of ways, such as, for example, any way described in the present application. In some implementations, each anchor 408 includes outer paddles 420, inner paddles 422, paddle extension members or paddle frames (e.g., paddle frame 224 shown in FIGS. 22-37), and clasps 430. The clasps 430 can have a base or fixed arm 432, a moveable arm 434, and barbs 436. The fixed arms 432 can be attached to the inner paddles 422, with the joint portion 438 disposed proximate the coaptation element 410. The fixed arms 432 and the movable arms 434 can be biased toward each other when the clasp 430 is in a closed condition. In some implementations, the clasps 430 include friction-enhancing elements or means for securing, such as barbs 436, protrusions, ridges, grooves, textured surfaces, adhesive, etc. In some implementations, the clasps 430 are opened by applying tension to actuation lines 416 attached to the moveable arms 434, thereby causing the moveable arms 434 to articulate, flex, or pivot on the joint portions 438. The actuation line 416 can take a wide variety of forms, such as, for example, any form described in the present application. The paddles 420, 422 and clasps 430 can take any suitable form, such as, for example, any form described in the present application.

The attachment portion can include a first or proximal collar (e.g., proximal collar 211 shown in FIGS. 22-37) for engaging with a capture mechanism (e.g., capture mechanism 213 shown in FIGS. 43-49) of a delivery system. The attachment portion can take any suitable form, such as, for example, any form described in the present application. In some implementations, an actuation element 412 (e.g., actuation shaft, actuation rod, actuation tube, actuation wire, actuation line, etc.) extends from an implant catheter (e.g., implant catheter 202 shown in FIG. 43) to engage and enable actuation of the implantable device or implant 400. For example, the actuation element 412 can extend through the capture mechanism, proximal collar, and coaptation element 410 to engage a cap 414 of the distal portion 407. The actuation element 412 can be configured to removably engage the cap 414 with a threaded connection, or the like, so that the actuation element 412 can move the device 400 between the open and closed position, and so that the actuation element can be disengaged and removed from the device 400 after implantation. The actuation element 412 and the cap 414 can take any suitable form, such as, for example, any form described in the present application.

Referring to FIG. 59, the implantable device or implant 400 is shown attached to leaflets 20, 22 of the native valve (see e.g., FIG. 57). The connection between the device 400 and the leaflets 20, 22, causes a tension force F on the leaflets and also causes a tension force T on the device 400.

Figure 60:
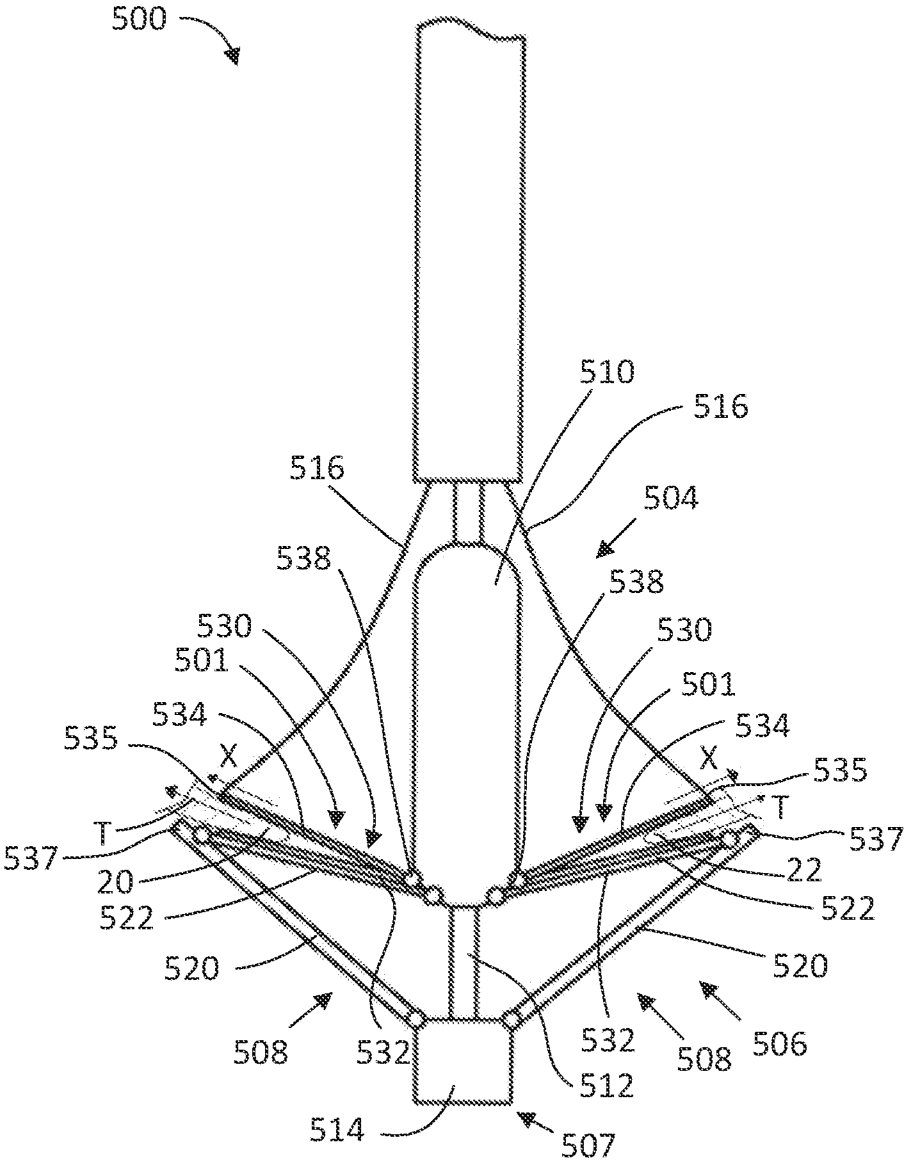
FIG. 60 shows an example of an implantable device or implant that includes an indication feature for allowing a user to determine if a tension force applied to the implantable device or implant has reached or exceeded a pre-set or predetermined tension, where the indication feature is movable between an allowable tension position and an exceeded tension position.

FIG. 60 shows an example of an implantable device or implant 500 that includes an indication feature 501 that allows a user to determine if a tension force applied to the implantable device or implant has reached or exceeded a predetermined tension (e.g., a predetermined allowable tension, a pre-set tension, etc.) or an optimal tension range. That is, the indication feature 501 provides a visual indication to a user when the user is viewing the connection between the device 500 and the leaflets 20, 22 through direct, echocardiographic, or fluoroscopic imaging. The predetermined tension can be set to a maximum allowable tension on the leaflets 20, 22. If the indication feature 501 is indicating to the user that the tension force applied to the device 500 has reached or exceeded the predetermined tension or optimal tension range, the user can open the device 500 to remove it from the leaflets 20, 22 and reconnect the device to a position in which the indication feature 501 has not reached or exceeded the predetermined tension or optimal tension range.

The device 500 can include the features of any suitable implantable device or implant, such as, for example, the features of the device 400 shown in FIGS. 58 and 59, or any other device described in the present application. For example, the device 500 can include a coaptation portion 504, a proximal or attachment portion (e.g., attachment portion 205 shown in FIGS. 22-37), an anchor portion 506, and a distal portion 507. In some implementations, the coaptation portion 504 of the device optionally includes a coaptation element 510 (e.g., a spacer, coaptation element, plug, membrane, sheet, etc.) for implantation between leaflets of a native valve. In some implementations, the anchor portion 506 includes a plurality of anchors 508. The anchors 508 can be configured in a variety of ways, such as, for example, any way described in the present application. In some implementations, each anchor 508 includes outer paddles 520, inner paddles 522, paddle extension members or paddle frames (e.g., paddle frame 224 shown in FIGS. 22-37), and clasps 530. The clasps 530 can have a base or fixed arm 532 and a moveable arm 534. The fixed arms 532 can be attached to the inner paddles 522, with the joint portion 538 disposed proximate the coaptation element 510. In some implementations, the clasps 530 include friction-enhancing elements or means for securing, such as barbs, protrusions, ridges, grooves, textured surfaces, adhesive, etc. In some implementations, the clasps 530 are opened by applying tension to actuation lines 516 attached to the moveable arms 534, thereby causing the moveable arms 534 to articulate, flex, or pivot on the joint portions 538. The actuation line 516 can take a wide variety of forms, such as, for example, any form described in the present application. The paddles 520, 522 and clasps 530 can take any suitable form, such as, for example, any form described in the present application.

In some implementations, an actuation element 512 (e.g., actuation shaft, actuation rod, actuation tube, actuation wire, actuation line, etc.) extends from an implant catheter (e.g., implant catheter 202 shown in FIG. 43) to engage and enable actuation of the implantable device or implant 500. For example, the actuation element 512 can extend through and move relative to the capture mechanism, proximal collar, and coaptation element 510 to engage a cap 514 of the distal portion 507. The actuation element 512 can be configured to removably engage the cap 514 with a threaded connection, or the like, so that the actuation element 512 can move the device 500 between the open and closed position, and so that the actuation element can be disengaged and removed from the device 500 after implantation. The actuation element 512 and the cap 514 can take any suitable form, such as, for example, any form described in the present application.

In the example illustrated by FIG. 60, the clasps 530 include the indication feature 501 that allows a user to determine if a tension force applied to the implantable device or implant 500 has reached or exceeded a predetermined tension (e.g., a predetermined allowable tension, a pre-set tension, etc.) or an optimal tension range. For example, at least a portion of the clasps 530 can be made of a flexible or elastic material(s) that allow at least a portion of the clasps 530 to stretch or extend in the direction X when a tension force T is applied to the device 500 via its connection with the leaflets 20, 22. In some implementations, if one or more of the clasps 530 extend in the direction X to or above a predetermined length, the indication feature 501 is in an exceeded tension position where the tension force applied to the device 500 has reached or exceeded the predetermined tension or optimal tension range. If the clasps 530 do not extend to or above the predetermined length, the indication feature 501 is in an allowable tension position where the tension force applied to the device 500 is below the predetermined tension or within the optimal tension range.

The user can, for example, determine the amount of extension of the clasps 530 by comparing the outer ends of the clasps 530 relative to other components of the device 500 (e.g., the paddles 520, 522, the coaptation element 510, etc.), or the imaging software can be configured to measure the length of the clasps 530 to determine if the clasps extended to or above the predetermined length. In some implementations, pulling of an outer end 535 of the moveable arm 534 of the clasp 530 past the outer end 537 of the paddles 520, 522 indicates that the tension force applied to the clasp has reached or exceeded a predetermined allowable tension force or pre-set tension force. In some implementations, the indication feature 501 can include a visual marking (e.g., a dot, an X-mark, a radiopaque marker, etc.) that allows a user to more easily determine an extension of the clasps 530 relative to other components of the device 500, such as the paddles 520, 522.

Figure 61:
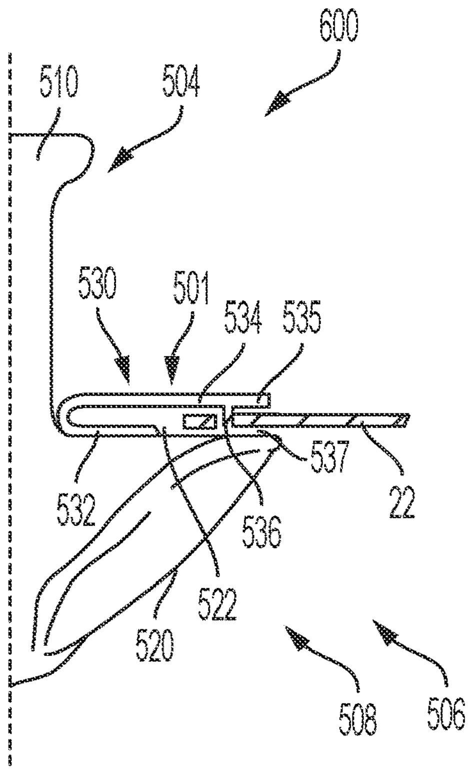
FIG. 61 shows a partial view of an example of an implantable device or implant that includes an indication feature for allowing a user to determine if a tension applied to the implantable device or implant has exceeded a pre-set or predetermined tension, where the indication feature is included on one or more clasps of the implantable device or implant and is shown in an allowable tension position.
Figure 62:
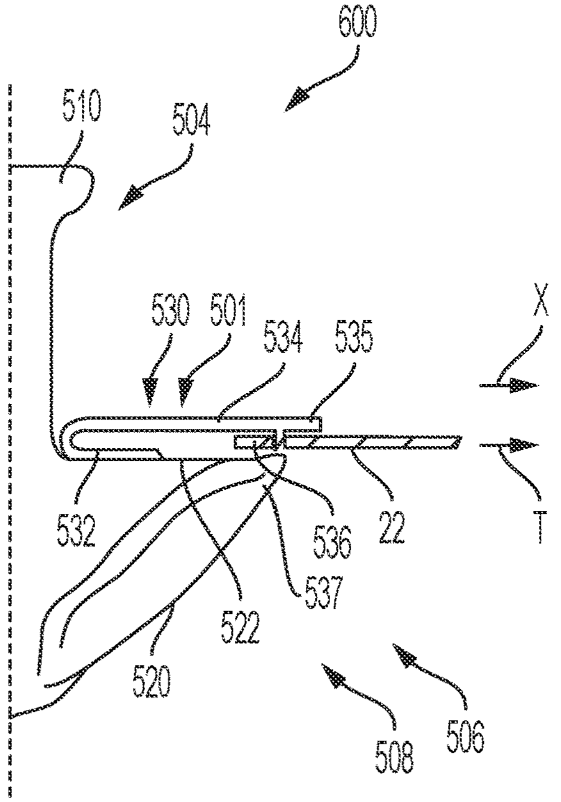
FIG. 62 shows a partial view of the implantable device or implant of FIG. 61 where the indication feature is shown in the exceeded tension position.

FIGS. 61 and 62 illustrate a device 600 that is a more specific example of the device 500 shown in FIG. 60. FIG. 61 illustrates the device 600 when the indication feature 501 is in an allowable tension position, and FIG. 62 illustrates the device 600 when the indication feature 501 is in an exceeded tension position. The device 600 includes an optional coaptation element 510, an inner paddle 520, an outer paddle 522, and a clasp 530. The fixed arm 532 of the clasp 530 is attached to the inner paddle 520, and the movable arm 534 of the clasp 530 includes a barb 536 (or other friction enhancing element or means) that secures the device 600 to the leaflet 22 of the native valve. In this example, at least the movable arm 534 of the clasp 530 is made of a flexible or elastic material such that the tension force T (FIG. 62) applied to the device 600 causes the movable arm 534 of the clasp 530 to move in the outward direction X. In some implementations, the indication feature 501 can include a visual marking (e.g., a dot, an X-mark, etc.) that allows a user to more easily determine an extension of the clasps 530 relative to other components of the device 500.

Referring to FIG. 61, the outer end 535 of the movable arm 534 of the clasp 530 does not extend beyond the outer end 537 of the outer paddle 520, which indicates allowable tension. Referring to FIG. 62, the outer end 535 of the movable arm 534 of the clasp 530 extends beyond the outer end 537 of the outer paddle 520, which indicates exceeded tension. The ability of the movable arm 534 to stretch is advantageous because the barb 536 of the clasp 530 that engages the leaflet 22 moves with the movable arm 534, and this stretching of the movable arm 534 reduces the stress applied to the leaflet 22 caused by the barb 536. While the indication feature 501 of the clasp 530 is shown with the devices 500, 600 shown in FIGS. 60 through 62, it should be understood that the clasp 530 can be used with any suitable implantable device or implant to provide an indication to a user if a tension applied to the implantable device or implant has reached or exceeded a predetermined tension or optimal tension range.

Figure 63:
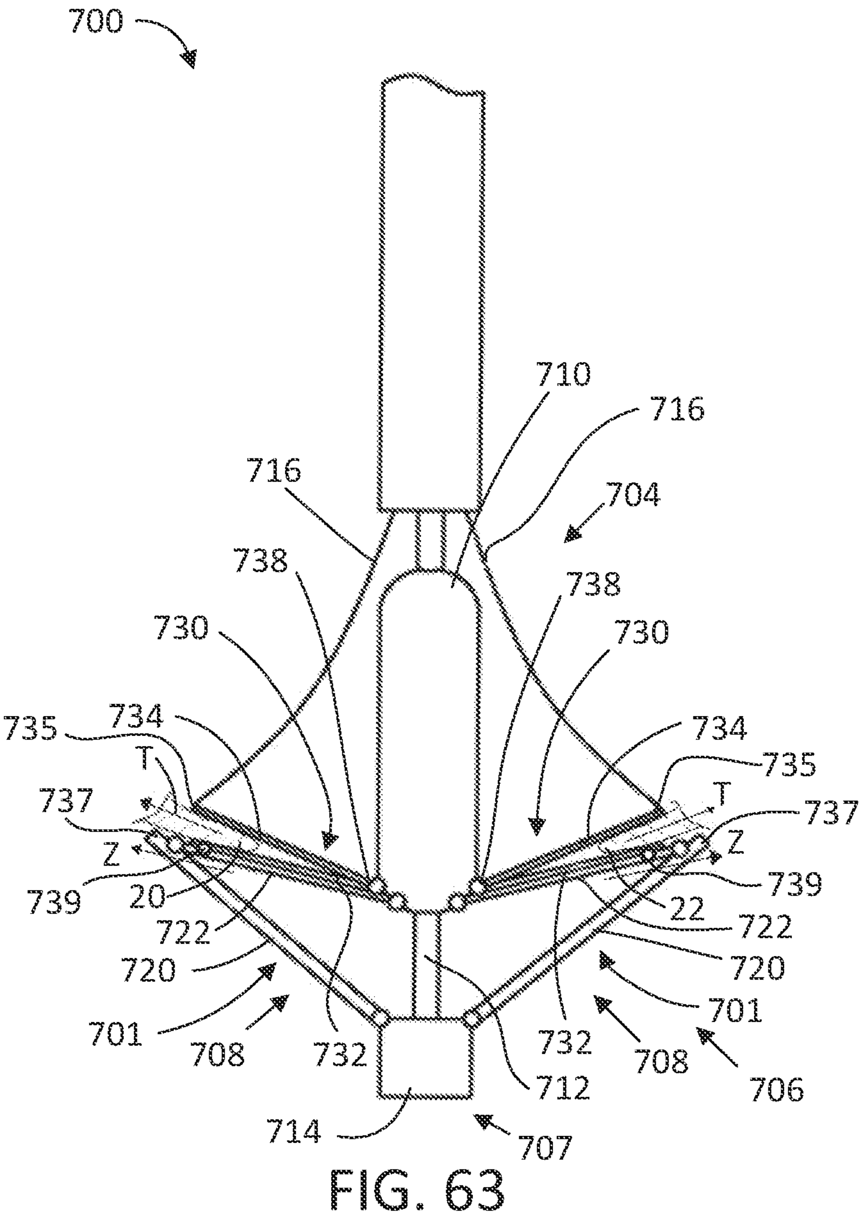
FIG. 63 shows an example of an implantable device or implant that includes an indication feature for allowing a user to determine if a tension applied to the implantable device or implant has reached or exceeded a pre-set or predetermined tension, where the indication feature is movable between an allowable tension position and an exceeded tension position.

FIG. 63 shows an example of an implantable device or implant 700 that includes an indication feature 701 that allows a user to determine if a tension force applied to the implantable device or implant has reached or exceeded a predetermined tension (e.g., a predetermined allowable tension, a pre-set tension, etc.) or an optimal tension range. In some implementations, pulling of the outer end 737 of the paddles 720, 722 more than a predetermined distance indicates that the tension force applied to the clasp has reached or exceeded a predetermined allowable tension force or pre-set tension force. For example, a marker 739 can be applied to the inner paddle. Movement of the marker 739 past the outer end 735 of the clasp 730 (or any other portion of the device) indicates that the tension force applied to the clasp has reached or exceeded the predetermined allowable tension force or pre-set tension force. That is, the indication feature 701 provides a visual indication to a user when the user is viewing the connection between the device 700 and the leaflets 20, 22 through direct, echocardiographic, or fluoroscopic imaging. If the indication feature 701 is indicating to the user that the tension force applied to the device 700 has reached or exceeded the predetermined tension or optimal tension range, the user can open the device 700 to remove it from the leaflets 20, 22 and reconnect the device to a position in which the indication feature 701 has not reached or exceeded the predetermined tension or optimal tension range.

The device 700 can include the features of any suitable implantable device or implant, such as, for example, the features of the device 400 shown in FIGS. 58 and 59, or any other device described in the present application. For example, the device 700 can include a coaptation portion 704, a proximal or attachment portion (e.g., attachment portion 205 shown in FIGS. 22-37), an anchor portion 706, and a distal portion 707. In some implementations, the coaptation portion 704 of the device optionally includes a coaptation element 710 (e.g., a spacer, coaptation element, plug, membrane, sheet, etc.) for implantation between leaflets of a native valve. In some implementations, the anchor portion 706 includes a plurality of anchors 708. The anchors 708 can be configured in a variety of ways, such as, for example, any way described in the present application. In some implementations, each anchor 708 includes outer paddles 720, inner paddles 722, paddle extension members or paddle frames (e.g., paddle frame 224 shown in FIGS. 22-37), and clasps 730. The clasps 730 can have a base or fixed arm 732 and a moveable arm 734. The fixed arms 732 can be attached to the inner paddles 722, with the joint portion 738 disposed proximate the coaptation element 710. In some implementations, the clasps 730 include friction-enhancing elements or means for securing, such as barbs, protrusions, ridges, grooves, textured surfaces, adhesive, etc. In some implementations, the clasps 730 are opened by applying tension to actuation lines 716 attached to the moveable arms 734, thereby causing the moveable arms 734 to articulate, flex, or pivot on the joint portions 738. The actuation line 516 can take a wide variety of forms, such as, for example, any form described in the present application. The paddles 720, 722 and clasps 730 can take any suitable form, such as, for example, any form described in the present application.

In some implementations, an actuation element 712 (e.g., actuation shaft, actuation rod, actuation tube, actuation wire, actuation line, etc.) extends from an implant catheter (e.g., implant catheter 202 shown in FIG. 43) to engage and enable actuation of the implantable device or implant 700. For example, the actuation element 712 can extend through and move relative to the capture mechanism, proximal collar, and coaptation element 710 to engage a cap 714 of the distal portion 707. The actuation element 712 can be configured to removably engage the cap 714 with a threaded connection, or the like, so that the actuation element 712 can move the device 700 between the open and closed position, and so that the actuation element can be disengaged and removed from the device 700 after implantation. The actuation element 712 and the cap 714 can take any suitable form, such as, for example, any form described in the present application.

In the example illustrated by FIG. 63, one or both of the paddles 720, 722 include the indication feature 701 that allows a user to determine if a tension force applied to the implantable device or implant 700 has reached or exceeded a predetermined tension (e.g., a predetermined allowable tension, a pre-set tension, etc.) or an optimal tension range. For example, at least a portion of the paddles 720, 722 can be made of a flexible or elastic material(s) that allow at least a portion of the paddles 720, 722 to stretch or extend in the direction Z when a tension force T is applied to the device 700 via its connection with the leaflets 20, 22. In some implementations, if one or more of the paddles 720, 722 extend in the direction Z to or above a predetermined length, the indication feature 701 is in an exceeded tension position where the tension force applied to the device 700 has reached or exceeded the predetermined tension or optimal tension range. If the paddles 720, 722 do not extend to or above the predetermined length, the indication feature 701 is in an allowable tension position where the tension force applied to the device 700 is below the predetermined tension or within the optimal tension range. The user can, for example, determine the amount of extension of the paddles 720, 722 by comparing the outer ends of the paddles 720, 722 relative to other components of the device 700 (e.g., the clasps 730, the coaptation element 710, etc.), or the imaging software can be configured to measure the length of the paddles 720, 722 to determine if the paddles extended to or above the predetermined length. In some implementations, the indication feature 701 can include a visual marking 739 (e.g., a dot, an X-mark, a radiopaque marker, etc.) that allows a user to more easily determine an extension of the paddles 720, 722 relative to other components of the device 700.

Figure 64:
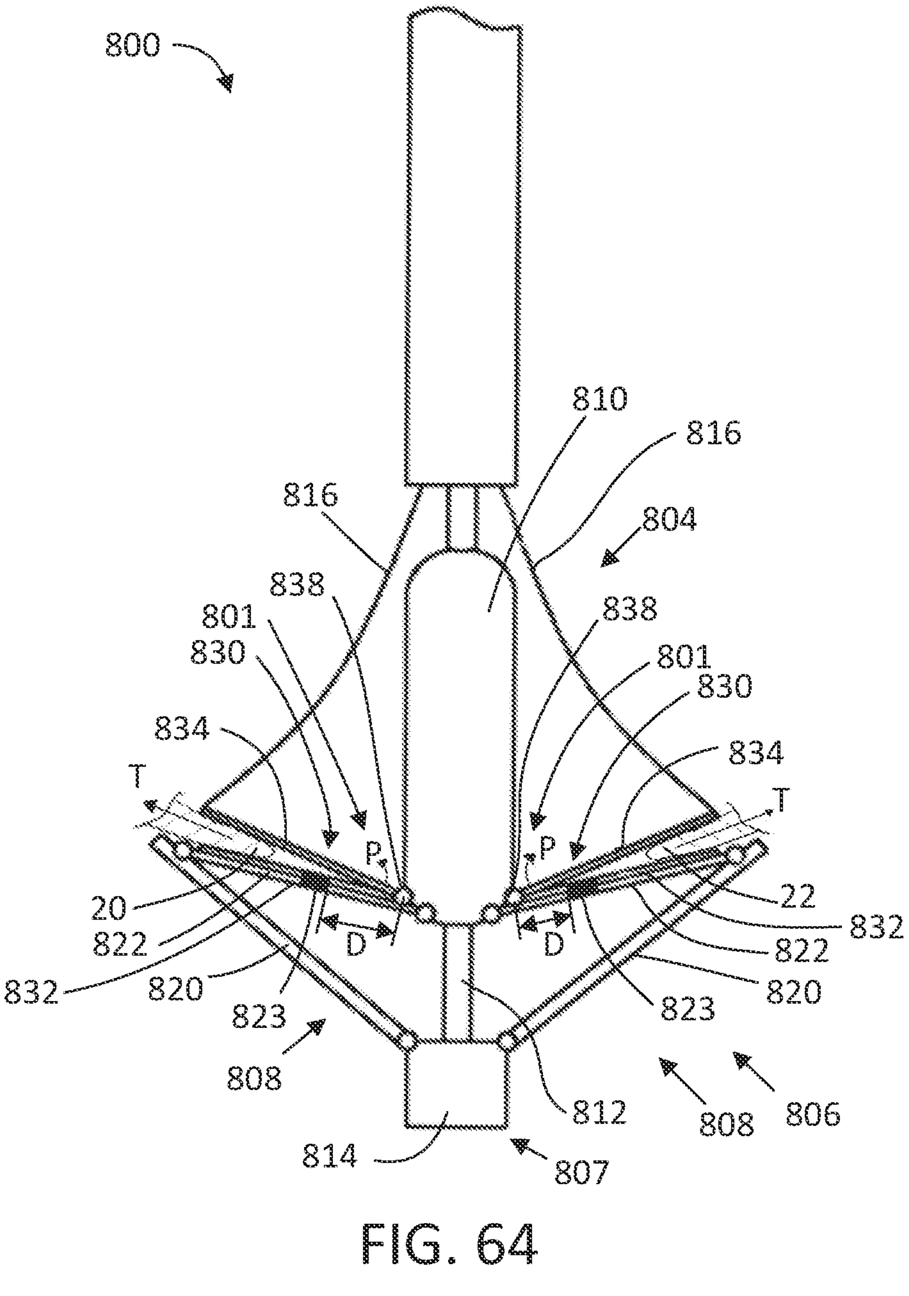
FIG. 64 shows an example of an implantable device or implant that includes an indication feature for allowing a user to determine if a tension applied to the implantable device or implant has reached or exceeded a pre-set or predetermined tension, where the indication feature is movable between an allowable tension position and an exceeded tension position.

FIG. 64 shows an example of an implantable device or implant 800 that includes an indication feature 801 that allows a user to determine if a tension force applied to the implantable device or implant has reached or exceeded a predetermined tension (e.g., a predetermined allowable tension, a pre-set tension, etc.) or an optimal tension range. In some implementations, pulling P of a clasp hinge portion 838 away from the inner paddle 822 more than a predetermined distance indicates that the tension force applied to the clasp has reached or exceeded a predetermined allowable tension force or pre-set tension force. For example, flexing of the fixed arm 832 of the clasp 830 enough to form a visible gap between the clasp hinge portion 838 and the inner paddle 822 can be an indicator that the tension force applied to the clasp has reached or exceeded the predetermined allowable tension force or pre-set tension force. The indication feature 801 provides a visual indication to a user when the user is viewing the connection between the device 800 and the leaflets 20, 22 through direct, echocardiographic, or fluoroscopic imaging. If the indication feature 801 is indicating to the user that the tension force applied to the device 800 has reached or exceeded the predetermined tension or optimal tension range, the user can open the device 800 to remove it from the leaflets 20, 22 and reconnect the device to a position in which the indication feature 801 has not reached or exceeded the predetermined tension or optimal tension range.

The device 800 can include the features of any suitable implantable device or implant, such as, for example, the features of the device 400 shown in FIGS. 58 and 59, or any other device described in the present application. For example, the device 800 can include a coaptation portion 804, a proximal or attachment portion (e.g., attachment portion 205 shown in FIGS. 22-37), an anchor portion 806, and a distal portion 807. In some implementations, the coaptation portion 804 of the device optionally includes a coaptation element 810 (e.g., a spacer, coaptation element, plug, etc.) for implantation between leaflets of a native valve. In some implementations, the anchor portion 806 includes a plurality of anchors 808. The anchors 808 can be configured in a variety of ways, such as, for example, any way described in the present application. In some implementations, each anchor 808 includes outer paddles 820, inner paddles 822, paddle extension members or paddle frames (e.g., paddle frame 224 shown in FIGS. 22-37), and clasps 830. The clasps 830 can have a base or fixed arm 832 and a moveable arm 834 that are connected at joint 838. The fixed arms 832 can be attached to the inner paddles 822 by a connection element 823 (e.g., a connection band, a fastener, an adhesive, etc.). In the illustrated example, the fixed arm 832 is connected to the inner paddle 822 such that a distance D exists between the connection element 823 and the joint 838. The distance D can be between ⅛ and ¾ of the length of the fixed arm 832, such as ¼ and ⅝ of the length of the fixed arm, such as ⅜ and ½ of the length of the fixed arm 832.

In some implementations, the clasps 830 include friction-enhancing elements or means for securing, such as barbs, protrusions, ridges, grooves, textured surfaces, adhesive, etc. In some implementations, the clasps 830 are opened by applying tension to actuation lines 816 attached to the moveable arms 834, thereby causing the moveable arms 834 to articulate, flex, or pivot on the joint portions 838. The actuation line 816 can take a wide variety of forms, such as, for example, any form described in the present application. The paddles 820, 822 and clasps 830 can take any suitable form, such as, for example, any form described in the present application.

In some implementations, an actuation element 812 (e.g., actuation shaft, actuation rod, actuation tube, actuation wire, actuation line, etc.) extends from an implant catheter (e.g., implant catheter 202 shown in FIG. 43) to engage and enable actuation of the implantable device or implant 800. For example, the actuation element 812 can extend through and move relative to the capture mechanism, proximal collar, and coaptation element 810 to engage a cap 814 of the distal portion 807. The actuation element 812 can be configured to removably engage the cap 814 with a threaded connection, or the like, so that the actuation element 812 can move the device 800 between the open and closed position, and so that the actuation element can be disengaged and removed from the device 800 after implantation. The actuation element 812 and the cap 814 can take any suitable form, such as, for example, any form described in the present application.

In the illustrated example, the clasps 830 include the indication feature 801 that allows a user to determine if a tension force applied to the implantable device or implant 800 has reached or exceeded a predetermined tension (e.g., a predetermined allowable tension, a pre-set tension, etc.) or an optimal tension range. For example, at least a portion of the clasps 830 can be made of a flexible or elastic material(s) that allow clasps 830 to bend or flex upward in the direction P when a tension force T is applied to the device 800 via its connection with the leaflets 20, 22. That is, the distance D between the connection element 823 and the pivot point 838 allows the pivot join 838 to be free to move relative to the paddles 820, 822, and the tension force T applied to the device 800 can cause the movable arm to move in the direction X, which causes the joint 838 to flex in the upward direction P. In some implementations, if one or more of the clasps 830 flex in the direction P to or above a predetermined amount, such as any amount that is visible via imaging, the indication feature 801 is in an exceeded tension position where the tension force applied to the device 800 has reached or exceeded the predetermined tension or optimal tension range. If the clasps 830 do not flex to or above the predetermined amount, the indication feature 801 is in an allowable tension position where the tension force applied to the device 800 is below the predetermined tension or within the optimal tension range. The user can, for example, determine the amount the clasps 838 flex by comparing the joint 838 of the clasps 830 relative to other components of the device 800 (e.g., the paddles 820, 822, the coaptation element 810, etc.), or the imaging software can be configured to measure the amount of flex of the clasps 830 to determine if the indication feature 801 is in the exceeded tension position. In some implementations, the indication feature 801 can include a visual marking (e.g., a dot, an X-mark, etc.) that allows a user to more easily determine flexing or pivoting of the clasps 830 relative to other components of the device 800.

Figure 65:
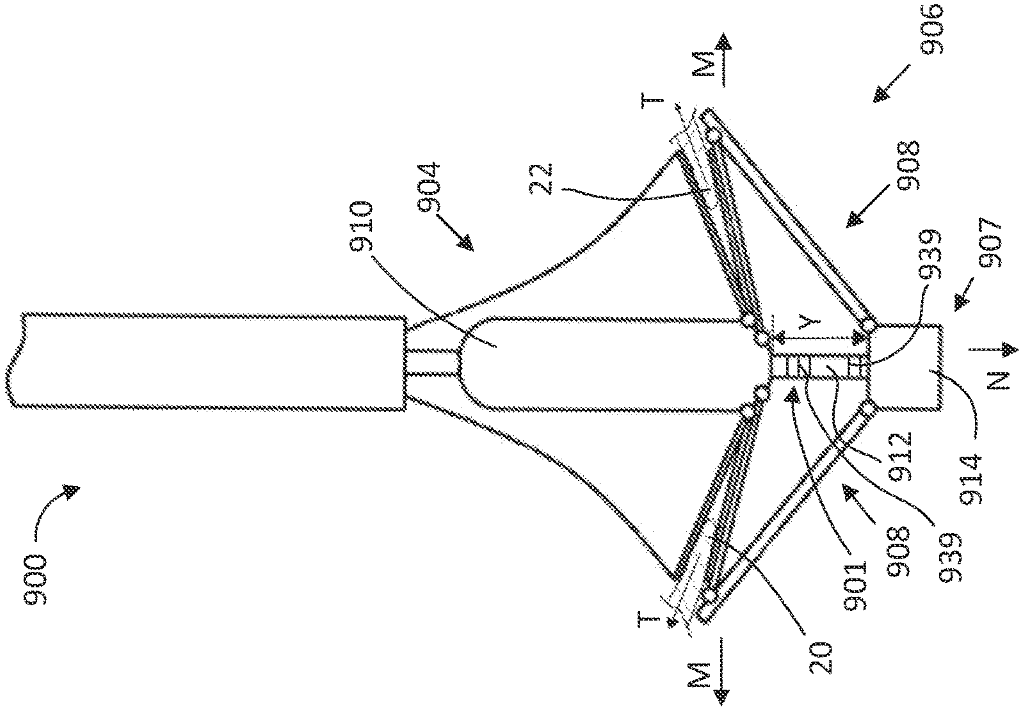
FIG. 65 shows an example of an implantable device or implant that includes an indication feature for allowing a user to determine if a tension applied to the implantable device or implant has reached or exceeded a pre-set or predetermined tension, where the indication feature is movable between an allowable tension position and an exceeded tension position.

FIG. 65 shows an example of an implantable device or implant 900 that includes an indication feature 901 that allows a user to determine if a tension force applied to the implantable device or implant has reached or exceeded a predetermined tension (e.g., a predetermined allowable tension, a pre-set tension, etc.) or an optimal tension range. In some implementations, pushing or pulling of the actuation element 912 of the device more than a predetermined distance indicates that the tension force applied to the clasp has reached or exceeded a predetermined allowable tension force or pre-set tension force. For example, one or more markers 939 can be applied to the actuation element and the absence, presence, and/or number of visible markers indicates that the tension force applied to the clasp has reached or exceeded the predetermined allowable tension force or pre-set tension force. That is, the indication feature 901 provides a visual indication to a user when the user is viewing the connection between the device 900 and the leaflets 20, 22 through direct, echocardiographic, or fluoroscopic imaging. If the indication feature 901 is indicating to the user that the tension force applied to the device 900 has reached or exceeded the predetermined tension or optimal tension range, the user can open the device 900 to remove it from the leaflets 20, 22 and reconnect the device to a position in which the indication feature 901 has not reached or exceeded the predetermined tension or optimal tension range.

The device 900 can include the features of any suitable implantable device or implant, such as, for example, the features of the device 400 shown in FIGS. 58 and 59, or any other device described in the present application. For example, the device 900 can include a coaptation portion 904, a proximal or attachment portion (e.g., attachment portion 205 shown in FIGS. 22-37), an anchor portion 906, and a distal portion 907. In some implementations, the coaptation portion 904 of the device optionally includes a coaptation element 910 (e.g., a spacer, coaptation element, plug, etc.) for implantation between leaflets of a native valve. In some implementations, the anchor portion 906 includes a plurality of anchors 908. The anchors 908 can be configured in a variety of ways, such as, for example, any way described in the present application.

In some implementations, an actuation element 912 (e.g., actuation shaft, actuation rod, actuation tube, actuation wire, actuation line, etc.) extends from an implant catheter (e.g., implant catheter 202 shown in FIG. 43) to engage and enable actuation of the implantable device or implant 900. For example, the actuation element 912 can extend through and move relative to the capture mechanism, proximal collar, and coaptation element 910 to engage a cap 914 of the distal portion 907. The actuation element 912 can be configured to removably engage the cap 914 with a threaded connection, or the like, so that the actuation element 912 can move the device 900 between the open and closed position, and so that the actuation element can be disengaged and removed from the device 900 after implantation. The actuation element 912 and the cap 914 can take any suitable form, such as, for example, any form described in the present application.

In the illustrated example, the actuation element 912 includes the indication feature 901 that allows a user to determine if a tension force applied to the implantable device or implant 900 has reached or exceeded a predetermined tension (e.g., a predetermined allowable tension, a pre-set tension, etc.) or an optimal tension range. For example, when the device 900 is in the closed position and connected to the leaflets 20, 22 (as shown in FIG. 65), a length Y of the actuation element 912 is visible by the user between the coaptation element 910 and the cap 914. When the tension force T is applied to the device 900 by its connection with the leaflets 20, 22, the anchor portion 908 may move to an open position in the outward direction M, which causes the cap 914 and actuation element 912 to move in the downward direction N relative to the coaptation element 910. This movement of the actuation element 912 relative to the coaptation element 910 causes the visible length Y of the actuation element 912 to increase. In some implementations, if the visible length Y of the actuation element 912 increases by a predetermined amount, the indication feature 901 is in an exceeded tension position where the tension force applied to the device 900 has reached or exceeded the predetermined tension or optimal tension range. If the visible length Y of the actuation element 912 does not increase by the predetermined amount, the indication feature 901 is in an allowable tension position where the tension force applied to the device 900 is below the predetermined tension or within the optimal tension range. The user can, for example, determine the amount the visible length Y of the actuation element increases by comparing the position of the coaptation element 910 relative to other components of the device 900 (e.g., the cap 914, the anchor portion 908, etc.), or the imaging software can be configured to measure the visible length Y of the actuation element 912 to determine if the indication feature 901 is in the exceeded tension position. In some implementations, the indication feature 901 can include one or more visual markings (e.g., a dot, an X-mark, a radiopaque marker, etc.) that allows a user to more easily determine if the visible length Y of the actuation element 912 has increased to or above a predetermined length. For example, if the visual marking is visible to the user, then the visible length Y has increased to or above a predetermined length.

Figure 66:
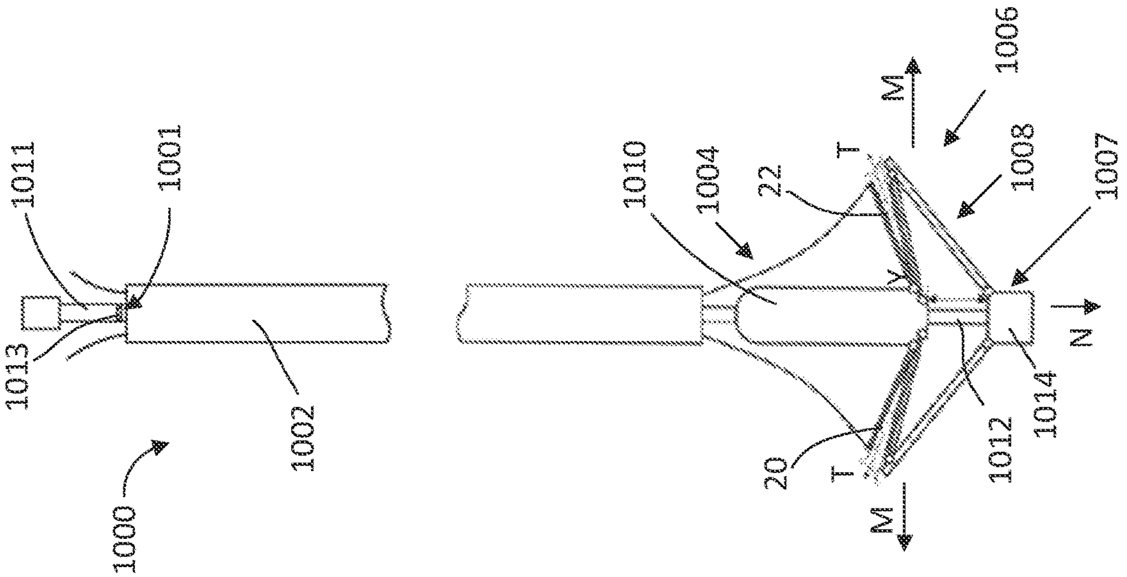
FIG. 66 shows an example of an implantable device or implant that includes an indication feature for allowing a user to determine if a tension applied to the implantable device or implant has reached or exceeded a pre-set or predetermined tension, where the indication feature is movable between an allowable tension position and an exceeded tension position.

FIG. 66 shows an example of an implantable device or implant 100 that includes an indication feature 1001 that allows a user to determine if a tension force applied to the implantable device or implant has reached or exceeded a predetermined tension (e.g., a predetermined allowable tension, a pre-set tension, etc.) or an optimal tension range. In some implementations, pushing or pulling of the actuation element 1012 of the device more than a predetermined distance indicates that the tension force applied to the clasp has reached or exceeded a predetermined allowable tension force or pre-set tension force. For example, one or more markers 1013 can be applied to the actuation element and the absence, presence, and/or number of visible markers indicates that the tension force applied to the clasp has reached or exceeded a predetermined allowable tension force or pre-set tension force. That is, the indication feature 1001 provides a visual indication to a user when the user is viewing the connection between the device 1000 and the leaflets 20, 22 through direct, echocardiographic, or fluoroscopic imaging. If the indication feature 1001 is indicating to the user that the tension force applied to the device 1000 has reached or exceeded the predetermined tension or optimal tension range, the user can open the device 1000 to remove it from the leaflets 20, 22 and reconnect the device to a position in which the indication feature 1001 has not reached or exceeded the predetermined tension or optimal tension range.

The device 1000 can include the features of any suitable implantable device or implant, such as, for example, the features of the device 400 shown in FIGS. 58 and 59, or any other device described in the present application. For example, the device 1000 can include a coaptation portion 1004, a proximal or attachment portion (e.g., attachment portion 205 shown in FIGS. 22-37), an anchor portion 1006, and a distal portion 1007. In some implementations, the coaptation portion 1004 of the device optionally includes a coaptation element 1010 (e.g., a spacer, coaptation element, plug, etc.) for implantation between leaflets of a native valve. In some implementations, the anchor portion 1006 includes a plurality of anchors 1008. The anchors 1008 can be configured in a variety of ways, such as, for example, any way described in the present application.

In some implementations, an actuation element 1012 (e.g., actuation shaft, actuation rod, actuation tube, actuation wire, actuation line, etc.) extends from an implant catheter (e.g., implant catheter 202 shown in FIG. 43) to engage and enable actuation of the implantable device or implant 1000. A proximal portion 1011 of the actuation element 1012 is controlled by the user such that the user can cause the actuation element 1012 to engage and actuate the device 1000. For example, the actuation element 1012 can extend through and move relative to the capture mechanism, proximal collar, and coaptation element 1010 to engage a cap 1014 of the distal portion 1007. The actuation element 1012 can be configured to removably engage the cap 1014 with a threaded connection, or the like, so that the actuation element 1012 can move the device 1000 between the open and closed position, and so that the actuation element 1012 can be disengaged and removed from the device 1000 after implantation. The actuation element 1012 and the cap 1014 can take any suitable form, such as, for example, any form described in the present application.

In the illustrated example, the proximal portion 1011 of the actuation element 1012 includes the indication feature 1001 that allows a user to determine if a tension force applied to the implantable device or implant 1000 has reached or exceeded a predetermined tension (e.g., a predetermined allowable tension, a pre-set tension, etc.) or an optimal tension range. For example, when the device 1000 is in the closed position and connected to the leaflets 20, 22 (as shown in FIG. 66), a visual marking 1013 of the indication feature 1001 is visible on the proximal portion 1011 of the actuation feature 112. When the tension force T is applied to the device 1000 by its connection with the leaflets 20, 22, the anchor portion 1008 may move to an open position in the outward direction M, which causes the cap 1014 and actuation element 1012 to move in the downward direction N relative to the delivery device 1002, such as a catheter or catheter handle. This movement of the actuation element 1012 relative to the delivery device 1002 causes the visual marking 1013 of the actuation element 912 to move into the delivery device 1002 such that the visual marking 1013 is no longer visible by the user. In some implementations, if the visual marking 1013 is no longer visible by the user after the device 1000 is connected to the leaflets 20, 22 and the clasps are in the closed position (and the device is in the open or closed position), the indication feature 1001 is in an exceeded tension position where the tension force applied to the device 1000 has reached or exceeded a predetermined tension or an optimal tension range. If the visual marking 1013 is visible by the user after the device 1000 attached to the leaflets 20, 22 and the clasps are in the closed position (and the device is in the open or closed position), the indication feature 1001 is in an allowable tension position where the tension force applied to the device 1000 is below the predetermined tension or optimal tension range.

Figure 67:
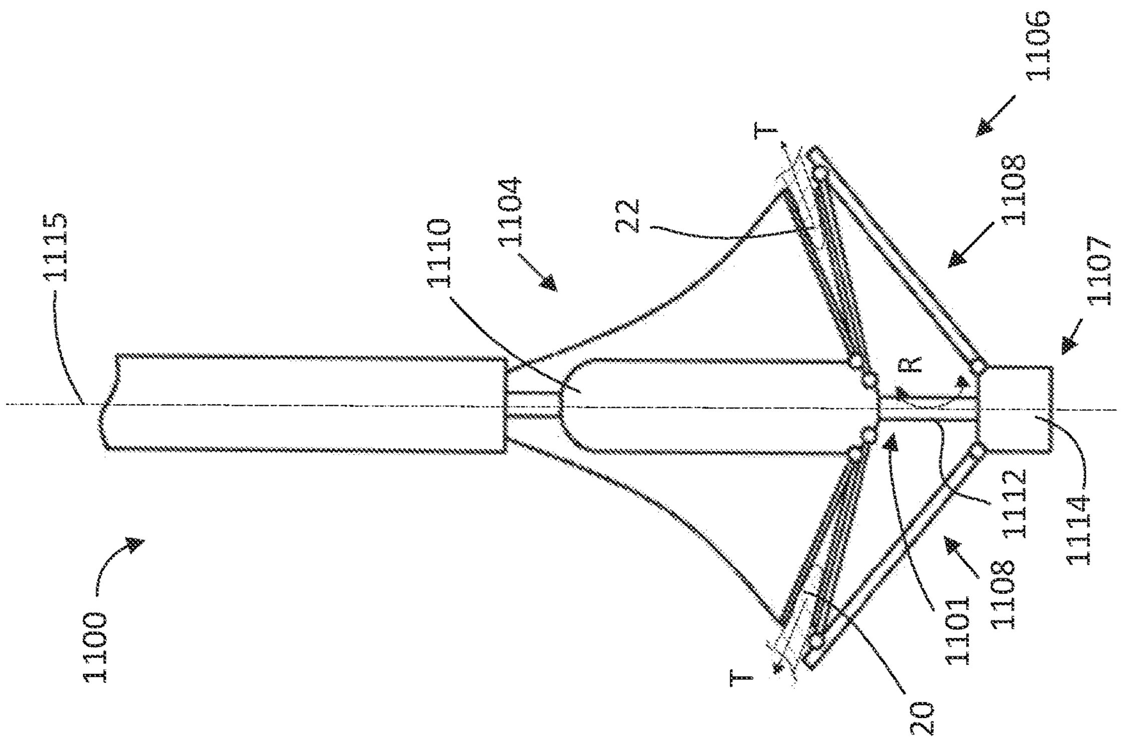
FIG. 67 shows an example of an implantable device or implant that includes an indication feature for allowing a user to determine if a tension applied to the implantable device or implant has reached or exceeded a pre-set or predetermined tension, where the indication feature is movable between an allowable tension position and an exceeded tension position.

FIG. 67 shows an example of an implantable device or implant 1100 that includes an indication feature 1101 that allows a user to determine if a tension force applied to the implantable device or implant has reached or exceeded a predetermined tension (e.g., a predetermined allowable tension, a pre-set tension, etc.) or an optimal tension range. In some implementations, bending or buckling of the actuation element 1112 of the device more than a predetermined amount indicates that the tension force applied to the clasp has reached or exceeded a predetermined allowable tension force or pre-set tension force. For example, a visualizable bend in the wire 1112 indicates that the tension force applied to the clasp has reached or exceeded a predetermined allowable tension force or pre-set tension force. That is, the indication feature 1101 provides a visual indication to a user when the user is viewing the connection between the device 1100 and the leaflets 20, 22 through direct, echocardiographic, or fluoroscopic imaging. If the indication feature 1101 is indicating to the user that the tension force applied to the device 1100 has reached or exceeded the predetermined tension or optimal tension range, the user can open the device 1100 to remove it from the leaflets 20, 22 and reconnect the device to a position in which the indication feature 1101 has not reached or exceeded the predetermined tension or optimal tension range.

The device 1100 can include the features of any suitable implantable device or implant, such as, for example, the features of the device 400 shown in FIGS. 58 and 59, or any other device described in the present application. For example, the device 1100 may include a coaptation portion 1104, a proximal or attachment portion (e.g., attachment portion 205 shown in FIGS. 22-37), an anchor portion 1106, and a distal portion 1107. In some implementations, the coaptation portion 1104 of the device optionally includes a coaptation element 1110 (e.g., a spacer, coaptation element, plug, etc.) for implantation between leaflets of a native valve. In some implementations, the anchor portion 1106 includes a plurality of anchors 1108. The anchors 1108 can be configured in a variety of ways, such as, for example, any way described in the present application.

In some implementations, an actuation element 1112 (e.g., actuation shaft, actuation rod, actuation tube, actuation wire, actuation line, etc.) extends from an implant catheter (e.g., implant catheter 202 shown in FIG. 43) to engage and enable actuation of the implantable device or implant 1100. For example, the actuation element 1112 can extend through and move relative to the capture mechanism, proximal collar, and coaptation element 1110 to engage a cap 1114 of the distal portion 1107. The actuation element 1112 can be configured to removably engage the cap 1114 with a threaded connection, or the like, so that the actuation element 912 can move the device 1100 between the open and closed position, and so that the actuation element can be disengaged and removed from the device 1100 after implantation. The actuation element 1112 and the cap 1114 can take any suitable form, such as, for example, any form described in the present application.

In the illustrated example, the actuation element 1112 includes the indication feature 1101 that allows a user to determine if a tension force applied to the implantable device or implant 1100 has reached or exceeded a predetermined tension (e.g., a predetermined allowable tension, a pre-set tension, etc.) or an optimal tension range. For example, the actuation element 1112 can be made of a flexible or elastic material(s) that allow at least a portion of the actuation element to bend or flex in the direction R when a tension force T is applied to the device 1100 by its connection with the leaflets 20, 22. That is, when the device 1100 is in the closed position and connected to the leaflets 20, 22 (as shown in FIG. 67), the actuation element 1112 is substantially aligned with a central axis 1115 of the device 1100. When the tension force T is applied to the device 1100 by its connection with the leaflets 20, 22, the tension force may be transferred to the cap 1114 or coaptation element 1110, which causes the flexible actuation element 1112 to bend or flex. In some implementations, if the actuation element 1112 bends or flexes relative to the central axis 1115 of the device 1100, the indication feature 1101 is in an exceeded tension position where the tension force applied to the device 1100 has reached or exceeded the predetermined tension or optimal tension range. If the actuation element 1112 is substantially aligned with the central axis 1115 when the device 1100 is connected to the leaflets 20, 22, the indication feature 1101 is in an allowable tension position where the tension force applied to the device 1100 is below the predetermined tension or optimal tension range. The user can, for example, determine if the actuation element 1112 bends or flexes by comparing the positioning of the actuation element 1112 relative to other components of the device 1100 (e.g., the cap 1114, the coaptation element 1110, the anchor portion(s) 1108, etc.), or the imaging software can be configured to determine if the actuation element 1112 is bending or flexing relative to the central axis 1115. In some implementations, the indication feature 1101 can include a visual marking (e.g., a dot, an X-mark, a radiopaque marker, etc.) that allows a user to more easily determine if the actuation element 1112 is bending or flexing.

Figure 68:
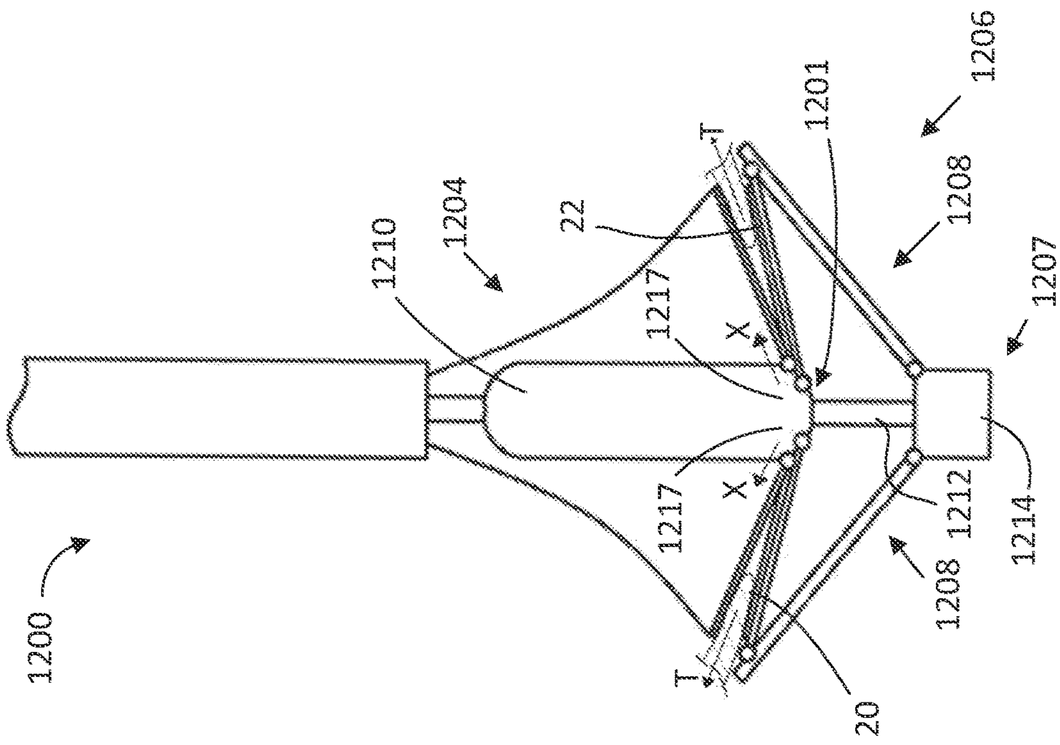
FIG. 68 shows an example of an implantable device or implant that includes an indication feature for allowing a user to determine if a tension applied to the implantable device or implant has reached or exceeded a pre-set or predetermined tension, where the indication feature is movable between an allowable tension position and an exceeded tension position.

FIG. 68 shows an example of an implantable device or implant 1200 that includes an indication feature 1201 that allows a user to determine if a tension force applied to the implantable device or implant has reached or exceeded a predetermined tension (e.g., a predetermined allowable tension, a pre-set tension, etc.) or an optimal tension range. In some implementations, outward pulling or bulging of a portion of the spacer 1210 more than a predetermined amount indicates that the tension force applied to the clasp has reached or exceeded a predetermined allowable tension force or pre-set tension force. For example, a visualizable outward pulling or bulging of a portion of the spacer 1210 indicates that the tension force applied to the clasp has reached or exceeded the predetermined allowable tension force or pre-set tension force. That is, the indication feature 1201 provides a visual indication to a user when the user is viewing the connection between the device 1200 and the leaflets 20, 22 through direct, echocardiographic, or fluoroscopic imaging. If the indication feature 1201 is indicating to the user that the tension force applied to the device 1200 has reached or exceeded the predetermined tension or optimal tension range, the user can open the device 1200 to remove it from the leaflets 20, 22 and reconnect the device to a position in which the indication feature 1201 has not reached or exceeded the predetermined tension or optimal tension range.

The device 1200 can include the features of any suitable implantable device or implant, such as, for example, the features of the device 400 shown in FIGS. 58 and 59, or any other device described in the present application. For example, the device 1200 can include a coaptation portion 1204, an actuation element 1212, a proximal or attachment portion (e.g., attachment portion 205 shown in FIGS. 22-37), an anchor portion 1206, and a distal portion 1207. In some implementations, the coaptation portion 1204 of the device optionally includes a coaptation element 1210 (e.g., a spacer, coaption element, plug, etc.) for implantation between leaflets of a native valve. In some implementations, the anchor portion 1206 includes a plurality of anchors 1208. The anchors 1208 can be configured in a variety of ways, such as, for example, any way described in the present application. The anchors 1208 can be attached to a distal portion of the coaptation element 1210.

In the illustrated example, the coaptation element 1210 includes the indication feature 1201 that allows a user to determine if a tension force applied to the implantable device or implant 1200 has reached or exceeded a predetermined tension (e.g., a predetermined allowable tension, a pre-set tension, etc.) or an optimal tension range. For example, at least a portion of the coaptation element 1210 includes one or more flexible portions 1217 that connect to the anchors 1208 (e.g., connect to at least one of the inner or outer paddles of the anchors 1208) such that the flexible portions 1217 can expand in an outward direction X when a tension force T is applied to the device 1200 via its connection with the leaflets 20, 22. In some implementations, if one or more of the flexible portions 1217 of the coaptation element 1210 are pulled or bulge in the direction X to or above a predetermined amount, the indication feature 1201 is in an exceeded tension position where the tension force applied to the device 1200 has reached or exceeded the predetermined tension or optimal tension range. If the flexible portions 1217 of the coaptation element 1210 are not pulled or bulge to or above the predetermined amount, the indication feature 1201 is in an allowable tension position where the tension force applied to the device 1200 is below the predetermined tension or within the optimal tension range. The user can, for example, determine the amount of pulling or bulging of the flexible portions 1217 of the coaptation element 1210 by comparing the flexible portions relative to other components of the device 1200 (e.g., the remainder of the coaptation element 1210, the cap 1214, etc.), or the imaging software can be configured to measure the pulling or bulging of the flexible portions 1217 of the coaptation element 1210 to determine if they extended to or beyond the predetermined length. In some implementations, the connection between the anchors 1208 and the flexible portions 1217 of the coaptation element 1210 cause the anchors 1208 to extend in the outward direction X, and the user can determine the amount of extension of the flexible portions 1217 by comparing the positioning of the anchors 1208 relative to other components of the device 1200 (e.g., the remainder of the coaptation element 1210, the cap 1214, etc.). In some implementations, the indication feature 1201 can include a visual marking (e.g., a dot, an X-mark, a radiopaque marker, etc.) that allows a user to more easily determine an extension of the flexible portions 1217 of the coaptation element 1210 relative to other components of the device 1200. For example, the visual marking can be located on the flexible portions 1217 of the coaptation element 1210 and, if the flexible portions 1217 to indicate that the indication feature 1201 is in the exceeded tension position, the visual marking will expand to a distorted shape.

Figure 69:
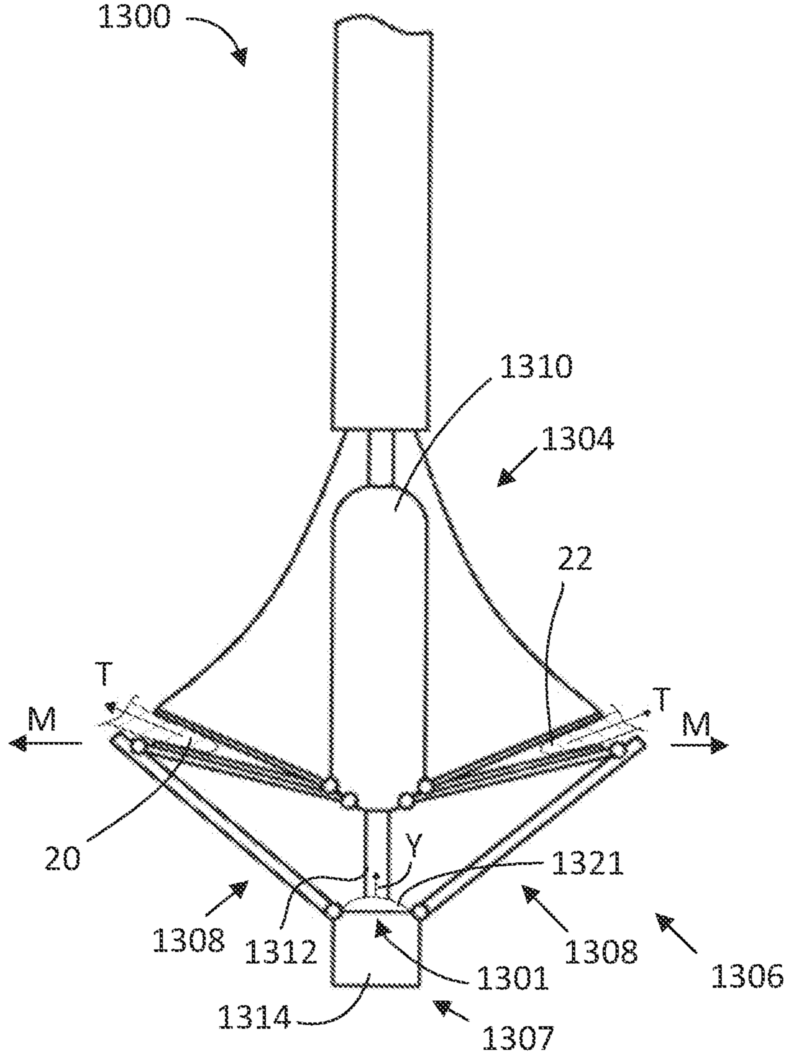
FIG. 69 shows an example of an implantable device or implant that includes an indication feature for allowing a user to determine if a tension applied to the implantable device or implant has reached or exceeded a pre-set or predetermined tension, where the indication feature is movable between an allowable tension position and an exceeded tension position.

FIG. 69 shows an example of an implantable device or implant 1300 that includes an indication feature 1301 that allows a user to determine if a tension force applied to the implantable device or implant has reached or exceeded a predetermined tension (e.g., a predetermined allowable tension, a pre-set tension, etc.) or an optimal tension range. In some implementations, a top of the cap is configured to move between a flat or depressed configuration and a popped-up or domed configuration when acted on by the actuation element 1112 and/or paddles when more than a pre-set or predetermined amount of tension force is applied to the clasp. For example, a visualizable dome shape indicates that the tension force applied to the clasp has reached or exceeded a predetermined allowable tension force or pre-set tension force. That is, the indication feature 1301 provides a visual indication to a user when the user is viewing the connection between the device 1300 and the leaflets 20, 22 through direct, echocardiographic, or fluoroscopic imaging. If the indication feature 1301 is indicating to the user that the tension force applied to the device 1300 has reached or exceeded the predetermined tension or optimal tension range, the user can open the device 1300 to remove it from the leaflets 20, 22 and reconnect the device to a position in which the indication feature 1301 has not reached or exceeded the predetermined tension or optimal tension range.

The device 1300 can include the features of any suitable implantable device or implant, such as, for example, the features of the device 400 shown in FIGS. 58 and 59, or any other device described in the present application. For example, the device 1300 may include a coaptation portion 1304, a proximal or attachment portion (e.g., attachment portion 205 shown in FIGS. 22-37), an anchor portion 1306, and a distal portion 1307. In some implementations, the coaptation portion 1304 of the device optionally includes a coaptation element 1310 (e.g., a spacer, coaptation element, plug, etc.) for implantation between leaflets of a native valve. In some implementations, the anchor portion 1306 includes a plurality of anchors 1308. The anchors 1308 can be configured in a variety of ways, such as, for example, any way described in the present application.

In some implementations, an actuation element 1312 (e.g., actuation shaft, actuation rod, actuation tube, actuation wire, actuation line, etc.) extends from an implant catheter (e.g., implant catheter 202 shown in FIG. 43) to engage and enable actuation of the implantable device or implant 1300. For example, the actuation element 1312 can extend through and move relative to the capture mechanism, proximal collar, and coaptation element 1310 to engage a cap 1314 of the distal portion 1307. The actuation element 1312 can be configured to removably engage the cap 1314 with a threaded connection, or the like, so that the actuation element 1312 can move the device 1300 between the open and closed position, and so that the actuation element can be disengaged and removed from the device 1300 after implantation. The actuation element 1312 and the cap 1314 can take any suitable form, such as, for example, any form described in the present application.

In the illustrated example, the cap 1314 includes the indication feature 1301 that allows a user to determine if a tension force applied to the implantable device or implant 1300 has reached or exceeded a predetermined tension (e.g., a predetermined allowable tension, a pre-set tension, etc.) or an optimal tension range. For example, the cap 1314 includes a flexible membrane 1321 that is movable from a normal, substantially flat position to an expanded position or domed shape. The flexible membrane 1321 can be operatively connected to the anchors 1308 or the actuation element 1312 such that the flexible membrane can move to the expanded position when a tension force T is applied to the device 1300 via its connection with the leaflets 20, 22. When the tension force T is applied to the device 1300 by its connection with the leaflets 20, 22, the anchor portion 1308 may move to an open position in the outward direction M, which causes the flexible membrane 1321 to move to the expanded position in the direction Y relative to the cap 1314. When the device 1300 is attached to the leaflets 20, 22 and in the closed position, and the flexible membrane 1321 is in the expanded position, the indication feature 1301 is in an exceeded tension position where the tension force applied to the device 1300 has reached or exceeded the predetermined tension or optimal tension range. When the device 1300 is attached to the leaflets 20, 22 and in the closed position, and the flexible membrane 1321 is in the normal position, the indication feature 1301 is in an allowable tension position where the tension force applied to the device 1300 has not reached or exceeded the predetermined tension or is within an optimal tension range. The user can determine whether or not the flexible membrane 1321 is in the expanded or normal position by comparing the position flexible membrane 1321 relative to other components of the device 1300 (e.g., the remainder of the cap 1314, the coaptation element 1310, the anchor portion 1308, etc.), or the imaging software can be configured to determine when the flexible membrane 1321 is in the expanded position. In some implementations, the indication feature 901 can include a visual marking (e.g., a dot, an X-mark, a radiopaque marker, etc.) that allows a user to more easily determine if the flexible membrane 1321 is in the expanded position.

Figure 70:
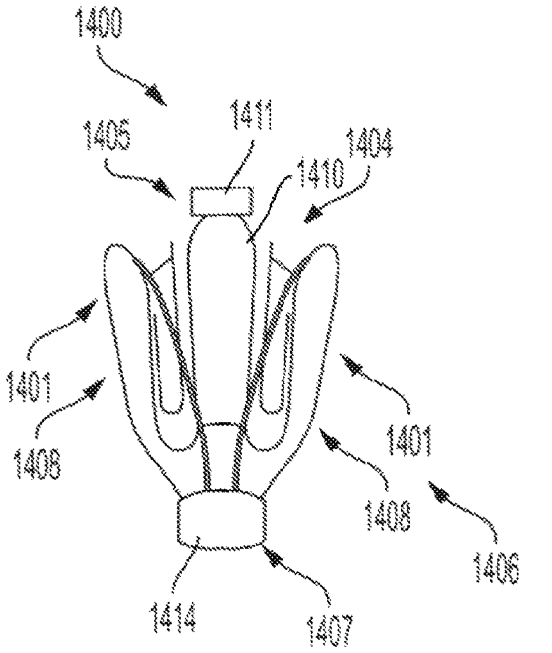
FIG. 70 shows an example of an implantable device or implant that includes an indication feature for allowing a user to determine if a tension applied to the implantable device or implant has reached or exceeded a pre-set or predetermined tension, where the indication feature is movable between an allowable tension position and an exceeded tension position.
Figure 71:
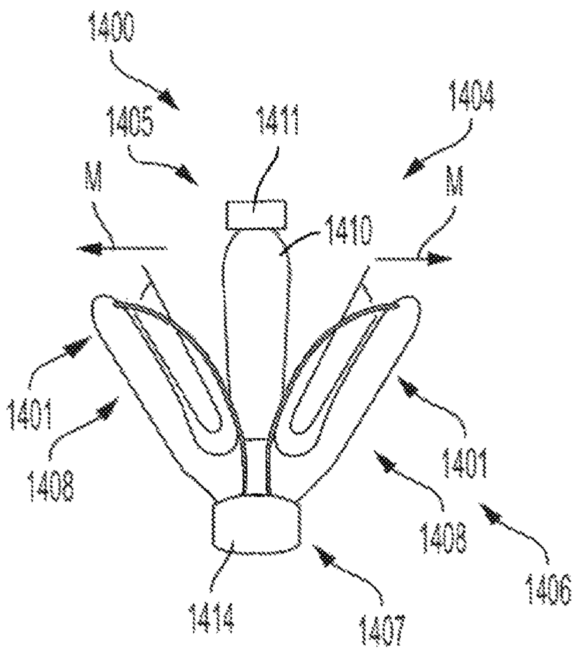
FIG. 71 shows the implantable device or implant of FIG. 70 where the indication feature is in the exceeded tension position.

FIGS. 70 and 71 show an example of an implantable device or implant 1400 that includes an indication feature 1401 that allows a user to determine if a tension force applied to the implantable device has reached or exceeded a predetermined tension (e.g., a predetermined allowable tension, a pre-set tension, etc.) or an optimal tension range. The device/implant of FIGS. 70 and 71 can be the same device as or similar to devices/implants illustrated by FIGS. 22-27 or any of the other devices and implants disclosed herein. In some implementations, the implantable device or implant is configured such that movement or opening of the paddles away from the center indicates that more than a pre-set or predetermined amount of tension force or more than an optimal tension force is applied to the clasp, anchors, and/or device. For example, movement or opening of the paddles away from a center or from an optional coaptation element or spacer can indicate that more than a predetermined amount or more than an optimal amount of tension force is applied to the clasp, anchors, and/or device. That is, the indication feature 1401 can be or comprise the components, configuration, and/or design of the device and anchors that allows the anchors or paddles to move or pull away from the center (or move apart to wider angle) to provide a visual indication to a user to excessive tension. This can be seen by viewing the connection between the device 1400 and the leaflets 20, 22 through direct, echocardiographic, or fluoroscopic imaging. If the indication feature 1401 is indicating to the user that the tension force applied to the device 1400 has reached or exceeded the predetermined tension or optimal tension range, the user can open the device 1400 to remove it from the leaflets 20, 22 and reconnect the device to a position in which the indication feature 1401 has not reached or exceeded the predetermined tension or optimal tension range.

The device 1400 can include the features of any suitable implantable device or implant, such as, for example, the features of the device shown in FIGS. 22-27, or any other device described in the present application. For example, the device 1400 can include a coaptation portion 1404, a proximal or attachment portion 1405 that can include an attachment collar 1411 (e.g., similar to the attachment portion 205 shown in FIGS. 22-37), an anchor portion 1406, and a distal portion 1407 that can include a cap 1414. In some implementations, the coaptation portion 1404 of the device optionally includes a coaptation element 1410 (e.g., a spacer, coaption element, plug, membrane, sheet, etc.) for implantation between leaflets of a native valve. The size and/or shape of the coaptation element 1410 can be selected to minimize the number of implants that a single patient will require (preferably one), while at the same time maintaining low transvalvular gradients. In some implementations, the anchor portion 1406 includes a plurality of anchors 1408. The anchors 1408 can be configured in a variety of ways, such as, for example, any way described in the present application.

In the illustrated example, the anchors 1408 include the indication feature 1401 (e.g., components, configuration, and/or design) that allows a user to determine if a tension force applied to the implantable device or implant 1400 has reached or exceeded a predetermined tension (e.g., a predetermined allowable tension, a pre-set tension, etc.) or an optimal tension range. For example, at least a portion of the anchors 1408 (e.g., paddles, clasps, etc.) can be made of a flexible or elastic material(s) that allows the anchors 1408 to bend, flex, and/or move in the outward direction M when a tension force is applied to the device 1400 via its connection with the leaflets of the native heart valve. In some implementations, if one or more of the anchors 1408 bend, flex, and/or move in the direction M to or above a predetermined amount, the indication feature 1401 is in an exceeded tension position (e.g., as shown in FIG. 71) where the tension force applied to the device 1400 has reached or exceeded the predetermined tension or optimal tension range. If the anchors 1408 do not extend to or above the predetermined amount, the indication feature 1401 is in an allowable tension position (e.g., as shown in FIG. 70) where the tension force applied to the device 1400 is below the predetermined tension or within the optimal tension range. The user can, for example, determine the amount of bending or flexing of the anchors 1408 by comparing the positioning of the anchors 1408 relative to other components of the device 1400 (e.g., the coaptation element 1410, etc.) and/or observing the angle between the anchors or paddles. In some implementations, imaging software can be configured to measure the positioning of the anchors 1408 relative to the other components of the device 1400 to determine if the indication feature is in the exceeded tension position. In some implementations, the indication feature 1401 can comprise a visual marking (e.g., a dot, an X-mark, a radiopaque marker, etc.) that allows a user to more easily determine if the indication feature 1401 is in the exceeded tension position.

Figure 70A:
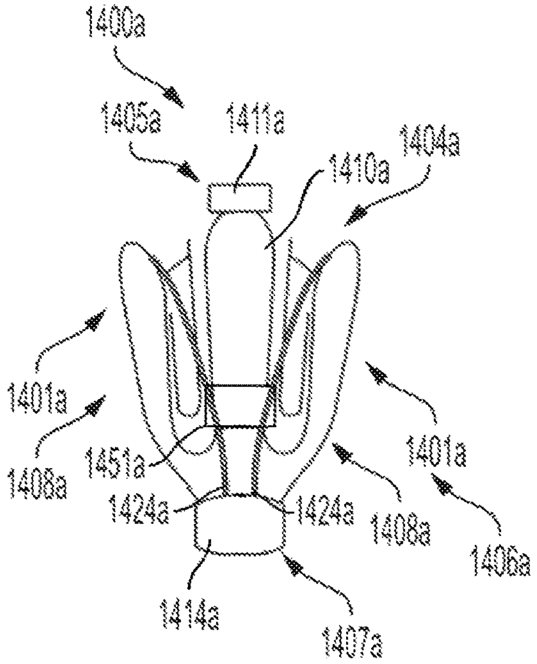
FIG. 70A shows an example of an implantable device or implant that includes an indication feature for allowing a user to determine if a tension applied to the implantable device or implant has reached or exceeded a pre-set or predetermined tension, where the indication feature is movable between an allowable tension position and an exceeded tension position, and where the implantable device or implant has a connection element for locking the implantable device or implant in a closed position.
Figure 71A:
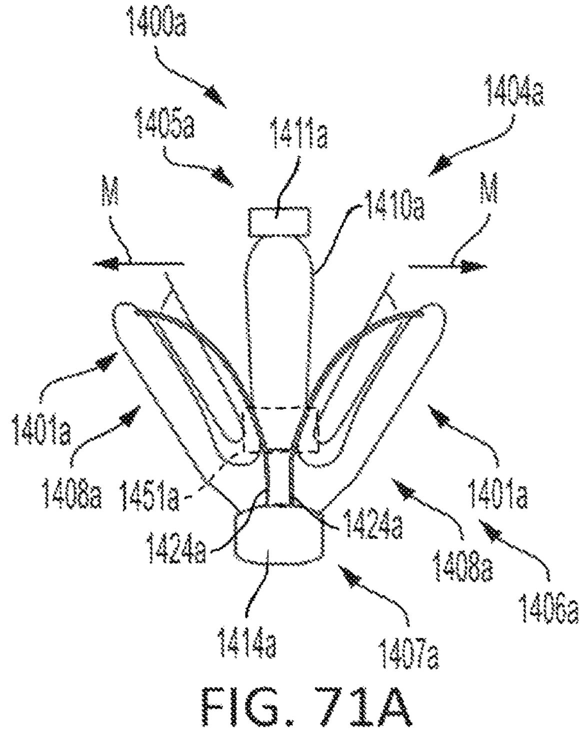
FIG. 71A shows the implantable device or implant of FIG. 70A where the indication feature is in the exceeded tension position.

FIGS. 70A and 71A show an example of an implantable device or implant 1400*a* that includes an indication feature 1401*a* that allows a user to determine if a tension force applied to the implantable device or implant has reached or exceeded a predetermined tension (e.g., a predetermined allowable tension, a pre-set tension, etc.) or an optimal tension range. This example also includes a connection element 1451*a* that can be used to lock the paddles of the implantable device or implant in a closed position once it is determined that the implantable device or implant 1400*a* has not reached or exceeded the predetermined tension or optimal tension range.

The prosthetic device of FIGS. 70A and 71A can be the same device illustrated by FIGS. 22-27 or any of the other devices and implants disclosed herein. In some implementations, the implantable device or implant is configured such that movement or opening of the paddles away from the center indicates that more than a pre-set or predetermined amount of tension force or more than an optimal tension force is applied to the clasp, anchors, and/or device. For example, movement or opening of the paddles away from a center or from an optional coaptation element or spacer can indicate that more than a pre-set or predetermined amount or more than an optimal range of tension force is applied to the clasp, anchors, and/or device. That is, the indication feature 1401*a* can be or comprise the components, configuration, and/or design of the device and anchors that allows the anchors or paddles to move or pull away from the center (or move apart to wider angle) to provide a visual indication to a user to excessive tension. This can be seen by viewing the connection between the device 1400*a* and the leaflets 20, 22 through direct, echocardiographic, or fluoroscopic imaging. If the indication feature 1401*a* is indicating to the user that the tension force applied to the device 1400*a* has reached or exceeded the predetermined tension or optimal tension range, the user can open the device 1400*a* to remove it from the leaflets 20, 22 and reconnect the device to a position in which the indication feature 1401*a* has not reached or exceeded the predetermined tension or optimal tension range.

The device 1400*a* can include the features of any suitable implantable device or implant, such as, for example, the features of the device shown in FIGS. 22-27, or any other device described in the present application. For example, the device 1400*a* can include a coaptation portion 1404*a*, a proximal or attachment portion 1405*a* that includes an attachment collar 1411*a* (e.g., similar to the attachment portion 205 shown in FIGS. 22-37), an anchor portion 1406*a*, and a distal portion 1407*a* that can include a cap 1414*a*. In some implementations, the coaptation portion 1404*a* of the device optionally includes a coaptation element 1410*a* (e.g., a spacer, coaption element, plug, membrane, sheet, etc.) for implantation between leaflets of a native valve. The size and/or shape of the coaptation element 1410*a* can be selected to minimize the number of implants that a single patient will require (preferably one), while at the same time maintaining low transvalvular gradients. In some implementations, the anchor portion 1406*a* includes a plurality of anchors 1408*a*. The anchors 1408*a* can be configured in a variety of ways, such as, for example, any way described in the present application.

In the illustrated example, the anchors 1408*a* include the indication feature 1401*a* that allows a user to determine if a tension force applied to the implantable device or implant 1400*a* has reached or exceeded a predetermined tension (e.g., a predetermined allowable tension, a pre-set tension, etc.) or an optimal tension range. For example, at least a portion of the anchors 1408*a* (e.g., paddles, clasps, etc.) can be made of a flexible or elastic material(s) that allows the anchors 1408*a* to bend, flex, and/or move in the outward direction M when a tension force is applied to the device 1400*a* via its connection with the leaflets of the native heart valve. In some implementations, if one or more of the anchors 1408*a* bend, flex, and/or move in the direction M to or above a predetermined amount, the indication feature 1401*a* is in an exceeded tension position (e.g., as shown in FIG. 71A) where the tension force applied to the device 1400*a* has reached or exceeded the predetermined tension or optimal tension range. If the anchors 1408*a* do not extend to or above the predetermined amount, the indication feature 1401*a* is in an allowable tension position (e.g., as shown in FIG. 70A) where the tension force applied to the device 1400*a* is below the predetermined tension or within the optimal tension range. The user can, for example, determine the amount of bending or flexing of the anchors 1408*a* by comparing the positioning of the anchors 1408*a* and/or paddles relative to other components of the device 1400*a* (e.g., the coaptation element 1410*a*, etc.) or center of the device, and/or looking at the angle between the anchors and/or paddles. In some implementations, the imaging software can be configured to measure the positioning of the anchors 1408*a* relative to the other components of the device 1400*a* to determine if the indication feature is in the exceeded tension position. In some implementations, the indication feature 1401*a* can include a visual marking (e.g., a dot, an X-mark, a radiopaque marker, etc.) that allows a user to more easily determine if the indication feature 1401*a* is in the exceeded tension position.

The connection element 1451*a* is in an unlocked state (as shown by the dashed lines in FIG. 71A) when the implantable device or implant 1400*a* is being connected to the native heart valve. Once connected to the native heart valve and the indication feature 1401*a* indicates that the tension force applied to the implantable device or implant has not reached or exceeded a predetermined tension or is within the optimal tension range, the connection element 1451*a* can be moved to a locked state (as shown by the solid lines in FIG. 70A) to maintain the anchors 1408*a* in the closed position and prevent movement of the anchors in the direction M relative to the spacer or coaptation element 1410*a*. In the illustrated example, the connection element 1451*a* is attached to the paddle frames 1424*a* of the anchors 1408*a* to secure the paddle frames 1424*a* of the anchors together when in the locked state. The connection element 1451*a* can, however, be connected to any other suitable portion of the anchors 1408*a*. The connection element 1451*a* can be, for example, a clasp, suture, clip, fastener, lock, clamp, connector, or any other suitable element for connecting the anchors 1408 together. The connection element 1451*a* can be moved from the unlocked state to the locked state by an actuation member (not shown), such as, for example, a wire, a suture, a rod, a threaded coupler, or any other suitable member for moving the connection element to the locked state. In some implementations, rather than the anchors 1408*a* being connected together, each anchor 1408*a* can include a separate locking element (not shown) that locks the positioning of the anchor 1408*a* relative to the coaptation element 1410*a* or any other portion of the device 1400*a* to prevent movement of the anchors 1408*a* in the direction M.

Figure 72:
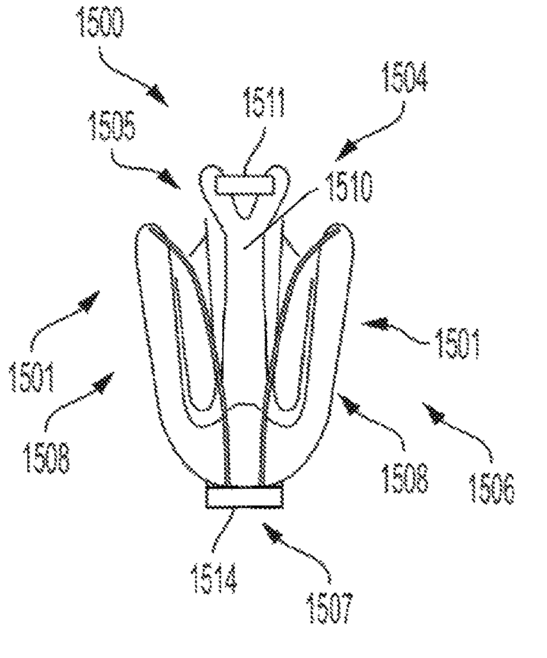
FIG. 72 shows an example of an implantable device or implant that includes an indication feature for allowing a user to determine if a tension applied to the implantable device or implant has reached or exceeded a pre-set or predetermined tension, where the indication feature is movable between an allowable tension position and an exceeded tension position.
Figure 73:
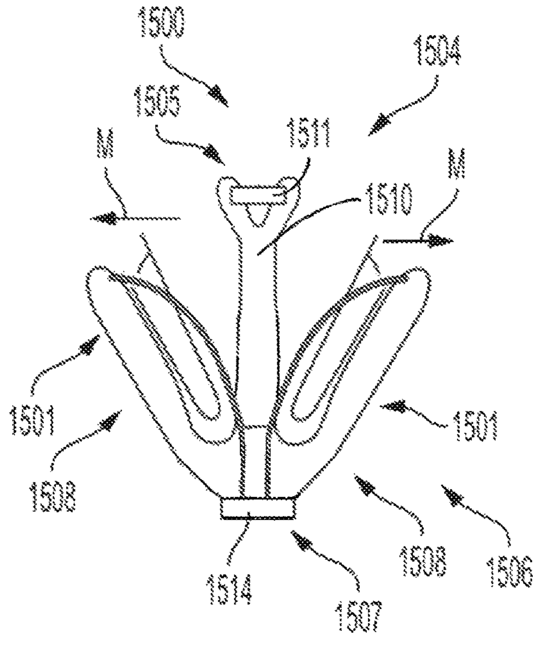
FIG. 73 shows the implantable device or implant of FIG. 72 where the indication feature is in the exceeded tension position.

FIGS. 72 and 73 show an example of an implantable device or implant 1500 that includes an indication feature 1501 that allows a user to determine if a tension force applied to the implantable device or implant has reached or exceeded a predetermined allowable tension. The prosthetic device of FIGS. 72 and 73 can be the same device illustrated by FIG. 55 or any of the other devices and implants disclosed herein. In some implementations, the implantable device or implant is configured such that movement or opening of the paddles away from the center indicates that more than a pre-set or predetermined amount of tension force or more than an optimal tension force is applied to the clasp, anchors, and/or device. For example, movement or opening of the paddles away from a center or from an optional coaptation element or spacer can indicate that more than a predetermined amount or more than an optimal range of tension force is applied to the clasp, anchors, and/or device. That is, the indication feature 1501 can be or comprise the components, configuration, and/or design of the device and anchors that allows the anchors or paddles to move or pull away from the center (or move apart to wider angle) to provide a visual indication to a user to excessive tension. This can be seen by viewing the connection between the device 1500 and the leaflets 20, 22 through direct, echocardiographic, or fluoroscopic imaging. If the indication feature 1501 is indicating to the user that the tension force applied to the device 1500 has reached or exceeded the predetermined tension amount or an optimal tension range, the user can open the device 1500 to remove it from the leaflets 20, 22 and reconnect the device to a position in which the indication feature 1501 has not reached or exceeded the predetermined tension or an optimal tension range.

The device 1500 can include the features of any suitable implantable device or implant, such as, for example, the features of the device 400 shown in FIG. 55, or any other device described in the present application. For example, the device 1500 can include a coaptation portion 1504, a proximal or attachment portion 1505 that includes an attachment collar 1511 (e.g., similar to the attachment portion 205 shown in FIGS. 22-37), an anchor portion 1506, and a distal portion 1507 that can include a cap 1514. In some implementations, the coaptation portion 1504 of the device optionally includes a coaptation element 1510 (e.g., a spacer, coaption element, plug, etc.) for implantation between leaflets of a native valve. The size and/or shape of the coaptation element 1510 can be selected to minimize the number of implants that a single patient will require (preferably one), while at the same time maintaining low transvalvular gradients. In some implementations, the anchor portion 1506 includes a plurality of anchors 1508. The anchors 1508 can be configured in a variety of ways, such as, for example, any way described in the present application.

In the illustrated example, the anchors 1508 include the indication feature 1501 (e.g., components, configuration, design, etc.) that allows a user to determine if a tension force applied to the implantable device or implant 1500 has reached or exceeded a predetermined tension (e.g., a predetermined allowable tension, a pre-set tension, etc.) or an optimal tension range. For example, at least a portion of the anchors 1508 (e.g., paddles, clasps, etc.) can be made of a flexible or elastic material(s) that allows the anchors 1508 to bend, flex, and/or move in the outward direction M when a tension force is applied to the device 1500 via its connection with the leaflets of a native heart valve. In some implementations, if one or more of the anchors 1508 bend, flex, and/or move in the direction M to or above a predetermined amount, the indication feature 1501 is in an exceeded tension position (e.g., as shown in FIG. 73) where the tension force applied to the device 1500 has reached or exceeded the predetermined tension or the optimal tension range. If the anchors 1508 do not extend to or above the predetermined amount, the indication feature 1501 is in an allowable tension position (e.g., as shown in FIG. 72) where the tension force applied to the device 1500 is below the predetermined tension or within the optimal tension range. The user can, for example, determine the amount of bending, flexing, and/or movement of the anchors 1508 (or increased angle of the anchors/paddles) by comparing the positioning of the anchors 1508 relative to other components of the device 1500 (e.g., the coaptation element 1510, etc.). In some implementations, imaging software can be configured to measure the positioning of the anchors 1508 relative to the center or other components of the device 1500 (and/or measure the angle between the anchors and/or paddles) to determine if the indication feature is in the exceeded tension position. In some implementations, the indication feature 1501 can include a visual marking (e.g., a dot, an X-mark, etc.) that allows a user to more easily determine if the indication feature 1501 is in the exceeded tension position.

Figure 72A:
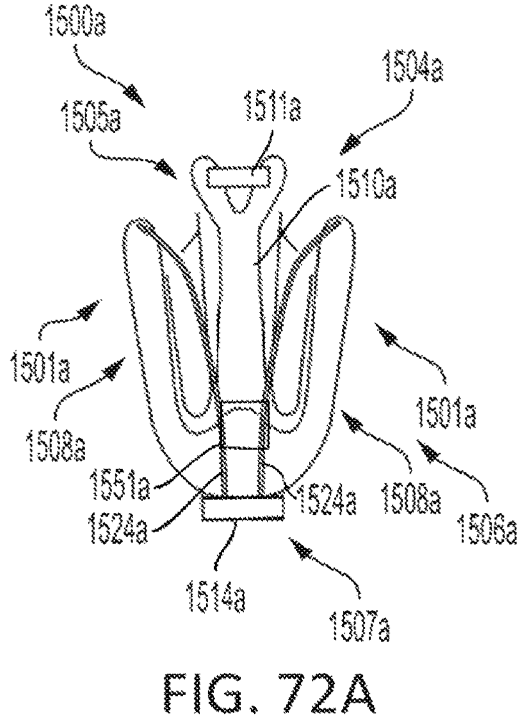
FIG. 72A shows an example of an implantable device or implant that includes an indication feature for allowing a user to determine if a tension applied to the implantable device or implant has reached or exceeded a pre-set or predetermined tension, where the indication feature is movable between an allowable tension position and an exceeded tension position and where the implantable device or implant has a connection element for locking the implantable device or implant in a closed position.
Figure 73A:
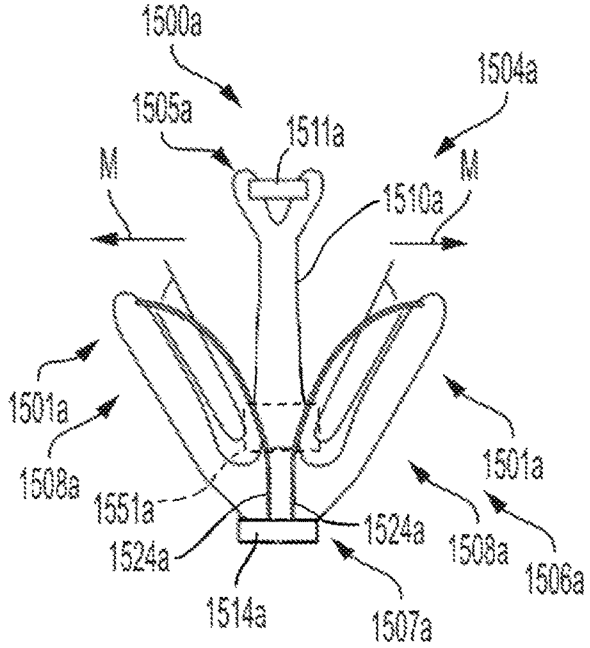
FIG. 73A shows the implantable device or implant of FIG. 72A where the indication feature is in the exceeded tension position.

FIGS. 72A and 73A show an example of an implantable device or implant 1500*a* that includes an indication feature 1501*a* that allows a user to determine if a tension force applied to the implantable device or implant has reached or exceeded a predetermined tension (e.g., a predetermined allowable tension, a pre-set tension, etc.) or an optimal tension range. This example also includes a connection element 1551*a* that can be used to lock the paddles of the implantable device or implant in a closed position once it is determined that the implantable device or implant 1500*a* has not reached or has exceeded the predetermined tension amount or optimal tension range.

The prosthetic device of FIGS. 72A and 73A can be the same device illustrated by FIG. 55 or any of the other devices and implants disclosed herein. In some implementations, the implantable device or implant is configured such that movement or opening of the paddles away from the center indicates that more than a pre-set or predetermined amount of tension force or more than an optimal tension force is applied to the clasp, anchors, and/or device. For example, movement or opening of the paddles away from a center or from an optional coaptation element or spacer can indicate that more than a predetermined amount or more than an optimal amount of tension force is applied to the clasp, anchors, and/or device. That is, the indication feature 1501 can be or comprise the components, configuration, and/or design of the device and anchors that allows the anchors or paddles to move or pull away from the center (or move apart to wider angle) to provide a visual indication to a user to excessive tension. This can be seen by viewing the connection between the device 1500*a* and the leaflets 20, 22 through direct, echocardiographic, or fluoroscopic imaging. If the indication feature 1501*a* is indicating to the user that the tension force applied to the device 1500*a* has reached or exceeded the predetermined tension or an optimal tension range, the user can open the device 1500*a* to remove it from the leaflets 20, 22 and reconnect the device to a position in which the indication feature 1501*a* has not reached or exceeded the predetermine tension or optimal tension range.

The device 1500*a* can include the features of any suitable implantable device or implant, such as, for example, the features of the device 400 shown in FIG. 55, or any other device described in the present application. For example, the device 1500*a* can include a coaptation portion 1504*a*, a proximal or attachment portion 1505*a* that includes an attachment collar 1511*a* (e.g., similar to the attachment portion 205 shown in FIGS. 22-37), an anchor portion 1506*a*, and a distal portion 1507*a* that can include a cap. In some implementations, the coaptation portion 1504*a* of the device optionally includes a coaptation element 1510*a* (e.g., a spacer, coaption element, plug, etc.) for implantation between leaflets of a native valve. The size and/or shape of the coaptation element 1510*a* can be selected to minimize the number of implants that a single patient will require (preferably one), while at the same time maintaining low transvalvular gradients. In some implementations, the anchor portion 1506*a* includes a plurality of anchors 1508*a*. The anchors 1508*a* can be configured in a variety of ways, such as, for example, any way described in the present application.

In the illustrated example, the anchors 1508*a* include the indication feature 1501*a* (e.g., components, configuration, design, etc.) that allows a user to determine if a tension force applied to the implantable device or implant 1500*a* has reached or exceeded a predetermined tension (e.g., a predetermined allowable tension, a pre-set tension, etc.) or an optimal tension range. For example, at least a portion of the anchors 1508*a* (e.g., paddles, clasps, etc.) can be made of a flexible or elastic material(s) that allows the anchors 1508*a* to bend, flex, and/or move in the outward direction M when a tension force is applied to the device 1500*a* via its connection with the leaflets of a native heart valve. In some implementations, if one or more of the anchors 1508*a* bend, flex, and/or move in the direction M to or above a predetermined amount, the indication feature 1501*a* is in an exceeded tension position (e.g., as shown in FIG. 73A) where the tension force applied to the device 1500*a* has reached or exceeded the predetermined tension or optimal tension range. If the anchors 1508*a* do not extend to or beyond the predetermined amount, the indication feature 1501*a* is in an allowable tension position (e.g., as shown in FIG. 72A) where the tension force applied to the device 1500*a* is below the predetermined tension or within the optimal tension range. The user can, for example, determine the amount of bending or flexing of the anchors 1508*a* by comparing the positioning of the anchors 1508*a* relative to the center or to other components of the device 1500*a* (e.g., the coaptation element 1510*a*, etc.) and/or by observing the angle between the anchors/paddles. In some implementations, imaging software can be configured to measure the positioning of the anchors 1508*a* relative to the other components of the device 1500*a* to determine if the indication feature is in the exceeded tension position. In some implementations, the indication feature 1501*a* can include a visual marking (e.g., a dot, an X-mark, etc.) that allows a user to more easily determine if the indication feature 1501*a* is in the exceeded tension position.

The connection element 1551*a* is in an unlocked state (as shown by the dashed lines in FIG. 73A) when the implantable device or implant 1500*a* is being connected to the native heart valve. Once connected to the native heart valve and the indication feature 1501*a* indicates that the tension force applied to the implantable device or implant has not reached or exceeded a predetermined tension or an optimal tension range, the connection element 1551*a* can be moved to a locked state (as shown by the solid lines in FIG. 72*a*) to maintain the anchors 1508*a* in the closed position and prevent movement of the anchors in the direction M relative to the coaptation element 1510*a*. In the illustrated example, the connection element 1551*a* is attached to the paddle frames 1524*a* of the anchors 1508*a* to secure the paddle frames 1524*a* of the anchors together when in the locked state. The connection element 1551*a* can, however, be connected to any other suitable portion of the anchors 1508*a*. The connection element 1551*a* can be, for example, a clasp, suture, clip, fastener, lock, clamp, connector, or any other suitable element for connecting the anchors 1508 together. The connection element 1551*a* can be moved from the unlocked state to the locked state by an actuation member (not shown), such as, for example, a wire, a suture, a rod, a threaded shaft, or any other suitable member for moving the connection element to the locked state. In some implementations, rather than the anchors 1508*a* being connected together, each anchor 1408*a* can include a separate locking element (not shown) that locks the positioning of the anchor 1508*a* relative to the coaptation element 1510*a* or any other portion of the device 1400*a* to prevent movement of the anchors 1408*a* in the direction M.

FIGS. 74-77 show an example where a clasp 24100 is configured to allow a user to determine if a tension force applied to the implantable device or implant has reached or exceeded a predetermined tension (e.g., a predetermined allowable tension, a pre-set tension, etc.) or an optimal tension range. The clasp 24100 can be used with any of the prosthetic devices disclosed herein. In some implementations, flexing of the barbs 24104 and/or the barb support portion 24106 relative to the moveable arm of the clasp indicates that more than a pre-set or predetermined amount of tension force is applied to the clasp. For example, flexing of the barbs 24104 and/or the barb support portion 24106 more than a pre-set or predetermined angle, such as 30 degrees can indicate that more than a pre-set or predetermined amount of tension force is applied to the clasp.

Figure 74:
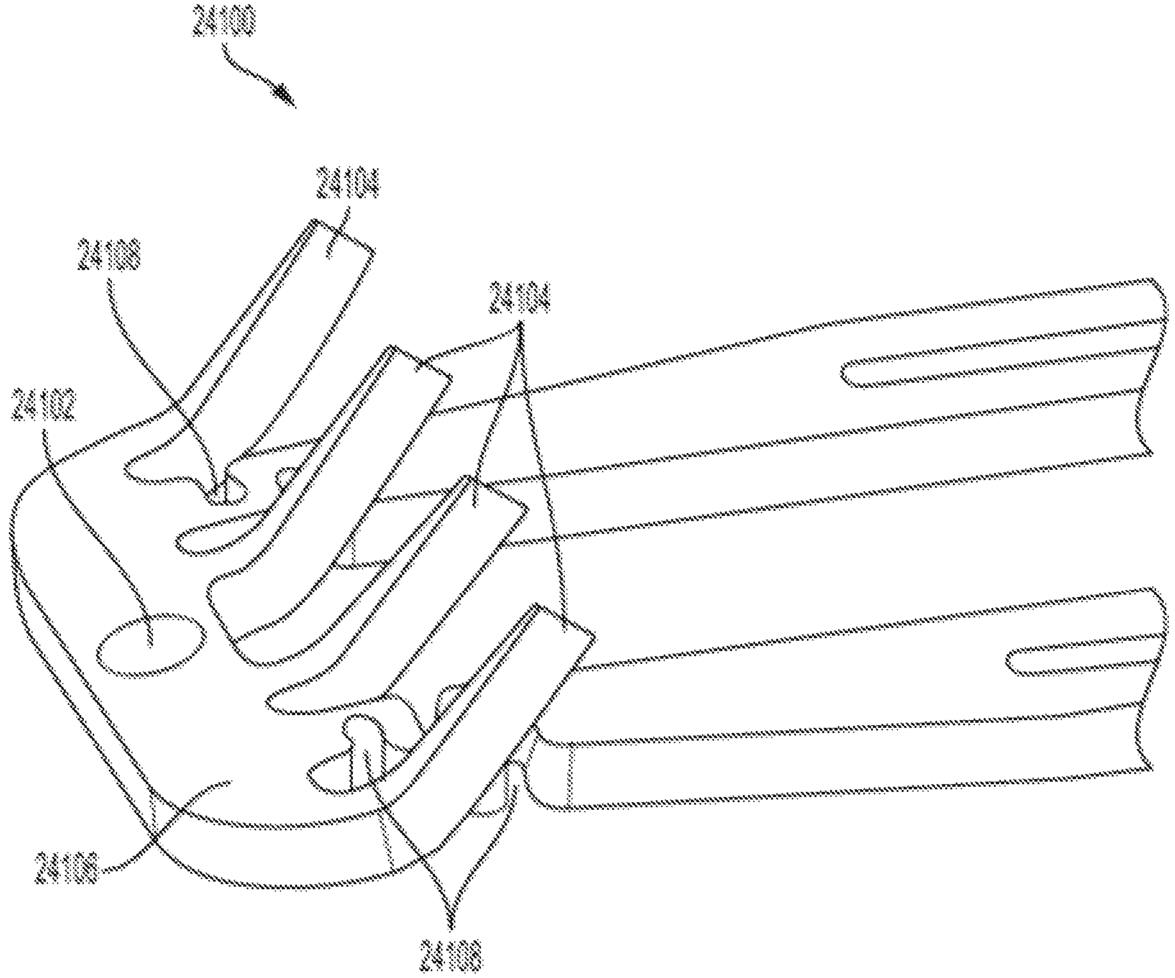
FIG. 74 shows an example of a clasp for an implantable device or implant, where the clasp includes an indication feature for allowing a user to determine if a tension applied to the implantable device or implant has reached or exceeded a pre-set or predetermined tension, and where the indication feature is movable between an allowable tension position and an exceeded tension position.
Figure 75:
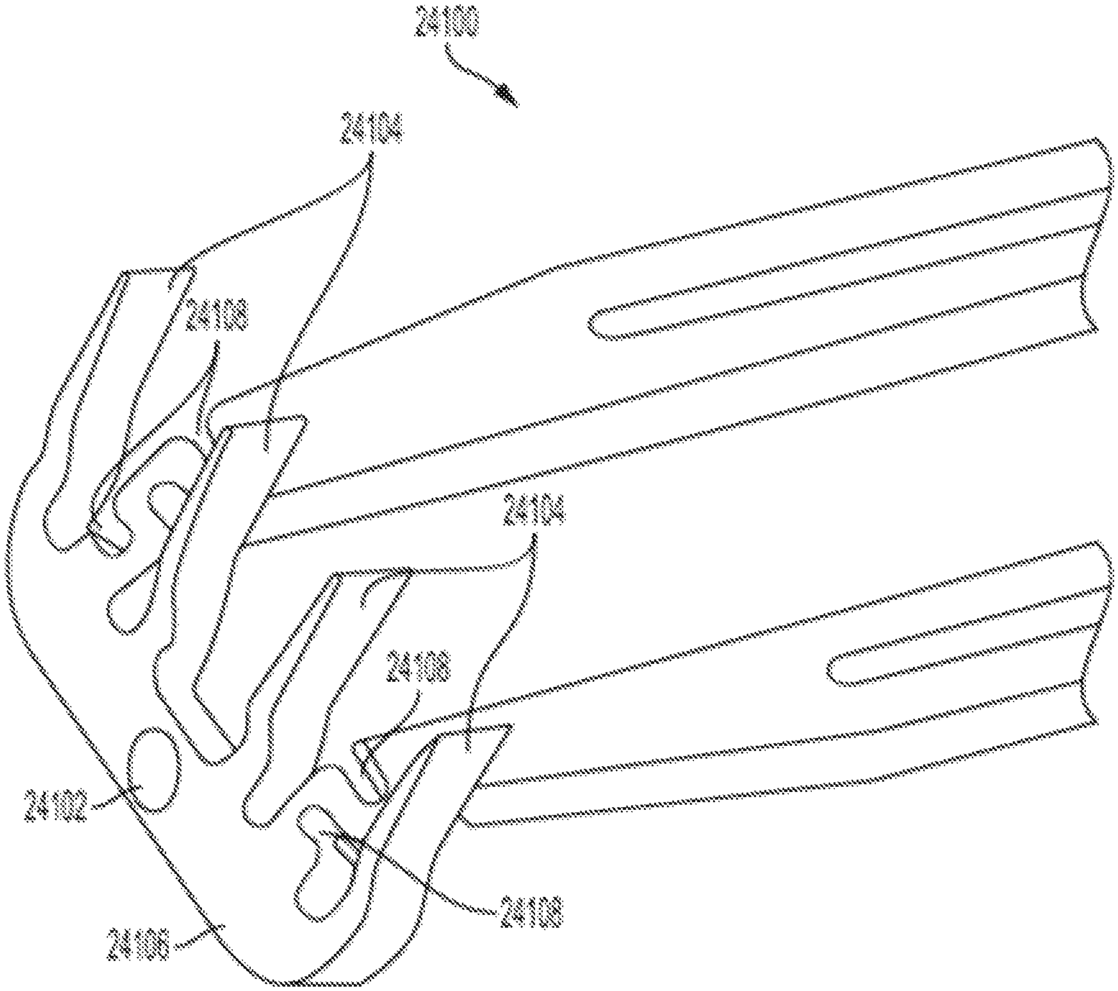
FIG. 75 shows the clasp of FIG. 74 where the indication feature is in the exceeded tension position.

Referring to FIGS. 74 and 75, an example of a barbed portion of a clasp 24100 is illustrated. Shown is an optional eyelet 24102 and barbs 24104 which are located in a barb support portion 24106 of the clasp 24100. Visible in the figure are portions of the clasp 24100 that are configured to increase the flexibility of the barb support portion 24106 of the clasp 24100. The increase of the flexibility of the barb support portion 24106 of the clasp 24100 can be accomplished in a wide variety of different ways. In some implementations, as illustrated, cutouts 24108 increase the flexibility of the barb support portion 24106 of the clasp 24100. However, in some implementations, the flexibility can be increased by reducing the thickness in a select area or areas, making portions of the clasp from different materials, heat and or chemical treatment of different portions of the clasps, etc. Any manner of increasing the barb support portion can be used.

In some implementations, the flexibility of the barb support portion 24106 is configured such that the barbs rotate and pull out of the leaflet upon application of a pre-set or predetermined pulling force. In some implementations, the pre-set or predetermined pulling force is selected such that the paddles and paddle frames first flex and open or partially open and then the barbs rotate and pull out of the leaflet. FIG. 74 illustrates the barb support in a "normal" or unflexed position while FIG. 75 illustrates the barb support portion 24106 of the clasp 24100 in a flexed position.

Figure 76:
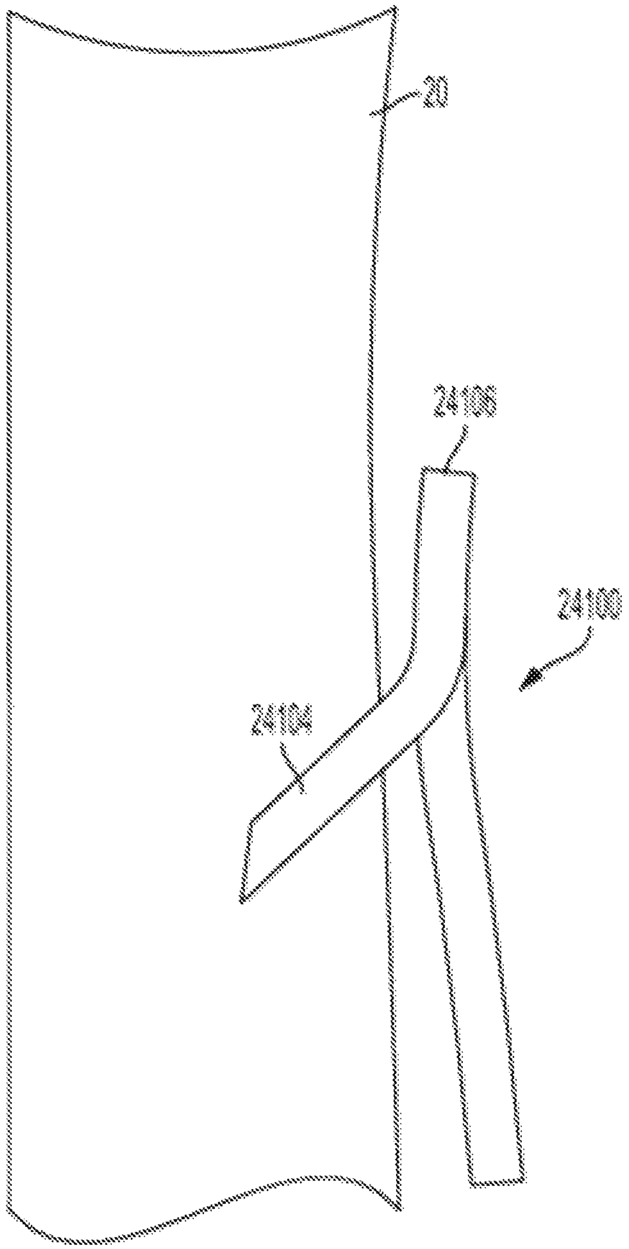
FIG. 76 shows the clasp of FIG. 74 attached to a leaflet of a native heart valve, where the indication feature is in an allowable tension position.
Figure 77:
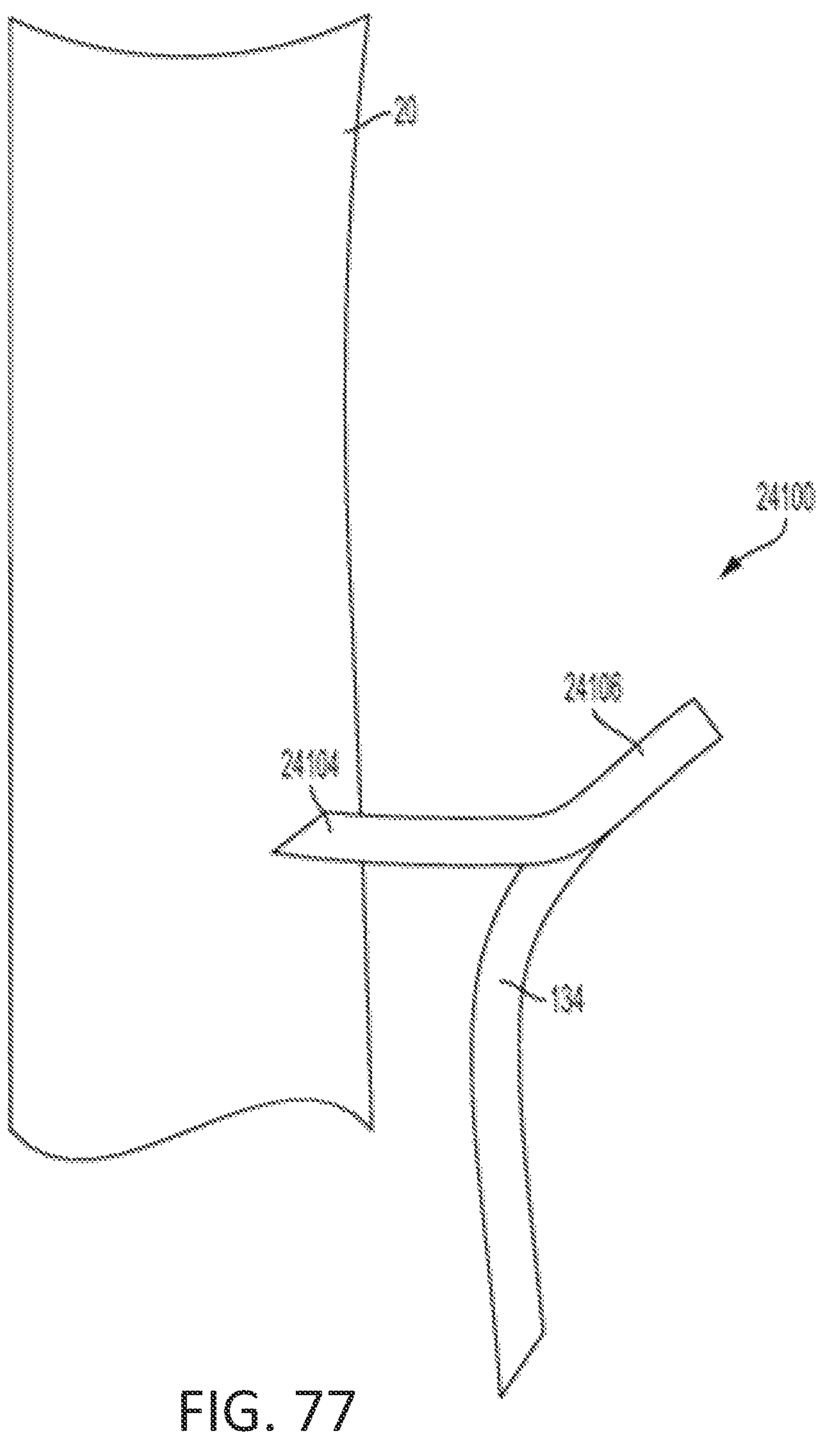
FIG. 77 shows the clasp of FIG. 74 attached to a leaflet of a native heart valve, where the indication feature is in an exceeded tension position.

FIGS. 76-77 illustrate an example behavior of a clasp configured according to FIGS. 74 and 75. FIG. 77 illustrate the barb support portion 24106 as tension is applied between the clasp 24100 and the leaflet 20. The tension can be applied for a variety of different reasons. In some implementations, the tension results from capturing the leaflets with the clasps, manipulating one leaflet while a second leaflet is captured, closing of the paddles after the leaflet is grasped by the clasp and/or pressure applied to the device by blood due to the beating of the heart.

In FIG. 76, the barbs 24104 of the clasp 24100 are embedded in a leaflet 20 (only a small portion of the leaflet is illustrated). In use with a prosthetic device 100, 200, 300 (See FIGS. 14, 26, 55), the clasp is affixed at the base of the paddle. As mentioned above, various situations can cause tension to be applied such that the barb of the clasp pulls against the leaflet. This tension could be caused by the leaflet 20 moving upward and/or laterally while the clasp 24100 remains stationary, the leaflet 20 remaining stationary while the clasp 24100 moves downward and/or laterally, or a combination in which both the leaflet 20 and the clasp 24100 moves. In each instance, tension between the leaflet 20 and the clasp 24100 results. As the application of tension continues, the barb support portion 24106 to rotates away from the leaflet 20 in a clockwise motion relative to the moveable arm 134 of the clasp (as illustrated in FIG. 77). The amount of rotation can be used to determine if a tension force applied to the clasps 24100 has reached or exceeded a predetermined tension (e.g., a predetermined allowable tension, a pre-set tension, etc.) or an optimal tension range.

The user can, for example, determine the amount of rotation of the barbs 24104 and/or barb support portion 24106 by comparing the positioning of the barbs 24104 and/or barb support portion 24106 relative to other components of the device (e.g., the moveable clasp arm, the fixed clasp arm, etc.), or the imaging software can be configured to measure the positioning of the barbs 24104 and/or barb support portion 24106 relative to the other components of the device to determine if the indication feature is in the exceeded tension position. In some implementations, the barbs 24104 and/or barb support portion 24106 can include a visual marking (e.g., a dot, an X-mark, a radiopaque marker, etc.) that allows a user to more easily determine if the barbs 24104 and/or barb support portion 24106 are in the exceeded tension position.

Figure 78:
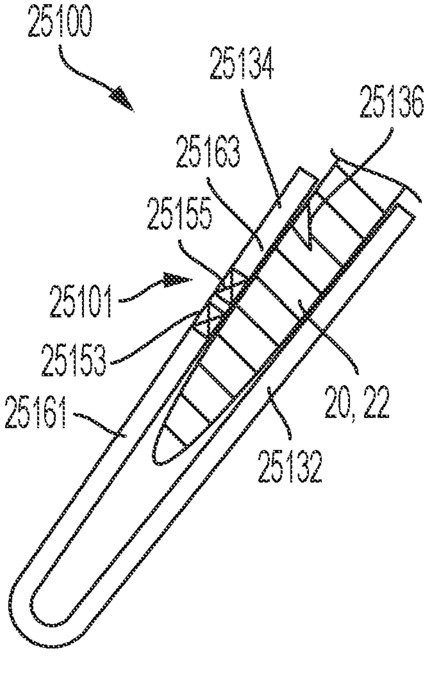
FIG. 78 shows an example of a clasp for an implantable device or implant attached to a leaflet of a native heart valve, where the clasp includes an indication feature for allowing a user to determine if a tension applied to the implantable device or implant has reached or exceeded a pre-set or predetermined tension, and where the indication feature is movable between an allowable tension position and an exceeded tension position.
Figure 79:
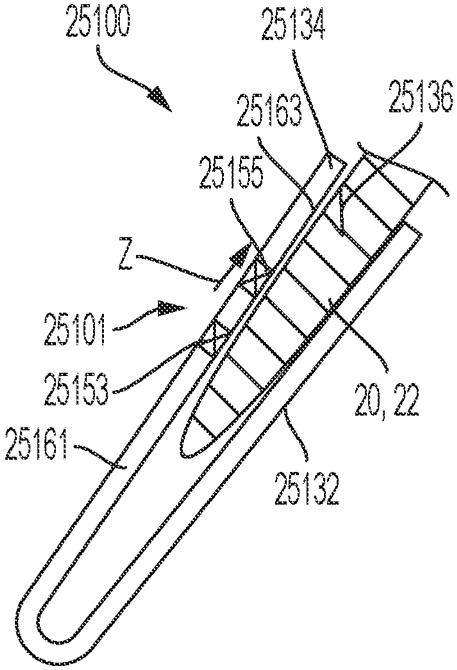
FIG. 79 shows the clasp of FIG. 78 where the indication feature is in the exceeded tension position.

FIGS. 78 and 79 show an example where a clasp 25100 is configured to allow a user to determine if a tension force applied to the implantable device or implant has reached or exceeded a predetermined tension (e.g., a predetermined allowable tension, a pre-set tension, etc.) or an optimal tension range. The clasp 25100 can be used with any of the prosthetic devices disclosed herein and can include the features of any of the clasps disclosed herein. For example, in some implementations, the clasps can include a fixed arm 25132 that is attached to paddles of the device and a movable arm 25134, where the movable arm 25134 has one or more barbs 25136 for connecting to a leaflet 20, 22 of a native heart valve.

The clasp 25100 can have an indication feature 25101 that includes a first visual marking 25153 and a second visual marking 25155. The visual markings 25153, 25155 can include, for example, a dot, an X-mark, a radiopaque marker, or any other suitable marking that is visible to a user using imaging technology, such as fluoroscopy, magnetic resonance imaging, echocardiography imaging, etc. A first portion 25161 of the clasp 25100 can include the first visual marking 25153 and a second portion 25163 of the clasp 25100 can include the second visual marking 25155. When a tension force is applied to the implantable device or implant, the second portion 25163 of the clasp 25100 can move relative to the first portion 25161 such that the second visual marking 25155 moves relative to the first visual marking 25153.

In some implementations, the first portion 25161 of the clasp 25100 is configured to maintain a substantially fixed position when a tension force is applied to the implantable device or implant, and the second portion 25163 is stretchable such that the second portion 25163 and, consequently, the second visual marking 25155 moves relative to the first visual marking 25153 in a direction Z (FIG. 79) when a tension force is applied to the implantable device or implant. The second visual marking 25155 can be configured to maintain its position relative to the first visual marking 25153 until the tension force has reached or exceeded the predetermined tension or optimal tension range, or the second visual marking 25155 can be configured to move when the tension force is applied to the implantable device or implant and the determination as to whether the predetermined tension or optimal tension range has been reached or exceeded is based on the distance that the second visual marking 25155 has moved from the first visual marking 25153.

Figure 80:
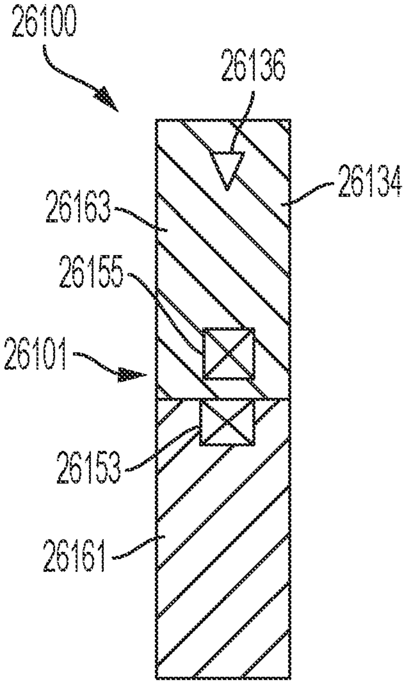
FIG. 80 shows an example of a clasp that includes an indication feature for allowing a user to determine if a tension applied to the implantable device or implant has reached or exceeded a pre-set or predetermined tension, where the indication feature is movable between an allowable tension position and an exceeded tension position.

FIG. 80 shows an example where a clasp 26100 is configured to allow a user to determine if a tension force applied to the implantable device or implant has reached or exceeded a predetermined tension (e.g., a predetermined allowable tension, a pre-set tension, etc.) or an optimal tension range. The clasp 26100 can be used with any of the prosthetic devices disclosed herein and can include the features of any of the clasps disclosed herein. For example, in some implementations, the clasps can include a fixed arm (not shown) that is attached to paddles of the device and a movable arm 26134, where the movable arm 26134 has one or more barbs 26136 for connecting to a native heart valve.

The clasp 26100 can have an indication feature 26101 that includes a first visual marking 26153 and a second visual marking 26155. The visual markings 26153, 26155 can include, for example, a dot, an X-mark, a radiopaque marker, or any other suitable marking that is visible to a user under visualization techniques, such as fluoroscopy, echocardiography, magnetic resonance imaging, etc. A first portion 26161 of the clasp 26100 can include the first visual marking 26153 and a second portion 26163 of the clasp 26100 can include the second visual marking 26155. In the illustrated example, the first portion 26161 of the clasp 26100 is made of a stiff material and the second portion 26163 is made of a stretchable material. When a tension force is applied to the implantable device or implant, the second portion 26163 of the clasp 26100 stretches relative to the first portion 26161 such that the second visual marking 26155 moves relative to the first visual marking 26153. The second portion 26163 can be configured to maintain its position relative to the first portion 26161 until the tension force has reached or exceeded the predetermined tension or optimal tension range, or the second portion 26163 can be configured to move when the tension force is applied to the implantable device or implant and the determination as to whether the predetermined tension or optimal tension range has been reached or exceeded is based on the distance that the second visual marking 26155 has moved from the first visual marking 26153.

Figure 81:
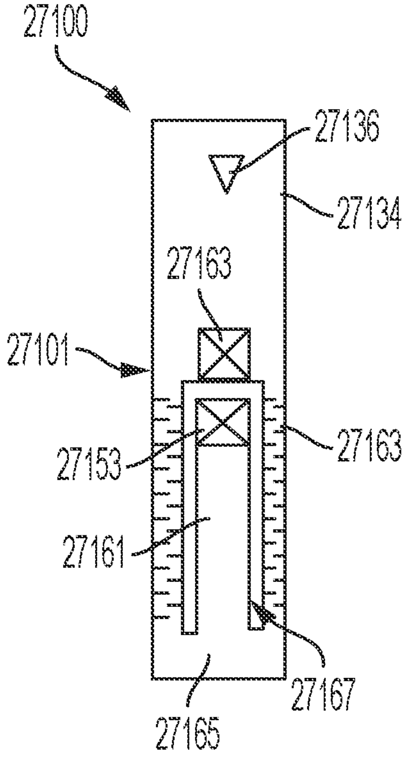
FIG. 81 shows an example of a clasp that includes an indication feature for allowing a user to determine if a tension applied to the implantable device or implant has reached or exceeded a pre-set or predetermined tension, where the indication feature is movable between an allowable tension position and an exceeded tension position.

FIG. 81 shows an example where a clasp 27100 is configured to allow a user to determine if a tension force applied to the implantable device or implant has reached or exceeded a predetermined tension (e.g., a predetermined allowable tension, a pre-set tension, etc.) or an optimal tension range. The clasp 27100 can be used with any of the prosthetic devices disclosed herein and can include the features of any of the clasps disclosed herein. For example, in some implementations, the clasps can include a fixed arm (not shown) that is attached to paddles of the device and a movable arm 27134, where the movable arm 27134 has one or more barbs 27136 for connecting to a native heart valve.

The clasp 27100 can have an indication feature 27101 that includes a first visual marking 27153 and a second visual marking 27155. The visual markings 27153, 27155 can include, for example, a dot, an X-mark, a radiopaque marker, or any other suitable marking that is visible to a user. A first portion 27161 of the clasp 27100 can include the first visual marking 27153 and a second portion 27163 of the clasp 27100 can include the second visual marking 27155. In the illustrated example, the second portion 27163 of the clasp 27100 is made of a stretchable material, and the first portion 27161 is decoupled from the stretchable second portion 27163 such that stretching of the second portion 27163 does not adjust the positioning of the first portion 27161. For example, in the illustrated example, the first and second portions 27161, 27163 are both attached to a fixed portion 27165 of the clasp, but the first portion 27161 is disposed within a cutout 27167 of the second portion 27163 such that stretching of the second portion 27163 does not cause the first portion 27161 to move relative to the fixed portion 27165 of the clasp 27100. When a tension force is applied to the implantable device or implant, the second portion 27163 of the clasp 27100 stretches relative to the first portion 27161 such that the second visual marking 27155 moves relative to the first visual marking 27153. The second portion 27163 can be configured to maintain its position relative to the first portion 27161 until the tension force has reached or exceeded the predetermined tension or optimal tension range, or the second portion 27163 can be configured to move when the tension force is applied to the implantable device or implant and the determination as to whether the predetermined tension or optimal tension range has been reached or exceeded is based on the distance that the second visual marking 27155 has moved from the first visual marking 27153.

While the examples shown in FIGS. 78-81 show the indication features being on the clasps of the implantable device or implant, it should be understood that the indication features disclosed in these examples can be placed on other portions of the implantable device or implant. For example, rather than the clasps, the paddles can include the first and second visual markings that indicate to the user that the amount While various inventive aspects, concepts and features of the disclosures may be described and illustrated herein as embodied in combination in the examples herein, these various aspects, concepts, and features may be used in many alternative examples, either individually or in various combinations and sub-combinations thereof. Unless expressly excluded herein all such combinations and sub-combinations are intended to be within the scope of the present application. Still further, while various alternative examples as to the various aspects, concepts, and features of the disclosures-such as alternative materials, structures, configurations, methods, devices, and components, alternatives as to form, fit, and function, and so on—may be described herein, such descriptions are not intended to be a complete or exhaustive list of available alternative examples, whether presently known or later developed. Those skilled in the art may readily adopt one or more of the inventive aspects, concepts, or features into additional examples and uses within the scope of the present application even if such examples are not expressly disclosed herein.

Additionally, even though some features, concepts, or aspects of the disclosures may be described herein as being a preferred arrangement or method, such description is not intended to suggest that such feature is required or necessary unless expressly so stated. Still further, example or representative values and ranges may be included to assist in understanding the present application, however, such values and ranges are not to be construed in a limiting sense and are intended to be critical values or ranges only if so expressly stated.

Moreover, while various aspects, features and concepts may be expressly identified herein as being inventive or forming part of a disclosure, such identification is not intended to be exclusive, but rather there may be inventive aspects, concepts, and features that are fully described herein without being expressly identified as such or as part of a specific disclosure, the disclosures instead being set forth in the appended claims. Descriptions of example methods or processes are not limited to inclusion of all steps as being required in all cases, nor is the order that the steps are presented to be construed as required or necessary unless expressly so stated. The words used in the claims have their full ordinary meanings and are not limited in any way by the description of the examples in the specification.

What is claimed is:

1. A valve repair device, comprising:

an anchor portion comprising a first clasp and a second clasp;

wherein the first clasp includes a fixed arm and a movable arm that is movably connected to the fixed arm of the first clasp;

wherein the first clasp is configured to move between an open position and a closed position;

wherein the first clasp is configured to attach to a first leaflet of a native heart valve;

wherein the second clasp includes a fixed arm and a movable arm that is movably connected to the fixed arm of the second clasp;

wherein the second clasp is configured to move between an open position and a closed position;

wherein the second clasp is configured to attach to a second leaflet of the native heart valve;

an indication feature comprising a flexible material of the movable arm of the first clasp that allows the movable arm of the first clasp to be in a non-extended position when the indication feature is in a first tension position and an extended position when the indication feature is in a second tension position;

wherein when the first clasp and the second clasp are attached to the first and second leaflets of the native heart valve, the second tension position indicates to a user when an amount of force applied to the anchor portion by the first and second leaflets of the native heart valve exceeds a predetermined amount of force.

2. The valve repair device of claim 1 further comprising a first paddle and a second paddle, wherein the first paddle and the second paddle are each moveable between an open position and a closed position.

3. The valve repair device of claim 2 wherein the movable arm of the first clasp and the movable arm of the second clasp are between the first paddle and the second paddle when the first paddle is in the closed position and the second paddle is in the closed position.

4. The valve repair device of claim 2 wherein an end of the movable arm of the first clasp extends past an end of the first paddle when the movable arm of the first clasp is in the extended position.

5. The valve repair device of claim 2 further comprising a spacer, wherein the spacer is disposed between the movable arm of the first clasp and the movable arm of the second clasp when the first paddle is in the closed position and the second paddle is in the closed position.

6. A valve repair system for repairing a native heart valve of a patient during a non-open-heart procedure, the valve repair system comprising:

a delivery device having at least one lumen;

an actuation element that extends through the delivery device;

an anchor portion comprising a first clasp and a second clasp;

wherein the first clasp includes a fixed arm and a movable arm that is movably connected to the fixed arm of the first clasp;

wherein the first clasp is configured to move between an open position and a closed position;

wherein the first clasp is configured to attach to a first leaflet of a native heart valve;

wherein the second clasp includes a fixed arm and a movable arm that is movably connected to the fixed arm of the second clasp;

wherein the second clasp is configured to move between an open position and a closed position;

wherein the second clasp is configured to attach to a second leaflet of the native heart valve;

an indication feature that comprising a flexible material of the movable arm of the first clasp that allows the movable arm of the first clasp to be in a non-extended position when the indication feature is in a first tension position and an extended position when the indication feature is in a second tension position; and wherein when the first clasp and the second clasp are attached to the first and second leaflets of the native heart valve, the second tension position indicates to a user when an amount of force applied to the anchor portion by the first and second leaflets of the native heart valve exceeds a predetermined amount of force.

7. The valve repair system of claim 6 further comprising a first paddle and a second paddle, wherein the first paddle and the second paddle are each moveable between an open position and a closed position.

8. The valve repair system of claim 7 wherein the movable arm of the first clasp and the movable arm of the second clasp are between the first paddle and the second paddle when the first paddle is in the closed position and the second paddle is in the closed position.

9. The valve repair system of claim 7 wherein an end of the movable arm of the first clasp extends past an end of the first paddle when the movable arm of the first clasp is in the extended position.

10. The valve repair system of claim 7 further comprising a spacer, wherein the spacer is disposed between the movable arm of the first clasp and the movable arm of the second clasp when the first paddle is in the closed position and the second paddle is in the closed position.

11. A valve repair device, comprising:

an anchor portion comprising a first anchor and a second anchor;

wherein the first anchor is configured to attach to a first leaflet of a native heart valve;

wherein the first anchor is configured to move between an open position and a closed position;

wherein the second anchor is configured to attach to a second leaflet of the native heart valve;

wherein the second anchor is configured to move between an open position and a closed position;

an indication feature that comprises one or more components of the first anchor that allow the first anchor to be in a non-extended position when the indication feature is in an allowable tension position and an extended position when the indication feature is in an exceeded tension position;

wherein when the first anchor and the second anchor are attached to the first and second leaflets of the native heart valve, the extended position indicates to a user when an amount of force applied to the anchor portion by the first and second leaflets of the native heart valve exceeds a predetermined amount of force.

12. The valve repair device of claim 11 further comprising a first paddle and a second paddle, wherein the first paddle and the second paddle are each moveable between an open position and a closed position.

13. A valve repair system for repairing a native heart valve of a patient during a non-open-heart procedure, the valve repair system comprising:

a delivery device having at least one lumen;

an actuation element that extends through the delivery device;

an anchor portion comprising a first anchor and a second anchor;

wherein the first anchor is configured to attach to a first leaflet of the native heart valve;

wherein the first anchor is configured to move between an open position and a closed position;

wherein the second anchor is configured to attach to a second leaflet of the native heart valve;

wherein the second anchor is configured to move between an open position and a closed position;

an indication feature that comprises one or more components of the first anchor that allow the first anchor to be in a non-extended position when the indication feature is in an allowable tension position and an extended position when the indication feature is in an exceeded tension position;

wherein when the first anchor and the second anchor are attached to the first and second leaflets of the native heart valve, the extended position indicates to a user when an amount of force applied to the anchor portion by the first and second leaflets of the native heart valve exceeds a predetermined amount of force.

14. The valve repair system of claim 13 further comprising a first paddle and a second paddle, wherein the first paddle and the second paddle are each moveable between an open position and a closed position.

* * * * *